United States Patent [19]
Kazama et al.

[11] Patent Number: 5,835,220
[45] Date of Patent: Nov. 10, 1998

[54] METHOD AND APPARATUS FOR DETECTING SURFACE FLAWS

[75] Inventors: Akira Kazama; Takahiko Oshige; Tsutomu Kawamura; Yuji Matoba, all of Kawasaki, Japan

[73] Assignee: NKK Corporation, Tokyo, Japan

[21] Appl. No.: 549,451

[22] Filed: Oct. 27, 1995

[51] Int. Cl.$^6$ .................................................. G01J 4/04
[52] U.S. Cl. ........................................ 356/369; 356/237
[58] Field of Search ................................ 356/369, 237, 356/430; 250/225

[56] References Cited

U.S. PATENT DOCUMENTS

| | | | |
|---|---|---|---|
| 4,482,250 | 11/1984 | Hirvonen et al. | 356/369 |
| 4,516,855 | 5/1985 | Korth | 356/369 |
| 4,655,595 | 4/1987 | Bjork et al. | |
| 4,740,079 | 4/1988 | Koizumi et al. | 356/237 |
| 5,438,415 | 8/1995 | Kazama | 356/369 |

FOREIGN PATENT DOCUMENTS

| | | |
|---|---|---|
| 52-138183 | 11/1977 | Japan . |
| 58-204356 | 11/1983 | Japan . |
| 62-070738 | 4/1987 | Japan . |
| 62-293104 | 12/1987 | Japan . |
| 1-211937 | 8/1989 | Japan . |
| 4-58138 | 2/1992 | Japan . |
| 4-78122 | 12/1992 | Japan . |
| 5-23620 | 5/1993 | Japan . |

*Primary Examiner*—Richard A. Rosenberger
*Attorney, Agent, or Firm*—Frishauf, Holtz, Goodman, Langer & Chick

[57] ABSTRACT

A method for detecting a surface flaw which includes the steps of (i) irradiating polarized light to a surface of a sample to be inspected and determining ellipso-parameters ($\Psi$, $\Delta$) of reflected light from the surface of the sample; (ii) irradiating light to a same position as irradiated by the polarized light and determining the intensity (I) of reflected light from the surface of the sample; and (iii) determining a type and grade of a flaw on the surface of the sample based on the ellipso-parameters ($\Psi$,$\Delta$) and the reflected light intensity (I). A surface flaw detecting apparatus includes (i) a first measuring device for irradiating polarized light to a surface to be inspected and measuring ellipso-parameters ($\Psi$,$\Delta$) of reflected light from the surface; (ii) a second measuring device for irradiating light to a same position as irradiated by the polarized light and measuring the intensity (I) of reflected light from that position; and (iii) an output device for outputting a three-dimensional coordinate position of $\Psi$, $\Delta$, I representing the reflected light from the surface, while sorting the position into a preset zone.

7 Claims, 46 Drawing Sheets

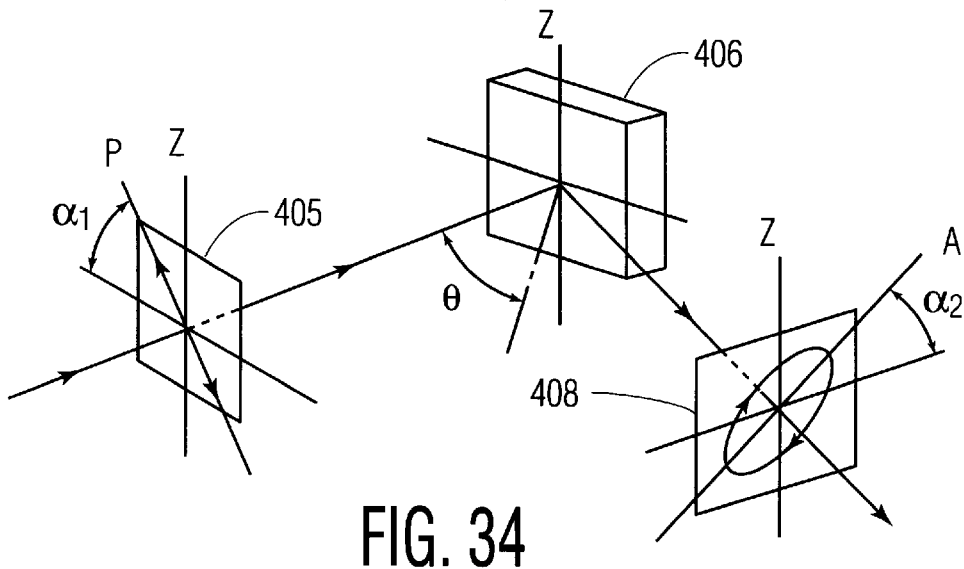
FIG. 34
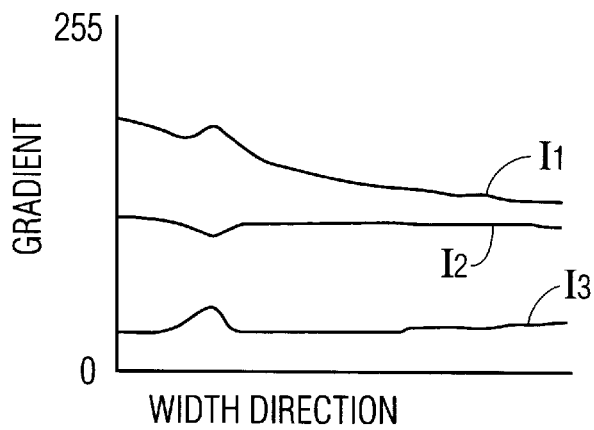

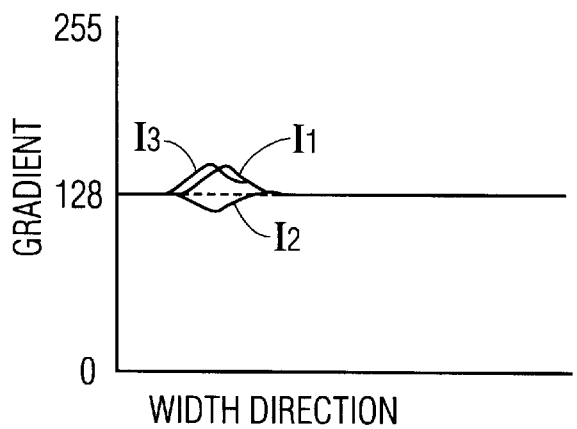
FIG. 35b

| FLAW TYPE | POLARITY PATTERN | VALUE PATTERN |
|---|---|---|
| X | +, +, + | 1.0 < 0.8 ≤ 1.0 |
| Y | −, −, − | 1.0 < 0.5 ≤ 1.0 |
| Z | −, −, − | 1.0 > 0.5 > 0.3 |
| ⋮ | ⋮ | ⋮ |
| W | −, −, − | > 0.8, 1.0, > 0.5 |

FIG. 46

| FLAW TYPE | PEAK VALUE | POLARITY PATTERN | VALUE PATTERN | VISUALLY EQUIVALENT LIGHT INTENSITY LEVEL | FLAW TYPE | GRADE |
|---|---|---|---|---|---|---|
| A | (38, 10, 32) | (+,+,+) | (1.0, 0.26, 0.84) | 4 | X | B |
| B | (-85, -19, -29) | (-,-,-) | (1.0, 0.22, 0.34) | 37 | Y | C |
| C | (-21, -18, -20) | (-,-,-) | (1.0, 0.86, 0.95) | -18 | Z | C |
| D | (144, 56, 120) | (+,+,+) | (1.0, 0.4, 0.8) | 32 | X | C |
| E | (60, 41, 60) | (+,+,+) | (1.0, 0.68, 1.0) | 41 | X | D |
| F | (-50, -17, -15) | (-,-,-) | (1.0, 0.34, 0.3) | 28 | Y | B |
| G | (23, -12, -17) | (+,-,-) | (1.0, 0.52, 0.74) | -52 | Z | D |
| H | (-34, -40, -38) | (-,-,-) | (0.93, 1.0, 0.95) | -44 | Z | C |

FIG. 48

| FLAW TYPE | POLARITY | | | FLAW FEATURE QUANTITY |
|---|---|---|---|---|
| | $\Psi_p$ | $\Delta_p$ | $I_{op}$ | $E_{pp}$ |
| S | − | + | − | 18 |
| T | − | − | − | 0 |
| U | + | + | − | 24 |
| V | − | − | + | 1 |
| W | + | 0 | − | 12 |

| FLAW TYPE | POLARITY | | | FLAW FEATURE QUANTITY |
|---|---|---|---|---|
| | $\Psi_p$ | $\Delta_p$ | $I_{op}$ | $E_{pp}$ |
| S | − | + | − | 18 |
| X | + | − | + | 8 |
| Y | − | − | − | 0 |
| Z | + | − | − | 6 |
| W | + | 0 | − | 12 |

METHOD AND APPARATUS FOR DETECTING SURFACE FLAWS

BACKGROUND OF THE INVENTION

1. Field of the Invention

The present invention relates to a method and apparatus for optically detecting surface flaws.

2. Description of the Related Arts

In order to optically detect surface flaws on steel plates or sheets, optical flaw detectors using a laser beam as a light source and utilizing change in a scattering or diffraction pattern of light are often employed. The conventional technique involves detecting flaws from change in a scattering or diffraction pattern of the laser beam caused by the flaws, and is effective in detecting such flaws as forming apparent irregularities on steel plate surfaces.

However, some flaws in the form of (rather than surfaces irregularities) unevenness in physical property values, unevenness in microscopic roughness, local presence of thin oxide films or the like, and unevenness in thickness of coating films, are difficult to detect by the above conventional measuring method. It is supposed, by way of example, that a steel plate surface having an oxide film of approximately 100 Å in a normal portion contains an abnormal portion in which the oxide film is locally as thick as approximately 400 Å. Hereinafter, such an abnormal portion will be referred to as a patterned flaw. There is a demand for detecting and removing such an abnormal portion as a flaw because the presence of the abnormal portion causes a painting failure in the undercoating process. But the difference in thickness of the oxide films between the normal and abnormal portions is buried in the roughness of the steel plate surface, and the abnormal portion cannot be detected by the method utilizing scattering or diffraction of light.

A surface inspecting method utilizing polarized light is known as means for detecting the flaws which are insensitive to scattering or diffraction. For example, Japanese Examined Patent Publication No. 5-23620 proposes a method of finding foreign matters on semiconductor wafers. With this method, flaws are detected by determining $\Psi$ of polarization parameters, i.e., an amplitude ratio ($\tan \Psi$) of P-polarized light and S-polarized light. (P-polarized light represents a component of an electric vector of the reflected light in the direction parallel to the incident plane and S-polarized light represents a component thereof in the direction vertical to the incident plane.) However, because there are surface flaws which form abnormal portions in spite of showing a constant ratio between the two polarized light components, the proposed method is impracticable to satisfy the above demand.

An ellipsometry technique is also known as a means for measuring a ratio of P- to S-polarized light component and a phase difference at the same time. Methods of testing characteristic values of material surfaces using ellipsometry are proposed in Japanese Examined Patent Publication No. 4-781211 and Japanese Patent Laid-Open No. 1-211937. However, it has been thought that those methods are too sensitive to detect surface flaws on the above-mentioned material and hence cannot be applied to flaw detection of steel plates. Thus, an effective technique for detecting patterned flaws of steel plates has heretobefore not been realized and practiced.

SUMMARY OF THE INVENTION

An object of the present invention is to increase the number of flaw types which can be detected or discriminated, and to detect patterned surface flaws which could not be detected by conventional methods.

To achieve the above object, a first aspect of the present invention provides a surface flaw detecting method comprising the steps of:

(a) irradiating polarized light to samples having surface flaws and determining characteristics of ellipso-parameters ($\Psi,\Delta$) of reflected light from surfaces of the samples;

(b) irradiating polarized light to a surface of a sample to be inspected and determining ellipso-parameters ($\Psi, \Delta$) of reflected light from the surface of the sample;

(c) comparing the ellipso-parameters ($\Psi, \Delta$) determined in the step (b) with the characteristics of the ellipso-parameters ($\Psi, \Delta$) determined in the step (a); and (d) grading a flaw on the sample surface based on the results compared in the step (c).

A second aspect of the present invention provides a surface flaw detecting method comprising the steps of:

(a) irradiating polarized light to a surface of a sample to be inspected and determining ellipso-parameters ($\Psi, \Delta$) of reflected light from the surface of the sample;

(b) irradiating light to the same position as irradiated by the polarized light in the step (a) and determining the intensity (I) of reflected light from the sample surface; and (c) determining the type and grade of a flaw on the sample surface based on the ellipso-parameters ($\Psi, \Delta$) determined in the step (a) and the reflected light intensity (I) determined in the step (b).

A third aspect of the present invention provides a surface flaw detecting apparatus comprising:

(a) means for storing characteristics of ellipso-parameters ($\Psi, \Delta$) of surface flaws in advance;

(b) means for irradiating polarized light to a surface to be inspected and measuring ellipso-parameters ($\Psi, \Delta$) of reflected light from the surface; and (c) means for comparing the measured ellipso-parameters ($\Psi, \Delta$) of the reflected light with the characteristics of the ellipso-parameters ($\Psi, \Delta$) in the storing means, and outputting compared results.

A fourth aspect of the present invention provides a surface flaw detecting apparatus comprising:

(a) means for irradiating polarized light to a surface to be inspected and measuring ellipso-parameters ($\Psi, \Delta$) of reflected light from the surface;

(b) irradiating light to the same position as irradiated by the polarized light and measuring the intensity (I) of reflected light from that position; and (c) means for outputting a three-dimensional coordinate position of $\Psi, \Delta, I$ representing the reflected light from the inspected surface, while sorting the position into any of preset zones.

A fifth aspect of the present invention provides a surface flaw detecting apparatus comprising;

(a) light irradiating means for irradiating polarized light in the form of parallel light flux to a surface to be inspected;

(b) light receiving means disposed respectively in different optical paths of reflected light from the inspected surface for receiving the reflected light from the inspected surface for conversion into image signals;

(c) the light receiving means comprising three analyzers having different azimuth angles from each other, and three linear array sensors for receiving lights having passed through the analyzers; and (d) signal processing means for processing image signals from the three linear array sensors, the signal processing section calculating an amplitude reflectance ratio tan $\Psi$, cos $\Delta$ indicative of the phase difference $\Delta$ and the intensity $I_0$ of the reflected light from the inspected surface, producing a tan $\Psi$ image, a cos $\Delta$ image and an $I_0$ image, and evaluating surface characteristics from densities of respective corresponding pixels on the tan $\Psi$ image, the cos $\Delta$ image and the Io image produced.

A sixth aspect of the present invention provides a surface flaw detecting apparatus comprising;

(a) light irradiating means for irradiating polarized light to a surface to be inspected over its full width;

(b) means disposed in an optical path of normally-reflected light of reflected light from the inspected surface for detecting the normally-reflected light;

(c) means disposed in an optical path of scatteringly-reflected light of the reflected light from the inspected surface for detecting the scatteringly-reflected light;

(d) at least one of the normally-reflected light detecting means and the scatteringly-reflected light detecting means comprising an optical system for separating the incoming light into three beams, analyzers disposed in respective optical paths of the separated three beams and having different azimuth angles from each other, and three image pickup means for receiving lights having passed through the analyzers; and (e) signal processing means for comparing image signals from the normally-reflected light detecting means and the scatteringly-reflected light detecting means, processing image signals from the three image pickup means receiving the lights having passed through the analyzers to calculate two ellipso-parameters, i.e., an amplitude reflectance ratio tan $\Psi$ and cos $\Delta$ indicative of the phase difference $\Delta$, of the reflected light from the inspected surface, whereby characteristics of the inspected surface being evaluated from the compared result between the normally-reflected light and the scatteringly-reflected light, as well as the amplitude reflectance ratio tan $\Psi$ and cos $\Delta$.

A seventh aspect of the present invention provides a surface flaw detecting apparatus comprising;

(a) light irradiating means for irradiating polarized light to a surface to be inspected over its full width;

(b) light receiving means disposed in an optical path of scatteringly-reflected light of reflected light from the inspected surface for receiving the scatteringly-reflected light;

(c) the light receiving means comprising an optical system for separating the incoming light into three beams, analyzers disposed in respective optical paths of the separated three beams and having different azimuth angles from each other, and three image pickup means for receiving lights having passed through the analyzers; and (d) signal processing means for processing image signals from the three image pickup means receiving the lights having passed through the analyzers to calculate two ellipso-parameters, i.e., an amplitude reflectance ratio tan $\Psi$ and cos $\Delta$ indicative of the phase difference $\Delta$, of the reflected light from the inspected surface, whereby characteristics of the inspected surface being evaluated from the amplitude reflectance ratio tan $\Psi$ and cos $\Delta$.

An eighth aspect of the present invention provides a surface flaw detecting apparatus comprising;

(a) light irradiating means for irradiating polarized light to a surface to be inspected;

(b) a three-plate type linear array camera for receiving reflected light from the inspected surface and outputting three different types of polarization image signals;

(c) the three-plate type linear array camera comprising a beam splitter for separating the incoming light into three beams, analyzers disposed in respective optical paths of the separated three beams and having azimuth angles of 0, $\pi/4$ and $-\pi/4$, and linear array sensors for receiving the lights having passed through the analyzers; and (d) signal processing means for processing polarization image signals output from the three-plate type linear array camera to calculate two ellipso-parameters, i.e., an amplitude reflectance ratio tan $\Psi$ and cos $\Delta$ indicative of the phase difference $\Delta$, of the reflected light from the inspected surface and the intensity $I_0$ of the reflected light from the inspected surface, whereby the presence or absence of flaws on the inspected surface is determined from the amplitude reflectance ratio tan $\Psi$, the phase difference $\Delta$ and the reflected light intensity $I_0$ calculated.

A ninth aspect of the present invention provides a surface flaw detecting apparatus comprising;

(a) light irradiating means for irradiating, to a surface to be inspected, polarized light being elongate in the direction of width of the inspected surface;

(b) light receiving means for receiving reflected light from the inspected surface for conversion into image signals, the light receiving means comprising three analyzers disposed in an optical path of the reflected light from the inspected surface and having different azimuth angles from each other, and linear array sensors for receiving the lights having passed through the analyzers; and (c) signal processing means for normalizing and leveling image signals output from the linear array sensors, and calculating relative values of two ellipso-parameters, i.e., an amplitude reflectance ratio tan $\Psi$ and cos $\Delta$ indicative of the phase difference $\Delta$, and the intensity $I_0$ of the reflected light based on the normalized image signals, whereby the presence or absence of abnormality on the inspected surface is determined from the calculated relative values of the amplitude reflectance ratio tan $\Psi$, the phase difference $\Delta$ and the reflected light intensity $I_0$.

A tenth aspect of the present invention provides a surface flaw detecting apparatus comprising:

(a) light irradiating means for irradiating polarized light to a surface to be inspected;

(b) light receiving means including a plurality of light receiving optical systems for receiving at least three polarized lights having polarizing planes of particular different angles, and detecting reflected light from the inspected surface for conversion into image signals; and (c) signal processing means for normalizing each of light intensity distributions output from the light receiving optical systems with respect to a preset reference value, and comparing change polarities and deviations of the normalized light intensity distributions with predetermined patterns for determining the flaw type.

An eleventh aspect of the present invention provides a surface flaw detecting apparatus comprising:

(a) light irradiating means for irradiating polarized light to a surface to be inspected over its full width;

(b) detecting means for receiving reflected light from the inspected surface for conversion into image signals, the detecting means comprising beam splitters for separating the reflected light from the inspected surface into three beams, analyzers disposed in respective optical paths of the separated three beams and having different azimuth angles from each other, and three sets of linear array sensors for receiving the lights having passed through the analyzers; and (c) signal processing means for processing signals from the detecting means, the signal processing means comprising flaw candidate area extracting means, parameter calculating means and determining means, the flaw candidate area extracting means comparing density levels of polarization images input from the three sets of linear array sensors with predetermined reference density levels, and extracting, as flaw candidate areas, the areas in which the measured density levels of the polarization images are out of the vicinity of the reference density levels, the parameter calculating means calculating ellipso-parameters and the intensity of the reflected light based on the measured light intensities for pixels within the extracted flaw candidate areas, the determining means comparing characteristics of the calculated ellipso-parameters and reflected light intensity with predetermined characteristics of surface flaws for determining the type and grade of a surface flaw.

BRIEF DESCRIPTION OF THE DRAWINGS

FIG. 34 is an explanatory view showing the operation principle of the optical system in the embodiment of FIG. 32.

FIGS. 35(a) and 35(b) are image density characteristic graphs showing a normalizing process in the embodiment of FIG. 32.

FIG. 46 is a reference pattern table showing flaw types, polarity patterns and value patterns.

FIG. 48 is a table showing specific examples of types and grades for various flaws.

Figure 1:
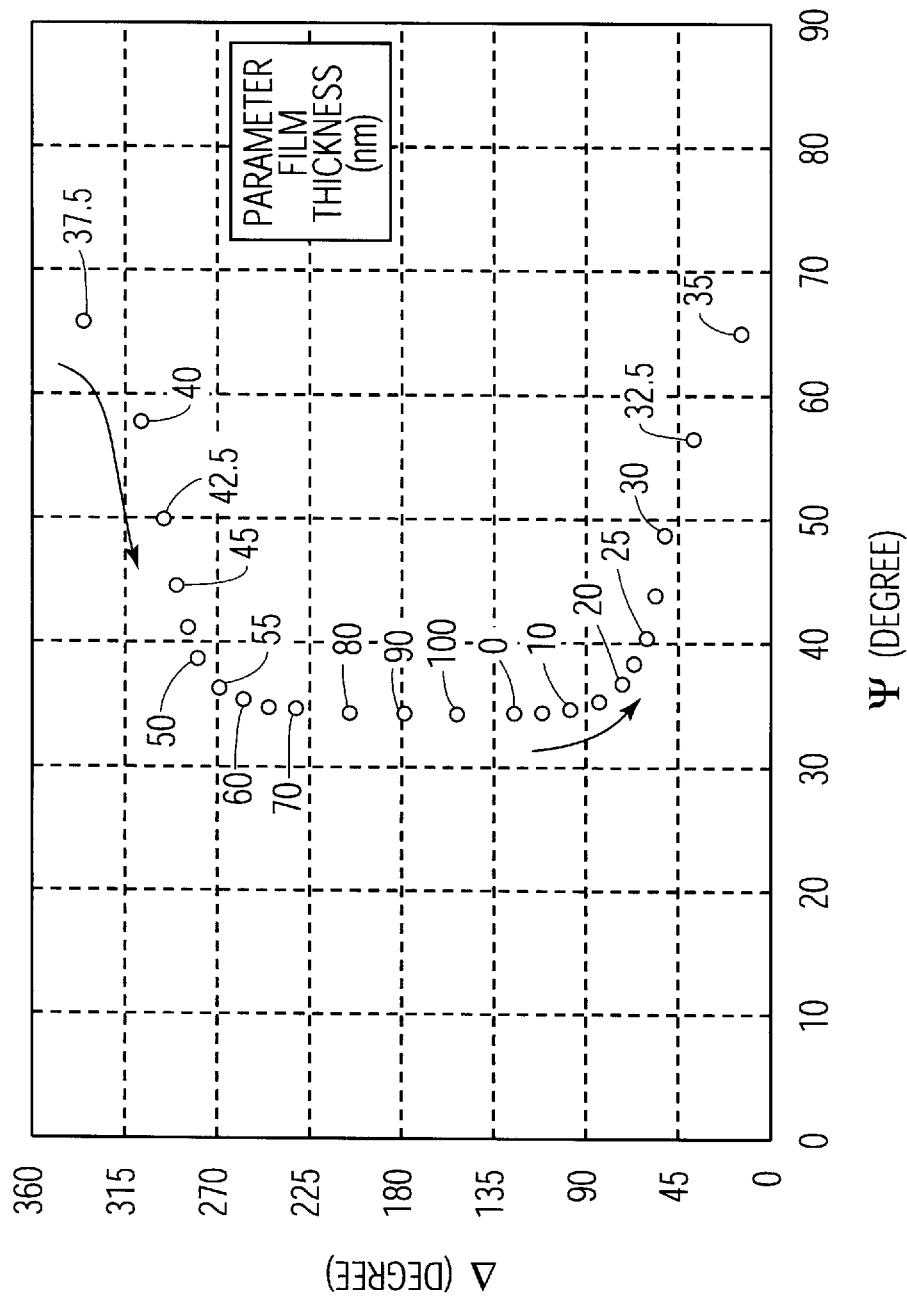
FIG. 1 is a graph showing ellipso-parameters resulted when an oxide film is deposited on a steel plate.

DESCRIPTION OF THE EMBODIMENTS
EMBODIMENT-1

Ellipso-parameters ($\Psi$, $\Delta$) are defined by the equation (1) below using a ratio $\rho$ of reflectance Rs of an S-component of polarized light to reflectance Rp of a P-component thereof;

$$\rho = Rs/Rp = \tan \Psi \cdot \exp(j\Delta) \tag{1}$$

where tan $\Psi$ represents an amplitude ratio of P- to S-component of the reflected light and exp(j$\Delta$) represents a phase difference between the P- and S-components. When the incident light is linearly polarized light of 0 degree (i.e., including only the P-component), the angle formed between the major axis of an ellipse defined by the P- and S-components of the reflected light and the incident plane corresponds to $\Psi$, and the phase difference between the P- and S-components corresponds to $\Delta$. In this case, $\Psi$, $\Delta$ can be calculated from the direction of major axis and the eccentricity of the ellipse by dividing the reflected light into components along any desired two polarizing axes orthogonal to each other and measuring the intensity of each of the polarized light components. The polarization state of the incident light can optionally be set and, in this case, $\Psi$, $\Delta$ are determined after compensating for the polarization state of the incident light.

The intensity I of the reflected light is determined from the following equation (2) based on the intensity $I_0$ of the incident light and the reflectance R of the surface:

$$I = I_0 \cdot R \tag{2}$$

When using such optical measured values, the present invention can be achieved as a surface flaw detecting method comprising the steps of irradiating polarized light to a surface to be inspected, determining ellipso-parameters ($\Psi$, $\Delta$) of reflected light from the surface, comparing the determined ellipso-parameters ($\Psi$, $\Delta$) with characteristics of an amplitude ratio $\Psi$ and a phase difference $\Delta$ of reflected light from surface flaws which have been determined beforehand, and grading an inspected surface flaw.

In another form, the present invention is achieved as a surface flaw detecting method comprising the steps of irradiating polarized light to a surface to be inspected and determining ellipso-parameters ($\Psi$, $\Delta$) of reflected light from the surface, irradiating the same or different light to the same location on the inspected surface and determining the intensity (I) of reflected light from the surface, and grading an inspected Surface flaw and determining the type of the flaw in accordance with the two ellipso-parameters and the intensity of the reflected light.

For implementing the surface flaw detecting method of the present invention, a surface flaw detecting apparatus comprises means for storing ellipso-parameters ($\Psi$, $\Delta$) of surface flaws, means for irradiating polarized light to a surface to be inspected and determining ellipso-parameters ($\Psi$, $\Delta$) of reflected light from the surface, and means for outputting compared results between measured characteristics of the reflected light and the stored characteristics.

In another form, a surface flaw detecting apparatus comprises means for irradiating polarized light to a surface to be inspected and determining ellipso-parameters ($\Psi$, $\Delta$) of reflected light from the surface, irradiating the same or different light to the same location on the inspected surface and determining the intensity (I) of reflected light from the surface, and means for outputting a three-dimensional coordinate position of $\Psi$, $\Delta$, I while sorting the position into any of preset zones.

In the case of a large inspected surface, a surface flaw detecting apparatus employs a plurality of two-dimensional image pickup devices as means for receiving the reflected light, and calculates $\Psi$, $\Delta$, I by using measured values of a pixel corresponding to the same reflecting point. In another form, a surface flaw detecting apparatus employs a monochromatic light source as a source of the polarized light, irradiates monochromatic polarized light over a predetermined range on the inspected surface by using optical fibers, and receives reflected light from the predetermined range of the inspected surface by a combination of a plurality of ellipso-meters.

Because polarization characteristics are sensitive to surface properties of materials, the use of polarization characteristics make it possible to measure the surface characteristics which cannot be detected by utilizing scattering or diffraction of light. The surface having a patterned flaw exhibit change in characteristics with regard to reflection of light, and the ellipso-parameters vary sharply. But, how change in the ellipso-parameters and surfaces flaws can be related with each other has heretofore been unknown. As a result of studying the relationship between change in the ellipso-parameters and surfaces flaws, the inventors have found that, for a patterned flaw, Ψ, Δ are varied with function characteristics depending on the range of thickness of an oxide film to be detected as a flaw, and a flaw portion and a normal portion can be discriminated based on the characteristics.

For a patterned flaw caused by a foreign matter deposited on a film, optical reflectance is also changed along with the ellipso-parameters because the flaw forms surface irregularities. In this case, a flaw portion and a normal portion can be discriminated by a combination of change in the ellipso-parameters and change in the reflectance or the intensity of the reflected light. Further, since such a combination is reproduced for some types of flaws, the extent and type of flaws can be discriminated by combining change in the ellipso-parameters and change in the intensity of the reflected light.

The ellipso-parameters are generally determined by an apparatus for measuring the parameters for each of points on the surface using a plurality of light receiving devices. However, the inventors propose an apparatus using a two-dimensional image pickup device. When the ellipso-parameters and the intensity of the reflected light are measured over a wide inspected surface, the reflected light from the inspected surface is introduced through a plurality of optical systems and focused on two-dimensional image pickup devices. The ellipso-parameters and the intensity of the reflected light are calculated from the light intensities of those pixels measured by a plurality of image pickup devices which correspond to the same point on the inspected surface. By modifying the optical system so as to measure the intensity of the reflected light from the same reflecting point, the optical system becomes simpler than in the case of scanning the inspected surface by a single light measuring means.

Further, a light source with high output power, such as a laser beam source, is available When the ellipso-parameters are measured over a wide range by using a single laser beam source and a plurality of ellipso-meters, it is advantageous to divide light from the same light source into plural rays through optical fibers for irradiation of the wide range, because the irradiation intensity in any parts of a large-wide material becomes uniform and compensation of the intensity of the reflected light is facilitated.

The first operation principle of the present invention will be described with reference to FIG. 1.

FIG. 1 shows a behavior of change in polarization parameters as resulted when an oxide film of 5 nm to 100 nm is deposited on a cold-rolled steel plate. FIG. 1 is the so-called "Ψ- Δ chart" for use in ordinary polarization analysis wherein the horizontal axis represents an angle Ψ indicative of an amplitude ratio of P- to S-polarized light, the vertical axis represents a phase difference Δ between P- and S-polarized light, and plotted numerals each represent a thicknesses of an oxide film measured by separate means. Results of FIG. 1 are mastered on condition that the light source is a He—Ne laser having wavelength of 633 nm, the incident angle for measurement is 70 degrees, and an oxide film with refractivity of 0.3 is deposited on a steel plate with complex refractivity of 2.0+i4.0.

As seen from FIG. 1, when the thicknesses of the oxide film is in the range of approximately 20 to 50 nm, change in Ψ is found, but when it is in the ranges of 0 to 20 nm and 50 to 100 nm, change in Δ predominates and Ψ is almost unchanged. In other words, when the control range of the oxide film thickness is from 0 to 20 nm or from 50 to 100 nm, thickness unevenness cannot be detected as a flaw by observing Ψ alone. In the present invention, therefore, Ψ and Δ are both determined at the same time and a wide range of the oxide film thickness is evaluated by applying the measured values to the corresponding line of the plotted curve. For example, when Ψ is approximately 35 degrees and Δ is in the range of 100 to 250 degrees, the film thickness is calculated based on any of two lines covering the ranges of 50 to 100 nm and 0 to 20 nm. Also, when Ψ is not less than 40 degrees and Δ is not in the range of 100 to 250 degrees, the film thickness is calculated based on any of two lines covering the ranges of 20 to 35 nm and 35 to 50 nm. The control range representing a normal range of the film thickness is decided depending on the type and thickness of steel plates, and an inspected portion showing a film thickness out of the control range is detected as a flaw.

The second operation principle of the present invention will be described with reference to FIG. 1.

Figure 2A:
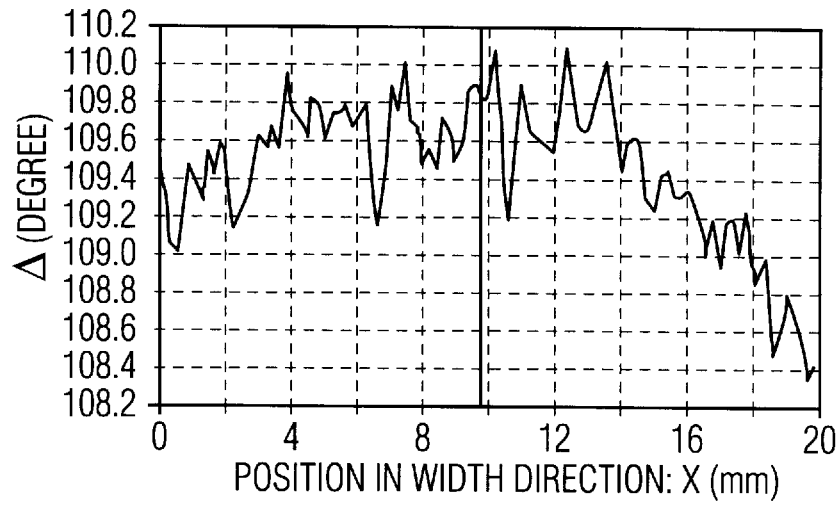
FIGS. 2(a) to 2(c) are graphs showing reflection characteristics of a type A flaw.
Figure 2B:
Figure 2C:
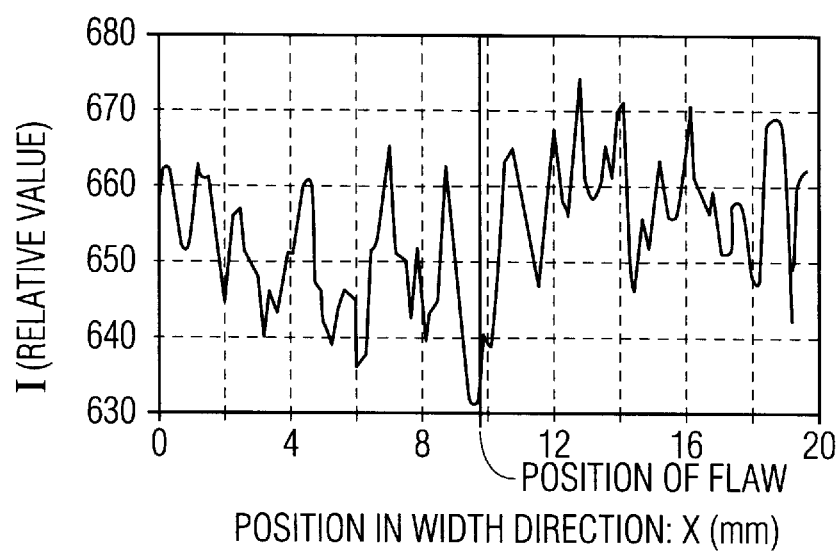

FIGS. 2(a) to 2(c) show an example of charts resulted from detecting a type A flaw of patterned flaws. The flaw extends linearly at the middle in the horizontal or widthwise direction on the charts. Detected values of the ellipso-parameters and the intensity of the reflected light are plotted over a width range of 20 nm indicated by the horizontal axis. The phase difference (Δ) and the intensity (I) corresponding to the flaw are not clearly discriminated from those corresponding to a normal portion (except the middle in the horizontal direction). However, values of the amplitude ratio (Ψ) can apparently be discriminated between the portion including the flaw (i.e., the middle) and the portion including no flaws (i.e., area except the middle). The type A flaw is a thin oxide film on the surface which could not be detected by any conventional optical detectors.

Figure 3A:
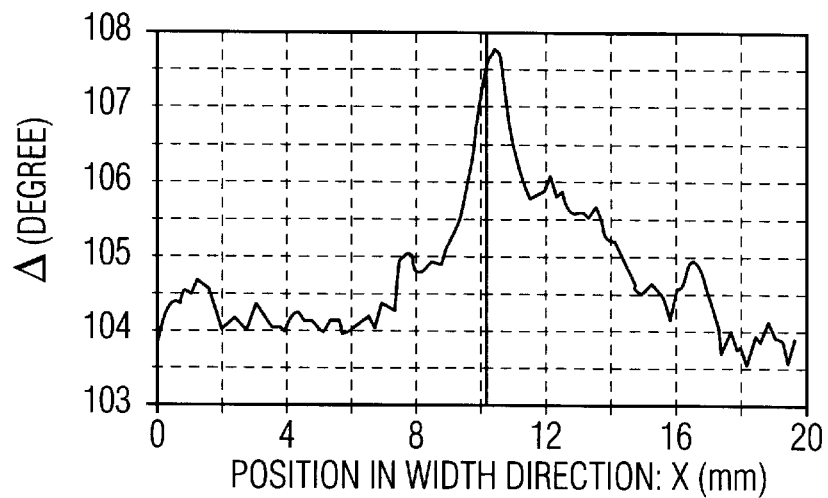
FIGS. 3(a) to 3(c) are graphs showing reflection characteristics of a type B flaw.
Figure 3B:
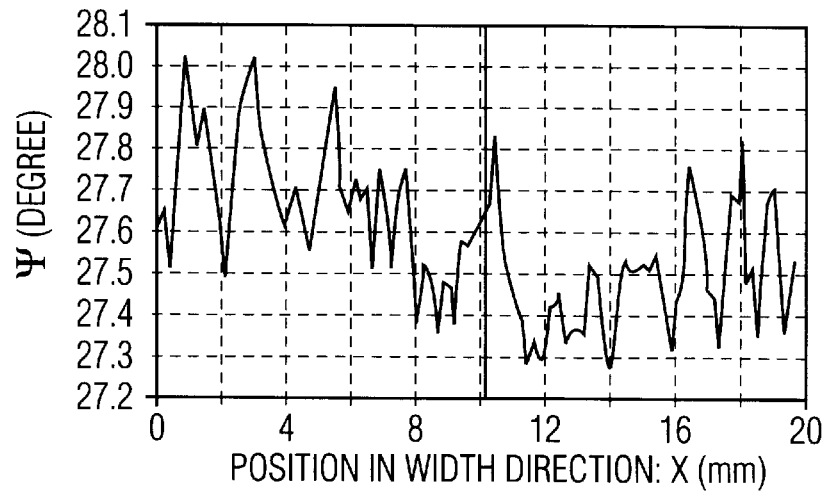
Figure 3C:
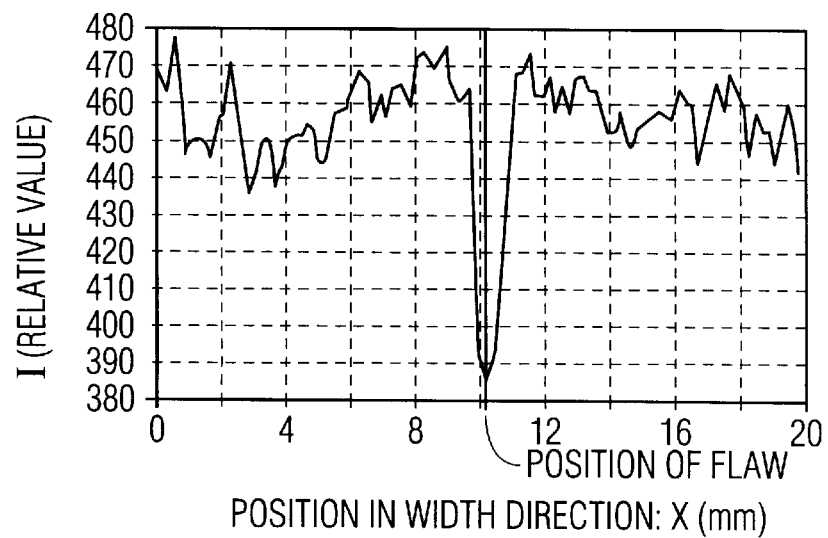

FIGS. 3(a) to 3(c) show an example of charts resulted from detecting a type B flaw of patterned flaws. The presence of this type flaw cannot be discriminated from Ψ, but can be detected from the phase difference (Δ) and the intensity (1). The type B flaw often appears when surface roughness of steel plates is varied in a microscopic scale. Such a roughness variation is caused, for example, if the roll texture for rolling is partly roughed.

Figure 4A:
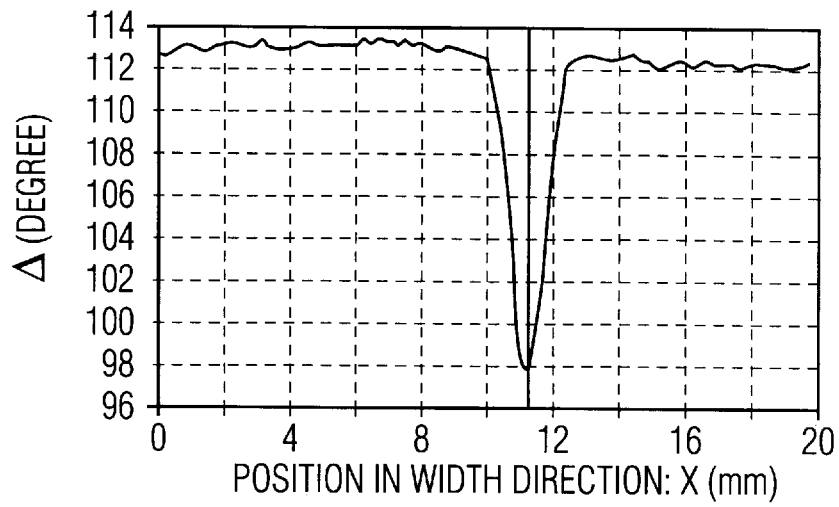
FIGS. 4(a) to 4(c) are graphs showing reflection characteristics of a type C flaw.
Figure 4B:
Figure 4C:
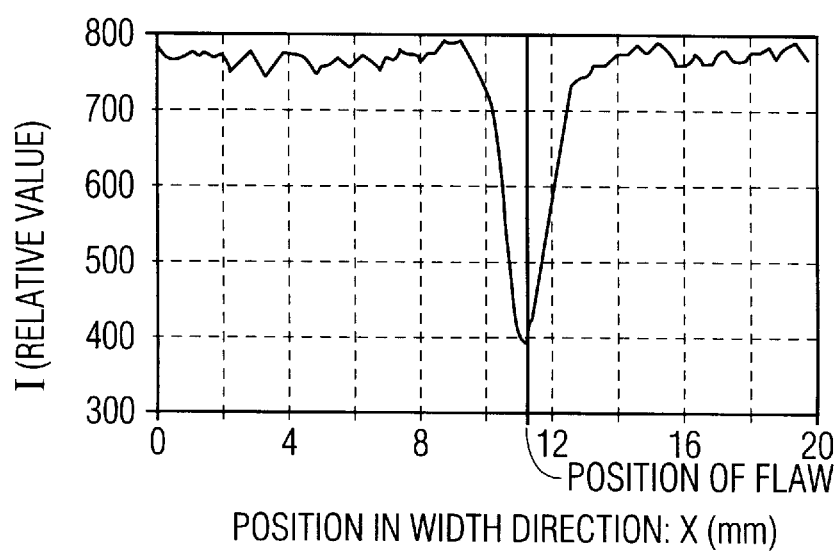

FIGS. 4(a) to 4(c) show an example of charts resulted from detecting a type C flaw of patterned flaws. This type flaw shows remarkable change in all the parameters Ψ, Δ and I. The type C flaw is caused by a deposit superposed on the patterned flaw such that apparent roughness of the steel plate surface is varied to a large extent. This type flaw is a visually discernable deposit and can be detected by conventional detectors.

As seen from FIGS. 2 to 4, whether the intensity of the reflected light changes or not depends on the type of flaws. Also, values of the ellipso-parameters change in different manners depending on the type of flaws.

An example of means for discriminating the type of flaws will be described below. Values of I, Ψ, Δ may partly be varied, they cannot be determined precisely as absolute values. Therefore, the moving average of each parameter is measured beforehand and a deviation from the average value is detected. The constant of the moving average is defined depending on the flaw size to be occurred. When change exceeding the constant is detected, absolute values of the measured angles are taken as evaluation values for the ellipso-parameters, while a deviation from the average value is taken as an evaluation value for the intensity of the reflected light. The absolute values of Ψ, Δ and the deviation of the intensity of the reflected light constitute a three-dimensional space. The three-dimensional space is divided based on experimental results into a plurality of zones which are given with flaw types and grades. If a flaw has properties common to several zones, these zones may be grouped and indicated by a common grade.

An apparatus for measuring the ellipso-parameters can be implemented in various ways with regard to an optical system. Tile inventors have previously proposed several optical systems which can not only determine the ellipso-parameters ($\Psi,\Delta$), including an absolute value of the phase difference $\Delta$, but also compensate for change in the intensity of the incident light, by measuring four polarized light components of the reflected light(see Japanese Patent Laid-Open No. 5-113371). A surface flaw detecting apparatus shown in FIG. 5 as an embodiment of the present invention can be constructed by using any one of the proposed optical systems.

Figure 5:
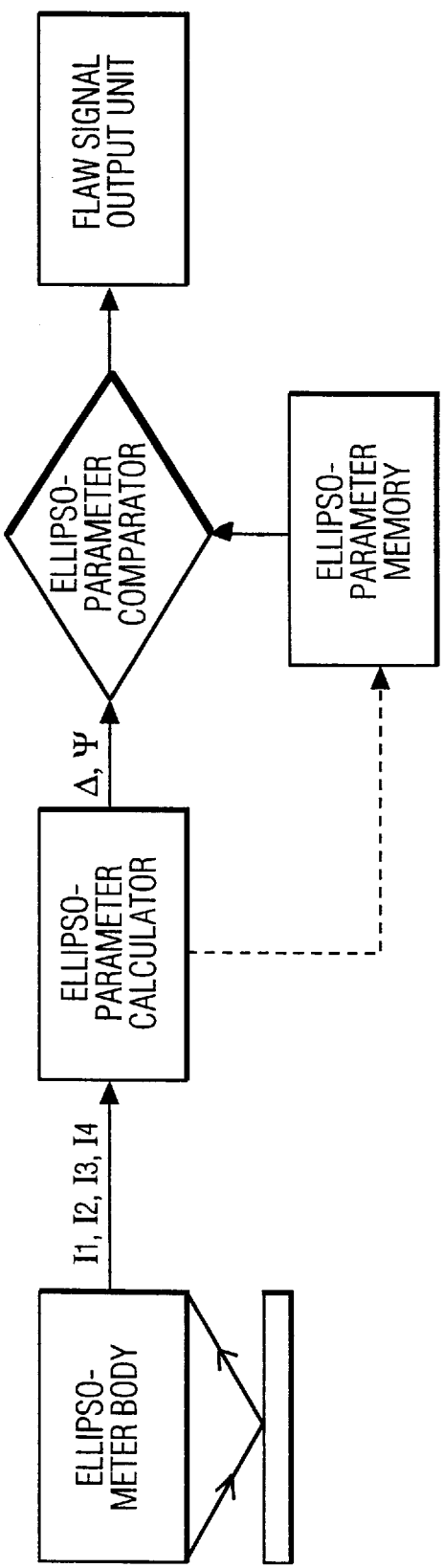
FIG. 5 is a block diagram showing an embodiment of a surface flaw detecting apparatus of the present invention.

The surface flaw detecting apparatus shown in FIG. 5 comprises an ellipso-meter body 1, an ellipso-parameter calculator 3 for calculating the ellipso-parameters from outputs of the ellipso-meter body 1, an ellipso-parameter memory 4 for storing the ellipso-parameters resulted when detecting a sample 2 having a flaw, an ellipso-parameter comparator 5 for comparing the ellipso-parameters resulted when detecting a sample 2 of which characteristics are not yet known and the characteristic values of the flaw stored in the memory 4, and a flaw signal output unit 6 for outputting the presence or absence of flaws, flaw grades, etc. depending on the compared results.

Figure 6:
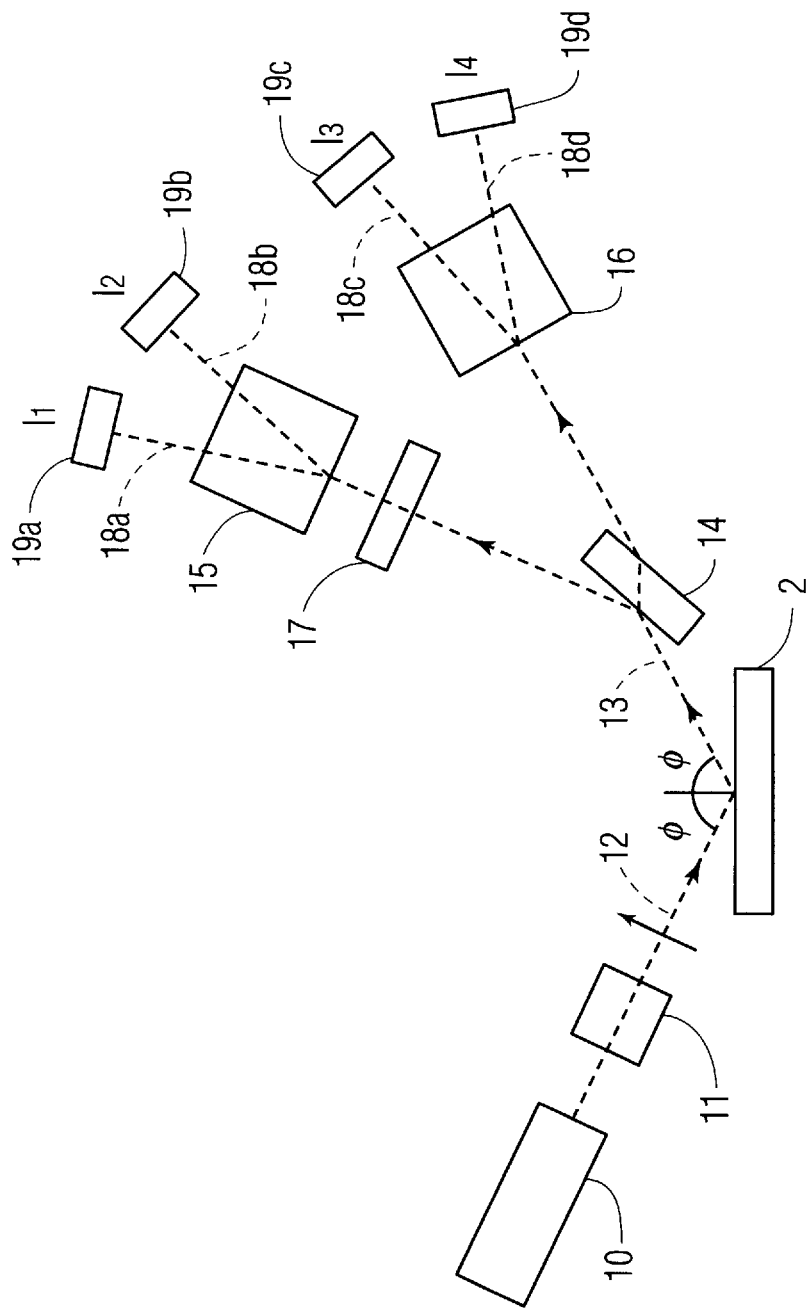
FIG. 6 is a view showing one example of an optical system of an ellipso-meter according to the present invention.

The ellipso-meter body 1 is constructed by, for example, an optical system shown in FIG. 6. Referring to FIG. 6, denoted by 10 is a laser beam source, 11 is a polarizer, and 12 is incident light. The incident light 12 is converted into polarized light through the polarizer 11 and then reflected by the surface of the sample 2. Reflected light 13 is divided through beam splitters 14, 15, 16 and a ¼ wavelength plate 17 into four polarized lights 18a, 18b, 18c, 18d different from each other which are detected light sensors 19a, 19b, 19c, 19d to measure light intensities $I_1$, $I_2$, $I_3$, $I_4$, respectively.

The ellipso-parameter calculator 3 calculates the ellipso-parameters from the measured light intensities by using equations (3), (4) below;

$$\tan \Delta = [\sigma_R(I_1-I_2)]/[\sigma_T(I_3-I_4)] \qquad (3)$$

$$\tan \Psi = [(\sigma_R^2-\sigma_T^2)/2] \cdot [\{\sigma_R(I_1-I_2)\}^2 + \{\sigma_T(I_3-I_4)\}^2]^{1/2} \div [\sigma_R^2(I_1+I_2) - \sigma_T^2(I_3+I_4)] \qquad (4)$$

where $\sigma_R$ and $\sigma_T$ are an amplitude reflectance ratio and an amplitude transmittance ratio of P- to S-polarized light after the non-polarizing beam splitter 14, respectively, and take values specific to the optical part.

The ellipso-parameter memory 4 stores characteristics of the ellipso-parameters resulted when detecting the sample 2 having flaws in advance. For example, the characteristics of an oxide film shown in FIG. 1 are stored in the memory 4.

When the ellipso-parameters of the sample 2 having not yet known characteristics are detected, the ellipso-parameter comparator 5 compares the detected results with the characteristics measured beforehand and stored in the memory 4. The comparison is carried out by employing a zone dividing process in terms of $\Psi$, $\Delta$. Consequently, the comparator 5 outputs a film thickness signal.

The flaw signal output unit 6 includes criteria for determining whether the measured film thickness is good or not. If the film thickness is within a predetermined range, the unit 6 determines the sample to be normal, but if it is outside the predetermined range, the unit 6 determines the sample to be abnormal and outputs an alarm.

Figure 7:
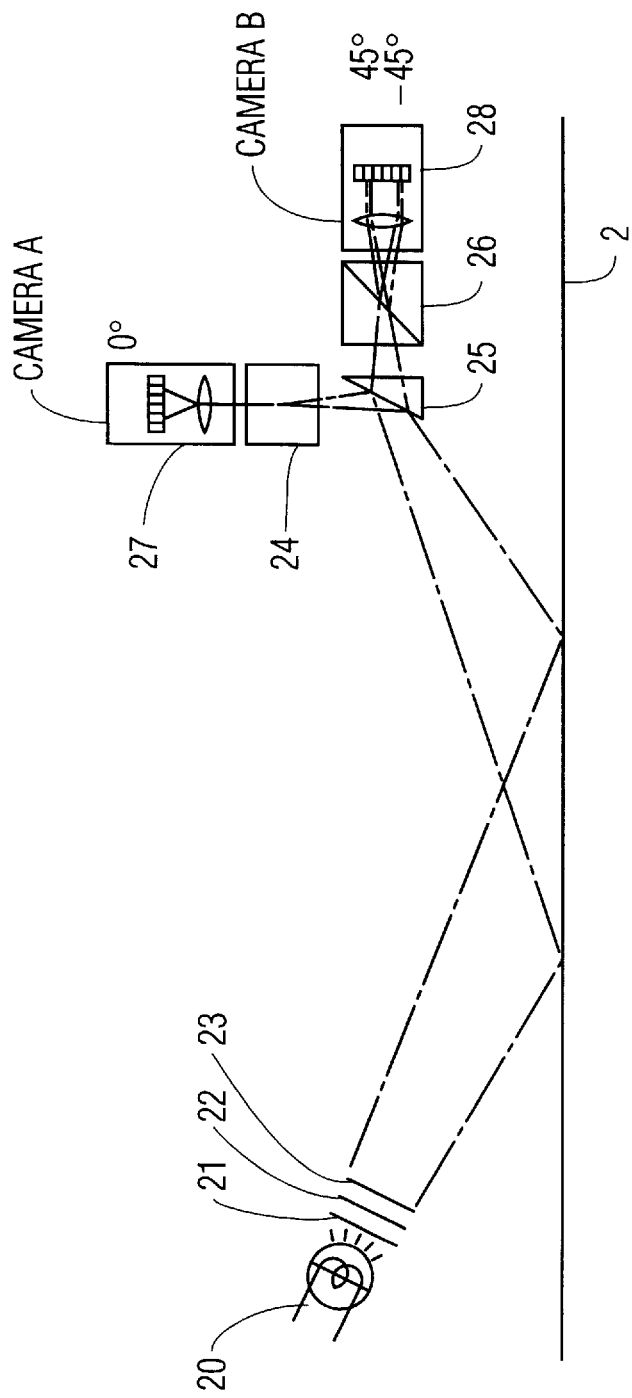
FIG. 7 is a view showing another example of the optical system.

Another optical system for implementing the present invention is shown in FIG. 7. Specifically, FIG. 7 shows an optical system section in a surface flaw detecting apparatus which is applied to a running line of steel plates. This optical system comprises a system for measuring the ellipso-parameters and a system for measuring the intensity of the reflected light. With this optical system, since the intensity of the incident light is made uniform over the inspected area of a sample and free from time-dependent change, the intensity (I) and the ellipso-parameters $\Psi$, $\Delta$ of the reflected light can be determined by measuring three polarized light components of the reflected light through both the systems and executing calculation based on the measured results.

In the ellipso-parameter measuring system, light emitted from a high-luminance light source 20 is polarized through a polarizing plate 23 and then irradiated to the surface of a sample 2. Reflected light from the sample surface is divided by a Wollaston prism 26 into two polarized light components orthogonal to each other at 45° and −45°, and the intensities of the polarized light components are measured by a camera B using two-dimensional CCD devices for each pixel. The camera B is designed to focus separate images of the two polarized light components on different parts of a single CCD camera. The optical system may be modified such that the two polarized light components are separately picked up by two different cameras. The light intensities picked up by the camera B are output to an ellipso-parameter calculator (not shown in FIG. 7) in which the ellipso-parameters for each point on the sample surface are calculated from the light intensities.

The system for measuring the intensity of the reflected light will now be described. The light emitted from the high-luminance light source 20 is passed through a diffusing plate 21 to have uniform intensity distribution and then irradiated to the surface of the sample 2. Reflected light from the sample surface is reflected by the surface of a non-polarizing prism 25 and enters a camera A 27 after passing through a polarizer 24 which is set to have a polarizing axis angle of 0 degree. In the camera, the light intensities for respective points on the inspected surface are measured at the same time by using two-dimensional CCD devices. In the case of the optical system shown in FIG. 7, the intensity (I) of the reflected light is determined from $I=I_2+I_3-2I_1$ where $I_1$ is the light intensity detected by the camera A and $I_2$, $I_3$ are the light intensities detected from images of the 45° and −45° polarized lights on the camera B, respectively.

The optical system of FIG. 7 is featured in that a wide range of the sample is uniformly irradiated by the polarized light, and the ellipso-parameters and the intensity of the reflected light for each of many points on the sample surface can be calculated from the images formed by lights having the polarizingaxis angles of 0, 45 and −45 degrees. Outputs of the cameras are processed to evaluate the film thickness and the flaw type from comparison with the stored patterns.

Figure 8:
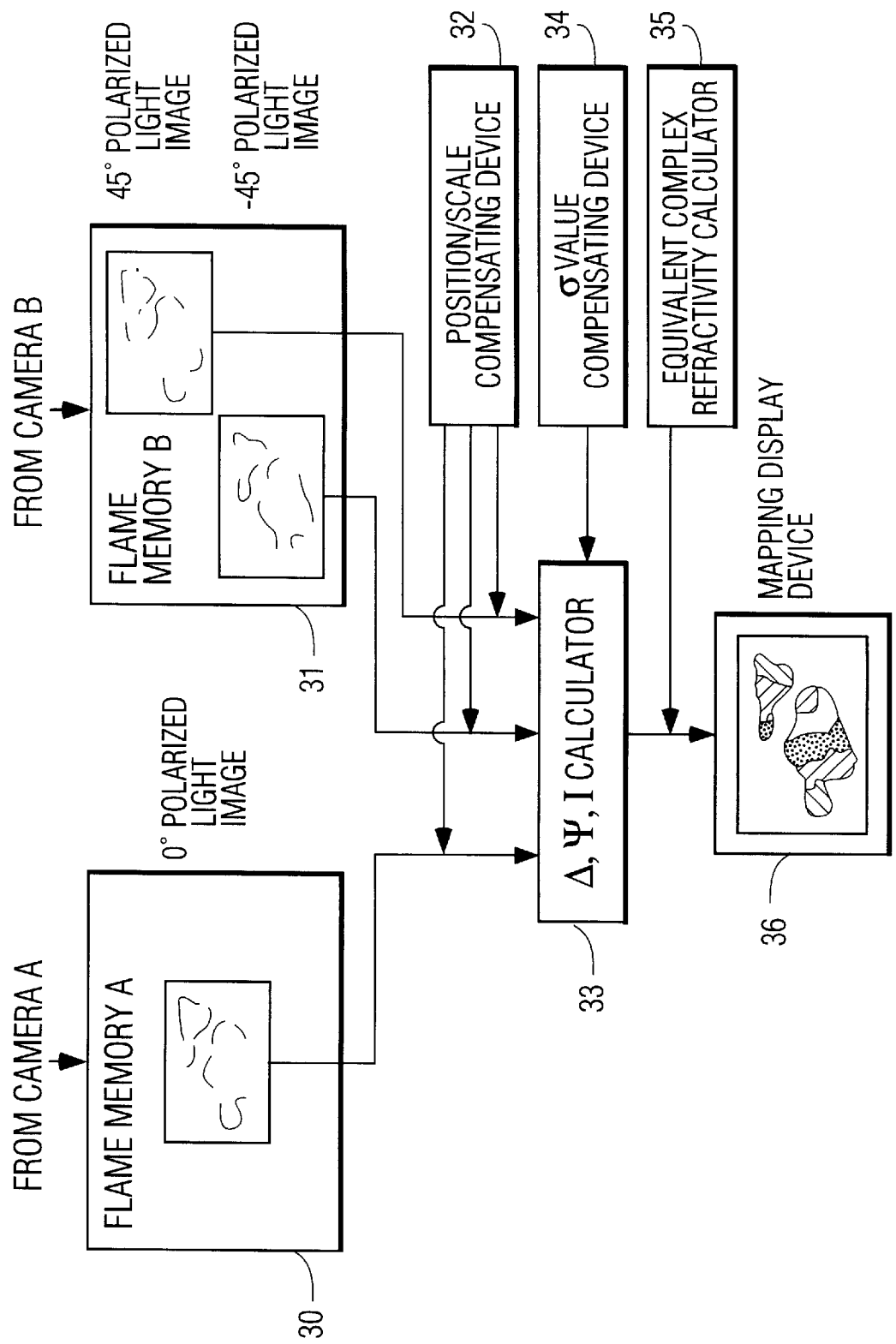
FIG. 8 is a block diagram showing an embodiment of a signal processing system according to the present invention.

FIG. 8 shows a signal processing system in the apparatus for detecting flaws by using the intensity of the reflected light and the ellipso-parameters at the same time. In other words, the signal processing system of FIG. 8 corresponds to a section in the surface flaw detecting apparatus which processes output signals from the optical system shown in FIG. 7.

The output signals from the cameras A, B are once stored respectively in frame memories A 31 and B 31. Since the frame memory B stores two images corresponding the two polarizing axes orthogonal to each other, total three data of light intensity information for each point on the sample surface are obtained in addition to an image corresponding to the non-polarized light intensity. Because values of $\Delta$, $\Psi$, I are affected on each of the frame memories due to positional shifts depending on the viewing angle, a position/scale compensating device 32 carries out a process for making the position and scale, which are determined from the Fresnel coefficients of the optical system, identical for each point on the sample surface in the images of three polarized light components stored in the frame memories. Then, a $\Delta$, $\Psi$, I calculator 33 calculates values of $\Delta$, $\Psi$, I for each correspond pixel. An equivalent complex refractivity calculator 35 calculates equivalent complex refractivity at each point on the sample surface from the values of $\Delta$, $\Psi$, I calculated from the reflected light, taking into account the polarization state of the incident light. The calculated results are indicated on a display 36 as an image of the sample surface condition through a suitable mapping process. In a simpler manner, the image values of $\Delta$, $\Psi$, I may directly be compared with the past data.

Figure 9:
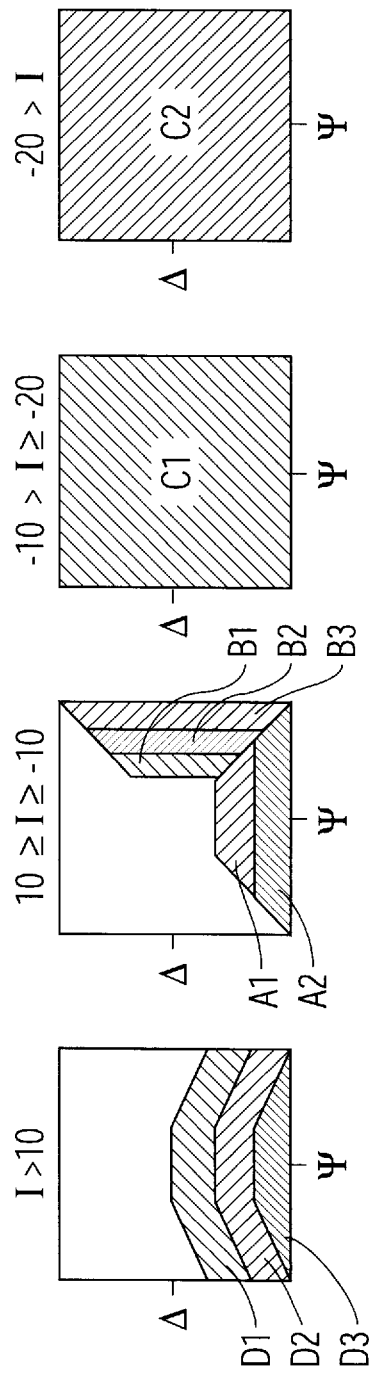
FIGS. 9(a) to 9(d) are diagrams showing an embodiment of mapping according to the present invention.

FIGS. 9(*a*) to 9(*d*) show examples of the mapping process applied to the flaws shown in FIGS. 2 to 4. FIG. 9(*a*) represents a discrimination diagram applied to the case where the intensity I of the reflected light is in excess of the normal value. When the values of $\Delta$, $\Psi$ are within respective hatched areas in FIG. 9(*a*), the inspected flaw is evaluated as grade 1, 2 and 3 of the type D flaw. FIG. 9(*b*) is applied to the case where the intensity I of the reflected light is at the normal value. Depending on the values of $\Delta$, $\Psi$, the type A or B and the grade 1, 2 or 3 are assigned as indicated by respective hatched areas. Likewise, FIGS. 9(*c*) and 9(*d*) are applied to the case where the intensity I of the reflected light is lower than the normal value. In this case, regardless of the values of $\Delta$, $\Psi$, the flaw type and the grade are assigned depending on the intensity alone.

Figure 10:
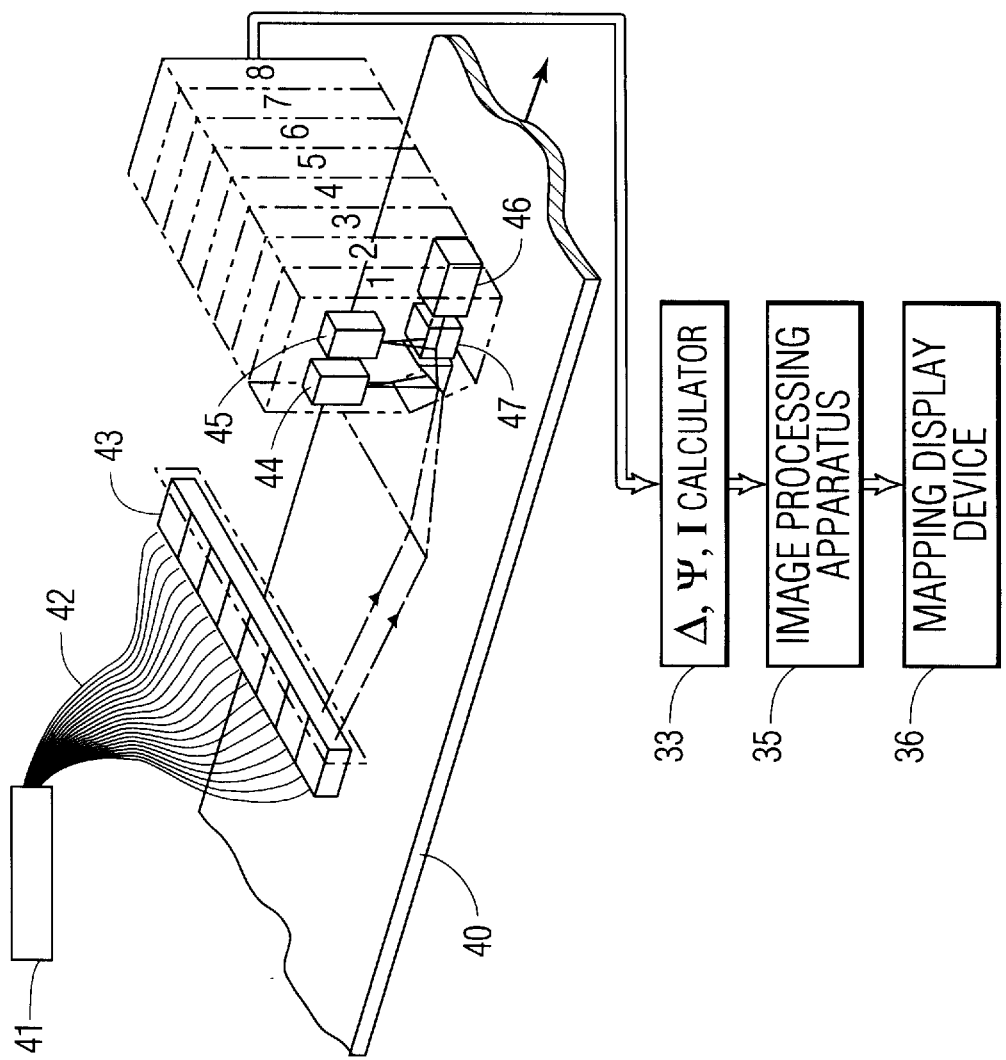
FIG. 10 is a view showing another embodiment of the flaw detecting apparatus according to the present invention.

FIG. 10 shows another surface flaw detecting apparatus of the present invention wherein multi-channel ellipso-meters are arranged side by side. This apparatus intends to detect flaws on a wide-width steel plate 40 being 2000 mm wide and moving at a maximum line speed of 600 m/minute. A light source is a laser 41 having wavelength of 800 nm, and light emitted from the laser 41 is introduced toward the surface to be measured through optical fibers 42. The incident light is converted through polarizing plates 43 into polarized light of 45 degrees. The incident angle to the steel plate surface is set to 65 degrees. Instead of the optical fibers, the laser beam may be formed into slit-shaped parallel light by using a paraboloidal mirror for irradiation to the steel plate surface. Eight sets of light detecting cameras 44, 45, 46, each being of a one-dimensional CCD camera comprising 1024 pixels, are arranged to observe the steel plate surface with widthwise resolution of 0.25 mm and one channel covering a 250 mm width of the steel plate.

An image processing apparatus is provided for each of heads 1 to 8 to calculate the intensity of polarized light at a speed in match with the line speed. To increase the processing speed, a $\Delta$, $\Psi$, I calculator 33 carries out processing of image data from eight sets of the cameras in parallel. When the line speed is slow or when resolution required is low, the number of sets may be reduced while increasing the number of processing stages executed in parallel. Signals from the calculator 33 are introduced to an image processing apparatus 34 for calculating the ellipso-parameters, and flaw discrimination is then performed in a mapping/display device 36.

In the mapping process of this apparatus, when a flaw appears in the image, the flaw type is determined depending on combinations of which ones of $\Delta$, $\Psi$, I are changed. The extent of the flaw is determined for $\Delta$ shown in FIG. 4(*a*), by way of example, depending on how degree the value of $\Delta$ is changed in the range from about 113° representing the normal portion to 98° representing the flaw. In the case of FIG. 4(*a*), when the change value of $\Delta$ is within 2° to 3°, the flaw is not problematic, but if it exceeds such a level, quality of the steel plate is not allowable and the flaw is detected as an abnormal portion, followed by outputting an alarm.

While oil is coated on steel plates to be inspected, oil has basic properties determined based on ellipsometry and, therefore, unevenness in thickness of an oil film can also be measured.

In any of the foregoing optical systems, the light source used for measuring the light intensity is the same as used for measuring the ellipso-parameters. These light sources are not necessarily the same, and a normal light source for measuring the light intensity and a polarized light source for measuring the ellipso-parameters may be independently of each other.

By comparing the measured ellipso-parameters with the stored values, it is possible to detect the patterned flaws on steel plate surfaces which could not be detected in the past. A combination of the ellipso-parameters and the intensity of the reflected light enables the flaw type to be determined. Using the two-dimensional image pickup device provides a more compact optical system. When measuring wide-width materials, the irradiation light is made uniform and precise measurement can be performed with simple compensation by introducing the light emitted from the light source through optical fibers.

EMBODIMENT-2

A surface flaw detecting apparatus according to this embodiment comprises a light irradiating section, a light receiving section, and a signal processing section. The light irradiating section emits polarized light in the form of parallel light flux for irradiation to a surface to be inspected. The light receiving section converts the reflected light from the inspected surface into image signals. The light receiving section comprises three analyzers having different azimuth angles from each other, which are disposed in each of different paths of reflected light from the inspected surface, and three linear array sensors for receiving lights having passed through the analyzers. The signal processing section processes signals from the three linear array sensors, calculates an amplitude reflectance ratio $\tan \Psi$, $\cos \Delta$ indicative of the phase difference $\Delta$ and the intensity $I_0$ of the reflected light from the inspected surface, produces a $\tan \Psi$ image, a $\cos \Delta$ image and an $I_0$ image, and evaluates surface characteristics from densities of respective corresponding pixels of the $\tan \Psi$ image, the $\cos \Delta$ image and the $I_0$ image produced.

By way of example, the light irradiating section has a parallel light source formed to extend in the direction of width of the inspected surface, and light from the parallel light source is irradiated to the inspected surface as polarized light through a polarizer. Reflected light from the inspected surface is received for detecting whether an abnormal portion such as a flaw exists on the inspected surface or not.

By way of example, the light receiving section comprises three line sensor cameras and three analyzers disposed in front of light receiving surfaces of the line sensor cameras. The three analyzers are arranged such that they have different azimuth angles from each other, i.e., such that the angles formed between their transmission axes and the incident plane on the inspected surface are, e.g., 0, $\pi/4$ and $-\pi/4$. The three line sensor cameras receive polarized lights having passed through the respective analyzers and output images indicative of intensity distributions of the polarized lights.

By way of example, the signal processing section calculates polarization parameters for respective corresponding pixels of the images indicative of the light intensity distributions output from the three line sensor cameras, i.e., an amplitude reflectance ratio tan Ψ, cos Δ indicative of the phase difference Δ and the intensity $I_0$ of the reflected light from the inspected surface. Then, it produces images of the polarization parameters, i.e., a tan Ψ image, a cos Δ image and an $I_0$ image. Further, it determines the type of an abnormal portion depending on whether bright and dark patterns of the produced tan Ψ, cos Δ and $I_0$ images in the abnormal portion coincide with each other or not, and also determines the extent of abnormality depending on the degree of luminance change in these pimage.

Figure 11:
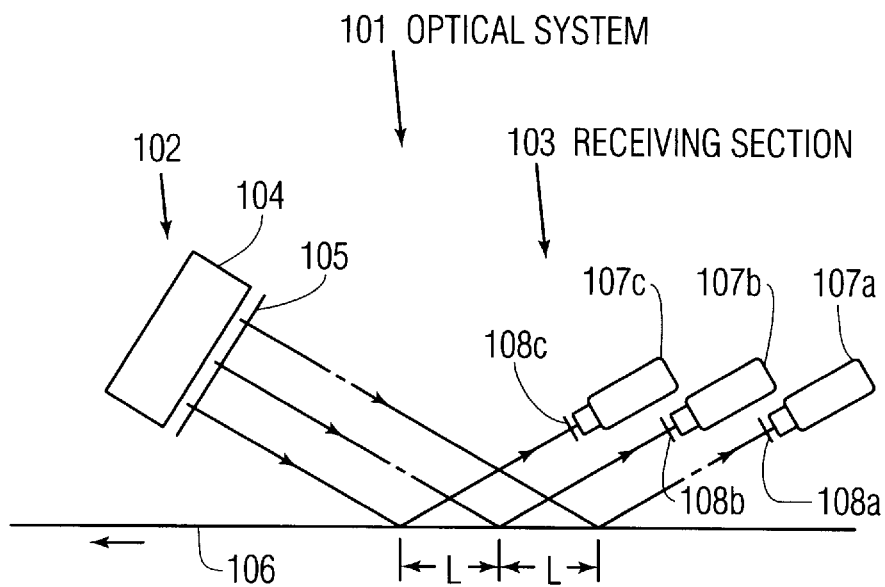
FIG. 11 is a layout view showing an optical system in an embodiment of the present invention.
Figure 12:
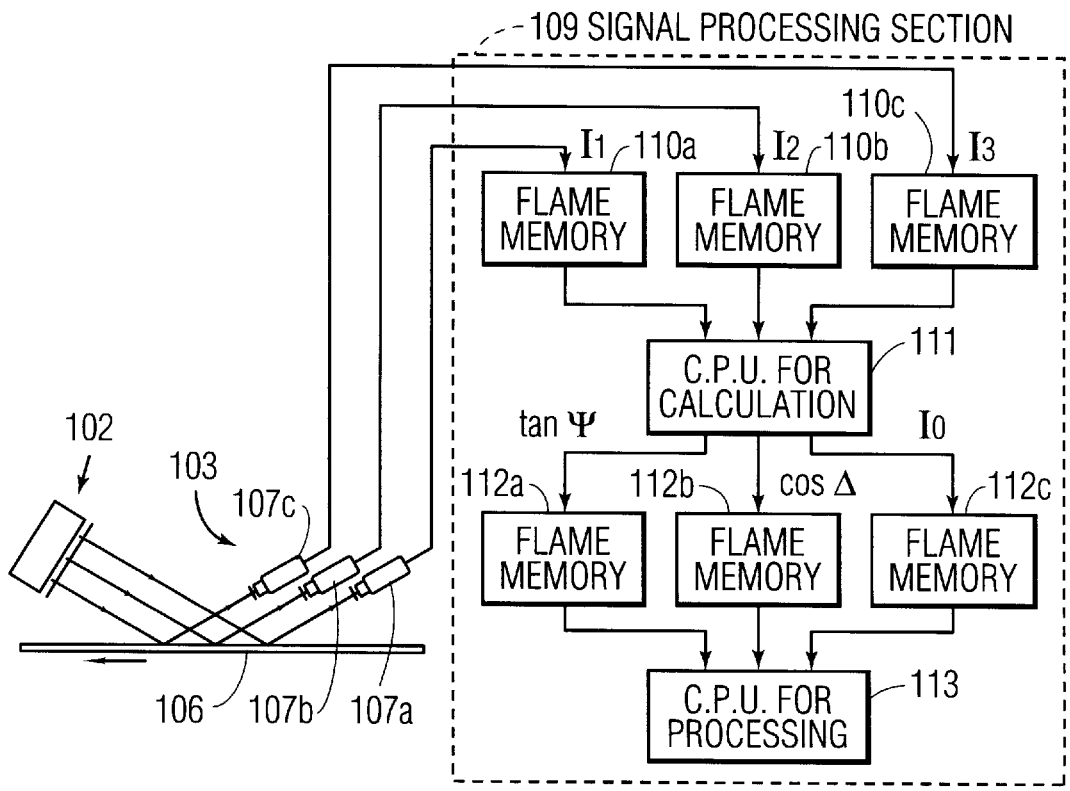
FIG. 12 is a block diagram showing a signal processing section in the embodiment of FIG. 11.
Figure 13:
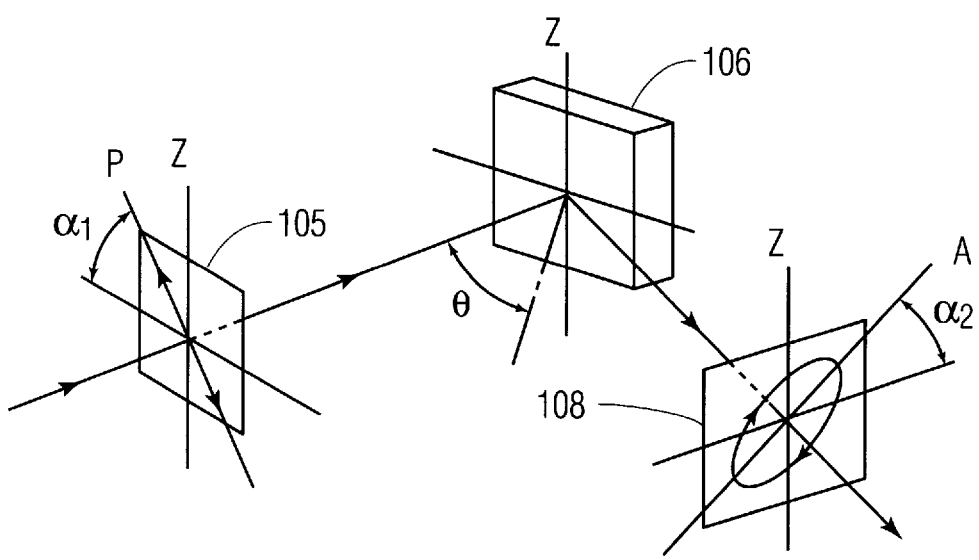
FIG. 13 is an explanatory view showing the operation principle of the embodiment of FIG. 11.

FIGS. 11 and 12 show an arrangement of the surface flaw detecting apparatus according to this embodiment. FIG. 11 is a layout view of an optical system and FIG. 12 is a block diagram showing the signal processing section. As shown in FIG. 11, an optical system 101 comprises a light irradiating section 102 and a light receiving section 103. The light irradiating section 102 has a parallel light source 104 and a polarizer 105 disposed in front of the parallel light source 104. The parallel light source 104 comprises a planar light source which is formed to extend in the direction of width of a product to be inspected, e.g., a steel plate 106, and irradiates light of parallel flux to the surface of the steel plate 106 over a certain length. The polarizer 105 comprises, e.g., a polarizing plate or filter and, as shown in FIG. 13, it is arranged such that an angle $\alpha_1$ formed between the transmission axis P of the polarizer and the incident plane on the steel plate 106 is π/4. The light receiving section 103 comprises three line sensor cameras 107a, 107b, 107c and three analyzers 108a, 108b, 108c disposed in front of light receiving surfaces of the line sensor cameras 107a, 107b, 107c. The line sensor cameras 107a, 107b, 107c are arranged at respective positions shifted from each other in the moving direction of the steel plate 106, and detect the reflected light from the surface of the steel plate 106 for conversion into polarization image signals. The analyzers 108a, 108b, 108c each comprise, e.g., a polarizing plate or filter and, as shown in FIG. 13, they are arranged such that an angle $\alpha_2$ formed between the transmission axis A of each analyzer 108 and the incident plane on the steel plate 106 is 0 for the analyzer 108a, π/4 for the analyzer 108b, and −π/4 for the analyzer 108c.

A signal processing section 109 comprises frame memories 110a, 110b, 110c for storing polarization images, frame memories 112a, 112b, 112c for storing ellipso-parameter images, and a CPU 113 for processing. The polarization image signals output from the line sensor cameras 107a, 107b, 107c are two-dimensionally developed in the frame memories 110a, 110b, 110c, respectively. A CPU 111 for calculation reads the polarization image signals for the same position on the steel plate 106 from the frame memories 110a, 110b, 110c, taking into account shifts in set positions of the line sensor cameras 107a, 107b, 107c, calculates polarization parameters for respective corresponding pixels, i.e., an amplitude reflectance ratio tan Ψ, cos Δ indicative of the phase difference Δ and the intensity $I_0$ of the reflected light from the surface of the steel plate 106, and then produces images of the polarization parameters, i.e., a tan Ψ image, a cos Δ image and an $I_0$ image. The tan Ψ image, the cos Δ image and the $I_0$ image calculated by the CPU 111 for calculation are two-dimensionally developed in the frame memories 112a, 112b, 112c, respectively. The CPU 113 for processing determines the type of the flaw from bright and dark patterns of the tan Ψ, cos Δ and $I_0$ images in the abnormal portion developed in the frame memories 112a, 112b and 112c and also determines the extent of the flaw from the degree of luminance change in the $I_0$ image developed in the frame memory 110c.

Prior to describing the operation of the surface flaw detecting apparatus thus arranged, the principles for calculating the amplitude reflectance ratio tan Ψ, cos Δ and the intensity $I_0$ of the reflected light from the surface of the steel plate 106 based on the light intensities detected by the three line sensor cameras 107a, 107b, 107c will first be described.

Assuming that, as shown in FIG. 13, the angles formed between the transmission axis P of the polarizer 105 and the transmission axis A of each analyzer 108 and the incident plane on the steel plate 106 are $\alpha_1$ and $\alpha_2$, respectively, when a P-polarized light component and an S-polarized light component impinge upon the steel plate 106 at an arbitrary incident angle i and are reflected by the plate surface, the light intensity $I(\alpha_1, \alpha_2)$ of a resultant of the two components after passing through the analyzer 108 is expressed below, given amplitude reflectances of the P- and S-components being $r_P$ and $r_S$, respectively:

$$I(\alpha_1, \alpha_2) = |E_0 \cos\alpha_1 \cdot r_P \cos\alpha_2 + E_0 \sin\alpha_1 \cdot r_s \sin\alpha_2|^2$$
$$= 2I_0[\rho^2 \cos^2\alpha_1 \cdot \cos^2\alpha_2 + \sin^2\alpha_1 \cdot \sin^2\alpha_2 +$$
$$(1/2)\rho\sin2\alpha_1 \cdot \sin2\alpha_2 \cdot \cos\Delta]$$

where $$I_0 = |E_0|^2 \cdot R_s/2, \quad r_P = \sqrt{R_P} \cdot \exp(i\phi_P),$$

$$r_s = \sqrt{R_s} \cdot \exp(i\phi_s), \quad \rho = \sqrt{R_P} / \sqrt{R_s} = \tan\Psi,$$

and $\Delta = \phi_s - \phi_P$

Assuming now $\alpha_1 = \pi/4$, the light intensity $I_1$ passing through the analyzer 108a of $\alpha_2 = 0$ is given by $I_1 = I_0\rho^2$, the light intensity $I_2$ passing through the analyzer 108b of $\alpha_2 = \pi/4$ is given by $I_2 = I_0(1 + \rho^2 + 2\rho\cos\Delta)/2$, and the light intensity $I_3$ passing through the analyzer 108c of $\alpha_2 = -\pi/4$ is given by $I_3 = I_0(1 + \rho^2 - 2\rho\cos\Delta)/2$. From these light intensities $I_1$, $I_2$ and $I_3$, tan Ψ, cos Δ and the reflected light intensity $I_0$ are calculated as follows:

$$\tan\Psi = \sqrt{\frac{I_1}{I_2 + I_3 - I_1}}$$

$$\cos\Delta = \frac{I_2 - I_3}{2I_1} \tan\Psi$$

$$I_0 = I_2 + I_3 - I_1$$

Note that any of the light intensities $I_1$, $I_2$ and $I_3$ may be multiplieda constant depending on selection of amplifier gains of the cameras.

The operation of the apparatus for detecting flaws on the steel plate 106 by using tan Ψ, cos Δ and the reflected light intensity $I_0$ thus calculated will be described below with reference to FIGS. 14(a) to 14(c). In the optical system 101, the polarized light irradiated to the steel plate 106 moving at a constant speed is reflected by the plate surface at positions with predetermined intervals L therebetween and enters the line sensor cameras 107a, 107b, 107c through the analyzers 108a, 108b, 108c successively. In other words, an image on the same detected line is detected with small time difference corresponding to the interval L. When the line sensor cameras 107a, 107b, 107c detect the intensity of the reflected light coming from the steel plate 106, the line sensor camera 107a detects the light intensity $I_1$ as the analyzer 108a of $\alpha_2 = 0$ is disposed in front of the camera 107a, the line sensor camera 107b detects the light intensity $I_2$ as the analyzer 108b of $\alpha_2 = \pi/4$ is disposed in front of the camera 107b, and the line sensor camera 107c detects the light intensity $I_3$ as the analyzer 108c of $\alpha_2=\pi/4$ is disposed in front of the camera 107c. Images representing distributions of the light intensities $I_1$, $I_2$, $I_3$ detected by the line sensor cameras 107a, 107b, 107c are two-dimensionally developed in the frame memories 110a, 110b, 110c, respectively. When the line sensor cameras 107a, 107b, 107c detect the light intensities $I_1$, $I_2$, $I_3$ in such a way, the light intensity $I_1$ entering the line sensor camera 107a through the analyzer 108a of $\alpha_2=0$ is approximately twice the light intensities $I_2$, $I_3$ entering the line sensor cameras 107b, 107c. By setting the sensitivity of the line sensor camera 107a to ½ of the sensitivity of the line sensor cameras 107b, 107c, therefore, the images can be produced in the frame memories 110a, 110b, 110c with substantially the same density level as a reference.

The CPU 111 for calculation reads the polarization image signals representing the light intensities $I_1$, $I_2$, $I_3$ produced in the frame memories 110a, 110b, 110c, taking into account shifts in set positions of the line sensor cameras 107a, 107b, 107c. Further, the CPU 111 calculates the amplitude reflectance ratio tan $\Psi$, cos $\Delta$ indicative of the phase difference $\Delta$ and the intensity $I_0$ of the reflected light from the surface of the steel plate 106 for respective corresponding pixels, and then produces a tan $\Psi$ image in the frame memory 112a, a cos $\Delta$ image in the frame memory 112b and an $I_0$ image in the frame memory 112c. When producing the images, tan $\Psi=0-$ approximately 2 is converted into gradations 0 to 255 and cos $\Delta=-1$ to 1 is converted into gradations 0 to 255 for respective corresponding pixels. For example, assuming that a normal portion is represented by cos $\Delta=0$ and an abnormal portion is represented by cos $\Delta=-1$, the abnormal portion is formed in the cos $\Delta$ image with higher density than the normal portion. Incidentally, when the sensitivity of the line sensor camera 107a is set to ½ of the sensitivity of the line sensor cameras 107b, 107c, the amplitude reflectance ratio tan $\Psi$, cos $\Delta$ indicative of the phase difference $\Delta$ and the intensity $I_0$ of the reflected light from the surface of the steel plate 106 are calculated as follows:

$$\tan\Psi = \sqrt{\frac{I_1}{I_2+I_3-I_1}}$$

$$\cos\Delta = \frac{I_2-I_3}{2I_1}\tan\Psi$$

$$I_0 = I_2 + I_3 - I_1$$

In the CPU 113 for processing, the density of each pixel of the tan $\Psi$ image, the cos $\Delta$ image and the $I_0$ image produced in the frame memories 112a, 112b, 112c is subjected to shading compensation and then normalized with the density of the normal portion as a reference for conversion into a density level characteristic. The CPU determines the type and extent of the abnormal portion from change in the density level characteristics of the tan $\Psi$ image, the cos $\Delta$ image and the $I_0$ image.

Figure 14A:
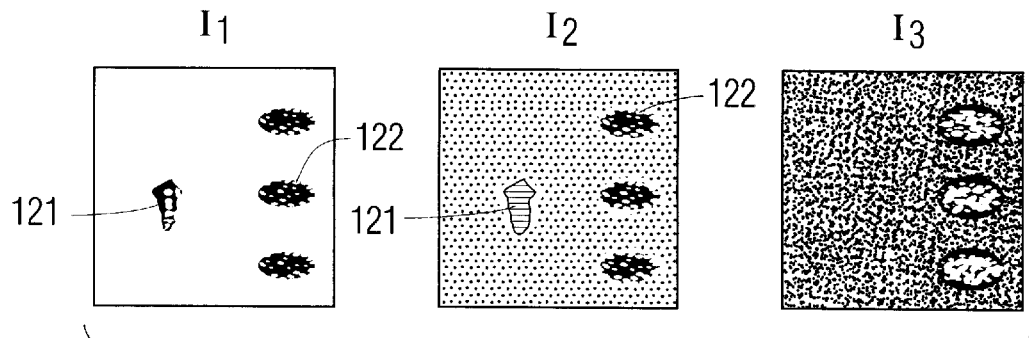
FIGS. 14(a) to 14(c) are image distribution characteristic views showing the operation of the embodiment of FIG. 11.
Figure 14B:
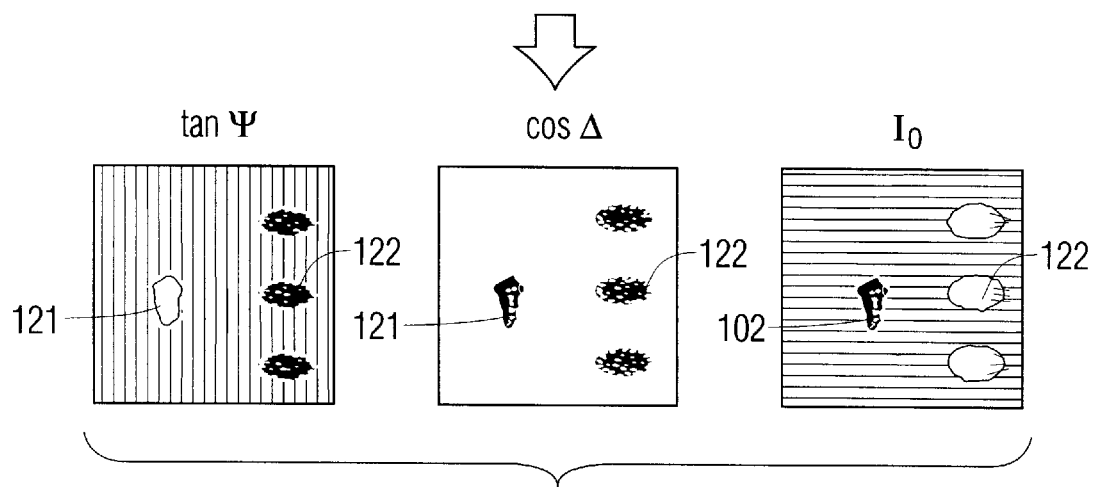
Figure 14C:
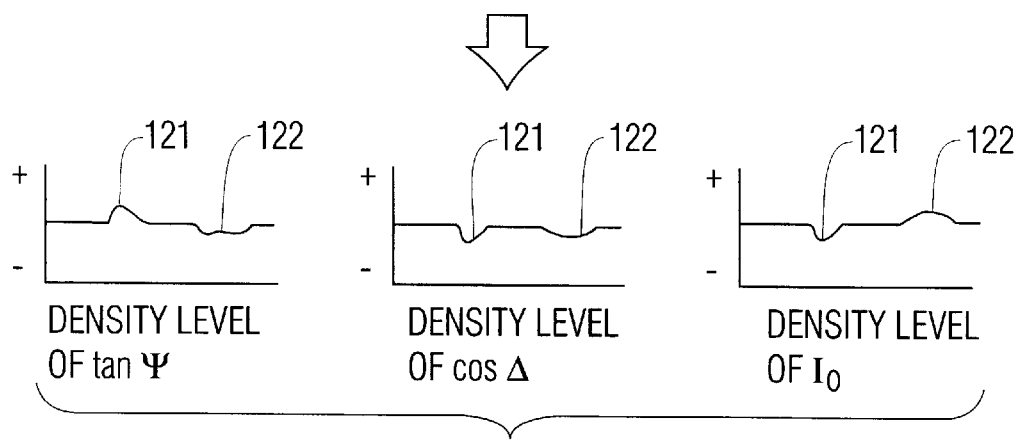

By way of example, FIG. 14(a) shows images obtained by irradiating polarized light thlollgll the light irradiating section 102 to the steel plate 106 moving at a speed of 300 m/minute at an incident angle of 60 degrees, detecting the light intensities $I_1$, $I_2$, $I_3$ by the line sensor cameras 107a, 107b, 107c with intervals L between inspection lines of 100 mm, and developing distributions of the light intensities in the frame memories 110a, 110b, 110c. FIG. 14(b) shows the tan $\Psi$ image, the cos $\Delta$ image and the $I_0$ image calculated by the CPU 111 for calculation from the polarized light images of the light intensities $I_1$, $I_2$, $I_3$ developed in the frame memories 110a, 110b, 110c. In the images of FIGS. 14(a) and 14(b), a portion 121 substantially at the center of the image where the light intensity is changed represents a flaw in the form of surface irregularities, and portion 122 in the right-hand side of the image where the light intensity is also changed represent patterned flaws such as oil stains. As seen from FIG. 14(b), the densities of the tan $\Psi$ image, the cos $\Delta$ image and the $I_0$ image are apparently different between the normal portion occupying a most part of the image and the remaining abnormal portions. In the cos $\Delta$ image shown in FIG. 14(b), for example, the abnormal portions are much darker than the normal portion. FIG. 14(c) shows density level characteristics resulted by normalizing the density of each pixel of the tan $\Psi$ image, the cos $\Delta$ image and the $I_0$ image with the density of the normal portion as a reference. As seen from FIG. 14(c), the density level of the tan $\Psi$ image of the irregularity flaw 121 is raised to the positive side, the density level of the cos $\Delta$ image thereof is dropped to the negative side and the density level of the $I_0$ image thereof is dropped to the negative. On the other hand, for the patterned flaws 122 such as oil stains, the density levels of the tan $\Psi$ image and the cos $\Delta$ image are both dropped to the negative side, and the density level of the $I_0$ image is raised to the positive. Accordingly, the flaw type can be determined from bright and dark patterns of the tan $\Psi$, cos $\Delta$ and $I_0$ images. Further, the extent of the flaw can be determined from the degree of change in the density level of these images.

Figure 15:
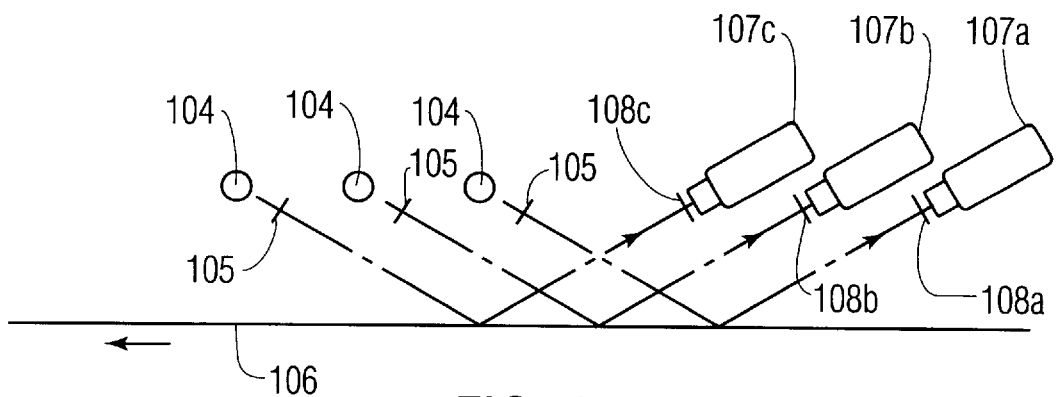
FIG. 15 is a side view showing an optical system in another embodiment.

In the illustrated embodiment, the light source 104 of the light irradiating section 102 comprises a single planar light source. As shown in a side view of FIG. 15, however, three linear light sources 104a, 104b, 104c may be disposed with predetermined intervals therebetween corresponding to the three line sensor cameras 107a, 107b, 107c. In this case, polarized lights emitted from the linear light sources 104a, 104b, 104c and reflected by the surface of the steel plate 106 are received by the corresponding line sensor cameras 107a, 107b, 107c.

Figure 16:
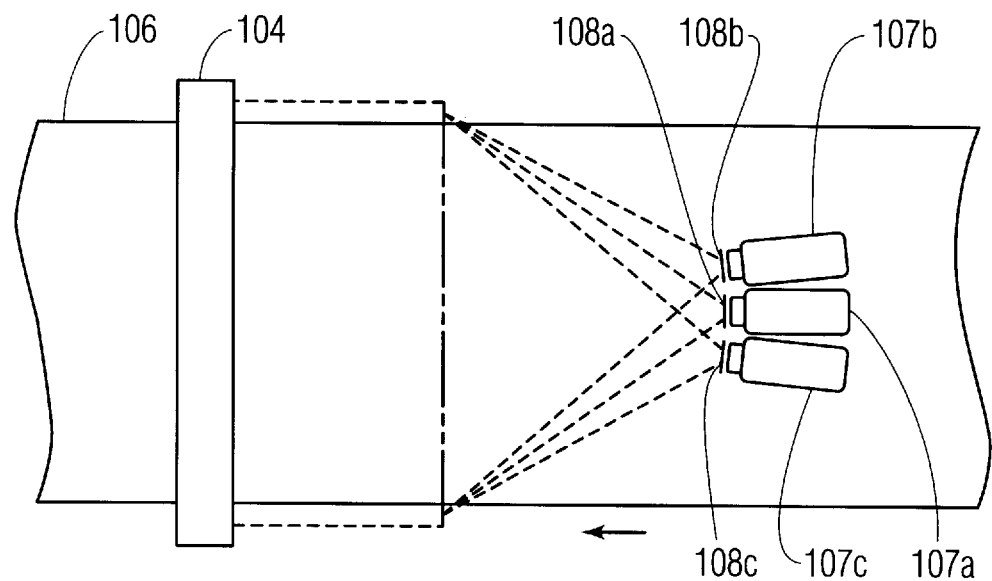
FIG. 16 is a plan view showing an optical system in another embodiment.
Figure 17:
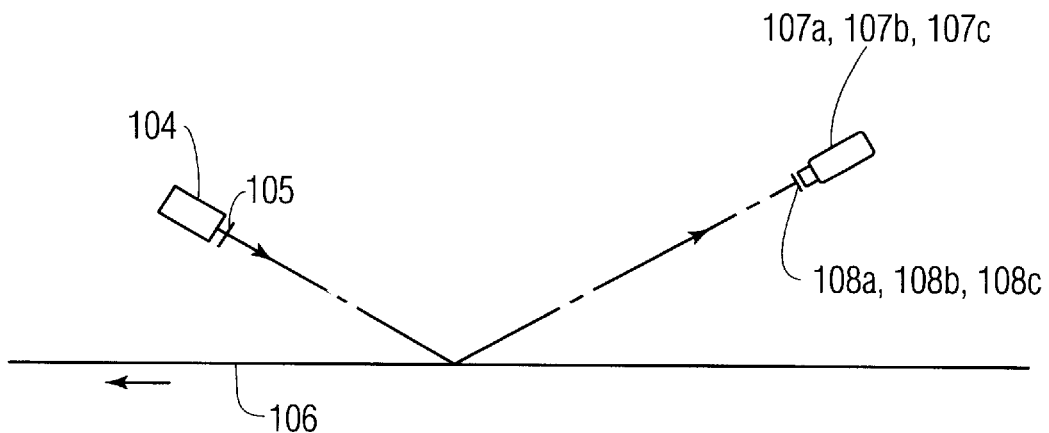
FIG. 17 is a side view showing the optical system in the embodiment of FIG. 16.

In the illustrated embodiment, the line sensor cameras 107a, 107b, 107c in the light receiving section 103 are disposed at positions shifted from each other in the moving direction of the steel plate 6. As shown in a plan view of FIG. 16 and a side view of FIG. 17, however, the line sensor cameras 107a, 107b, 107c may be disposed at the same height on a line perpendicular to the moving direction of the steel plate 6 so that the reflected light from the same position on the steel plate 106 is detected by the line sensor cameras 107a, 107b, 107c simultaneously. When there is an ample space, effects of the different depths of the field of view upon the images can be avoided by using lenses having the long focal length in the line sensor cameras 107a, 107b, 107c. Depending on situation, the line sensor cameras 107b, 107c on both sides of the line sensor camera 107a positioned at the middle may be inclined to face inwardly by a certain angle.

Figure 18:
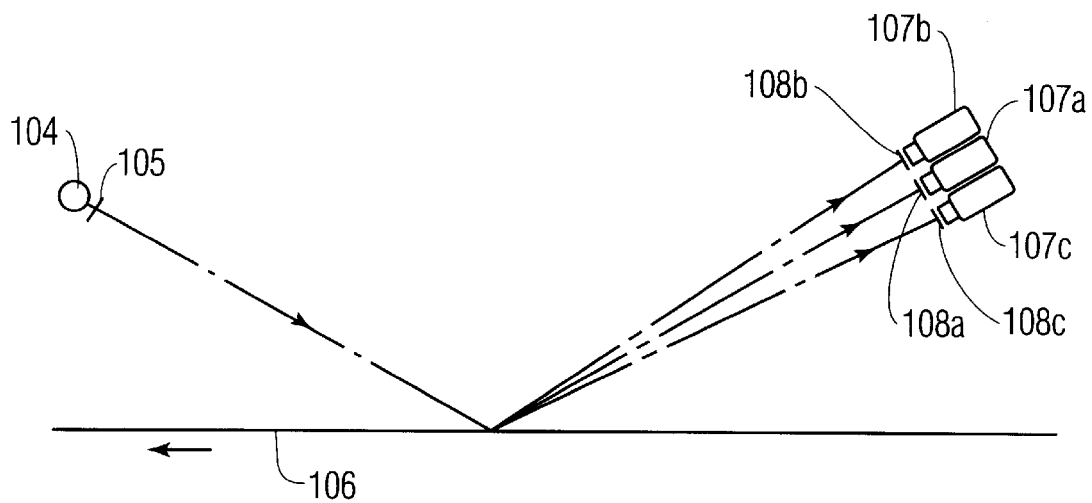
FIG. 18 is a side view showing an optical system in another embodiment.

In the above modification, the line sensor cameras 107a, 107b, 107c are disposed at the same height on a line perpendicular to the moving direction of the steel plate 106. As shown in FIG. 18, however, the line sensor cameras 107a, 107b, 107c may be disposed at different heights so as to detect the reflected light from the same position on the steel plate 106 simultaneously.

Figure 19:
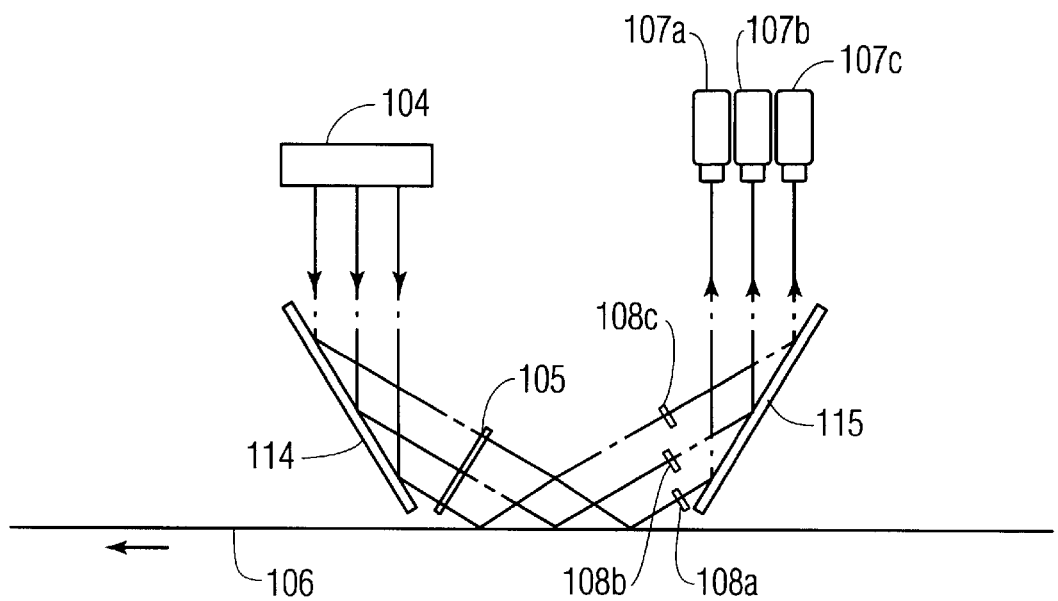
FIG. 19 is a side view showing the optical system in another embodiment.

In the foregoing embodiments, the polarized light emitted through the light irradiating section 102 is directly irradiated to the surface of the steel plate 106 and the reflected light therefrom is directly received by the line sensor cameras 107a, 107b, 107c, As shown in FIG. 19, however, the optical system may be modified such that light emitted from the parallel light source 104 perpendicularly to the surface of the steel plate 106 is first reflected by a mirror 114 and then irradiated to the surface of the steel plate 106 at an predetermined incident angle through the polarizer 105, and the reflected light therefrom is first reflected by a mirror 115 after passing through the analyzers 108a, 108b, 108c, and then received by the line sensor cameras 107a, 107b, 107c disposed perpendicularly to the surface of the steel plate 106. By so arranging the light irradiating section 102 and the light receiving section 103, an installation space necessary for the optical system can be reduced and the degree of freedom in design of the on-line system can be improved. In the above modification, the polarizer 105 is disposed downstream of the mirror 114 and the analyzers 108a, 108b, 108c are disposed upstream of the mirror 115 so that the polarized light is not affected by the mirrors 114, 115. As an alternative, however, the polarizer 105 may disposed upstream of the mirror 114 and the analyzers 108a, 108b, 108c are disposed downstream of the mirror 115 if the effects of the mirrors 114, 115 upon the polarized light is compensated.

While the foregoing embodiments are described as detecting line images of the surface of the steel plate 106 extending perpendicularly to the moving direction thereof by the line sensor cameras 107a, 107b, 107c, a two-dimensional CCD camera may be used to detect an image of the surface of the steel plate 106 over a certain length.

As described above, in the surface flaw detecting apparatus according to this Embodiment-2, polarized light in the form of parallel flux is irradiated to a surface to be inspected, three analyzers are arranged in different optical paths of reflected light from the inspected surface so as to have different azimuth angles, light intensity distributions of the polarized lights having passed through the analyzers are detected, polarization parameters, i.e., an amplitude reflectance ratio tan $\Psi$, cos $\Delta$ indicative of the phase difference $\Delta$ and the intensity $I_0$ of the reflected light from the inspected surface, for respective corresponding pixels of the images indicative of the detected light intensity distributions are calculated, images of the polarization parameters, i.e., a tan $\Psi$ image, a cos $\Delta$ image and an $I_0$ image are produced, the type of an abnormal portion is determined depending on whether bright and dark patterns of the produced tan $\Psi$ and cos $\Delta$ images in the abnormal portion coincide with each other or not, and the extent of abnormality is determined depending on the degree of luminance change in the $I_0$ image. As a result, flaws, oil stains, etc. on the inspected surface can be detected with high accuracy in a simple construction.

Also, since flaws and the like on the inspected surface can promptly be detected with no need of adjustment of the polarizing axis angle, etc., the surface of a sheet-like product continuously manufactured and fed can be inspected on-line.

EMBODIMENT-3

A surface flaw detecting apparatus according to a first aspect of this embodiment comprises a light irradiating section, a normally-reflected light detecting section (i.e., a light detecting section for detecting specularly reflected light), a scatteringly-reflected light detecting section, and a signal processing section. The light irradiating section irradiates polarized light to a surface to be inspected over its full width. The normally-reflected light detecting section is disposed in an optical path of normally-reflected light (i.e., specularly reflected light) of the reflected light from the inspected surface, and the scatteringly-reflected light detecting section is disposed in an optical path of scatteringly-reflected light of the reflected light from the inspected surface. At least one of the normally-reflected light detecting section and the scatteringly-reflected light detecting section comprises an optical system for separating the incoming light into three beams, analyzers disposed in respective optical paths of the separated three beams and having different azimuth angles from each other, and three image pickup means for receiving the beams (lights) having passed through the analyzers. The signal processing section compares image signals from the normally-reflected light detecting section and the scatteringly-reflected light detecting section, processes image signals from the three image pickup means receiving the lights having passed through the analyzers to calculate the two ellipso-parameters, i.e., the amplitude reflectance ratio tan $\Psi$ and cos $\Delta$ indicative of the phase difference $\Delta$, of the reflected light from the inspected surface, and evaluates characteristics of the inspected surface from the compared result between the normally-reflected light and the scatteringly-reflected light, as well as the two ellipso-parameters tan $\Psi$ and cos $\Delta$.

A surface flaw detecting apparatus according to a second aspect of this embodiment comprises a light irradiating section, a normally-reflected light detecting section and a scatteringly-reflected light detecting section which are the same used in the apparatus according to the first aspect. The signal processing section compares image signals from the normally-reflected light detecting section and the scatteringly-reflected light detecting section, processes image signals from the three image pickup means receiving the lights having passed through the analyzers to calculate the two ellipso-parameters, i.e., the amplitude reflectance ratio tan $\Psi$ and cos $\Delta$ indicative of the phase difference $\Delta$, of the reflected light from the inspected surface and the intensity $I_0$ of the reflected light from the inspected surface, and evaluates characteristics of the inspected surface from the compared result between the normally-reflected light and the scatteringly-reflected light, the two ellipso-parameters tan $\Psi$ and cos $\Delta$, as well as the reflected light intensity $I_0$.

A surface flaw detecting apparatus according to a third aspect of this embodiment comprises a light irradiating section, a light receiving section, and a signal processing section. The light irradiating section irradiates polarized light to a surface to be inspected over its full width. The light receiving section is disposed in an optical path of scatteringly-reflected light of the reflected light from the inspected surface, and comprises an optical system for separating the incoming light into three beams, analyzers disposed in respective optical paths of the separated three beams and having different azimuth angles from each other, and three image pickup means for receiving the beams (lights) having passed through the analyzers. The signal processing section processes image signals from the three image pickup means receiving the lights having passed through the analyzers to calculate the two ellipso-parameters, i.e., the amplitude reflectance ratio tan $\Psi$ and cos $\Delta$ indicative of the phase difference $\Delta$, of the reflected light from the inspected surface, and evaluates characteristics of the inspected surface from the two ellipso-parameters tan $\Psi$ and cos $\Delta$.

A surface flaw detecting apparatus according to a fourth aspect of this embodiment comprises a light irradiating section and a light receiving section which are the same used in the apparatus according to the third aspect. The signal processing section processes image signals from the three image pickup means receiving the lights having passed through the analyzers to calculate the two ellipso-parameters, i.e., the amplitude reflectance ratio tan $\Psi$ and cos $\Delta$ indicative of the phase difference $\Delta$, of the reflected light from the inspected surface and the intensity $I_0$ of the reflected light from the inspected surface, and evaluates characteristics of the inspected surface from the two ellipso-parameters tan $\Psi$ and cos $\Delta$, as well as the reflected light intensity $I_0$.

In this embodiment, the light irradiating section is arranged so as to irradiate polarized light to the inspected surface over its full width at a certain incident angle. The normally-reflected light detecting section for receiving normally-reflected light of the reflected light from the inspected surface and the scatteringly-reflected light detecting section for detecting scatteringly-reflected light of the reflected light from the inspected surface are disposed in the predetermined positions and connected at their outputs to the signal processing section. At least one of the normally-reflected light detecting section and the scatteringly-reflected light detecting section, for example, the former light detecting section comprises beam splitters for separating the incoming light into three beams, three image pickup means and three analyzers. The image pickup means each comprise, e.g., a CCD linear array camera. The analyzers are arranged between the beam splitters and the image pickup means such that they have different azimuth angles from each other, i.e., such that the angles formed between their transmission axes and the incident plane on the inspected surface are, e.g., 0, $\pi/4$ and $-\pi/4$. The three image pickup means receive polarized lights having passed through the respective analyzers and output image signals indicative of intensity distributions of the polarized lights.

The signal processing section compares the image signals of the normally-reflected light and the scatteringly-reflected light input respectively from the normally-reflected light detecting section and the scatteringly-reflected light detecting section to detect flaws such as a vertical crack on the inspected surface, and also process es the image signals from the three image pickup means receiving the lights having passed through the analyzers to calculate the two ellipso-parameters, i.e., the amplitude reflectance ratio tan $\Psi$ and cos $\Delta$ indicative of the phase difference $\Delta$, of the reflected light from the inspected surface, thereby detecting, from changes in the two ellipso-parameters tan $\Psi$ and cos $\Delta$, characteristic change of the inspected surface, i.e., the presence or absence of patterned flaws such as unevenness in physical property values of the inspected surface, unevenness in microscopic roughness, local presence of a thin oxide film or the like, and unevenness in thickness of a coating film.

Also the signal processing section calculates the intensity $I_0$ of the reflected light from the inspected surface along with the two ellipso-parameters tan $\Psi$ and cos $\Delta$, and detects characteristic change of the inspected surface from the two ellipso-parameters tan $\Psi$ and cos $\Delta$ and the reflected light intensity $I_0$, thereby inspecting the presence or absence of patterned flaws in more detail.

As an alternative, a light receiving section for detecting the scatteringly-reflected light of the reflected light from the inspected surface is provided as the reflected light detecting section. In a like manner to the above, the signal processing section detects characteristic change of the inspected surface from the two ellipso-parameters tan $\Psi$ and cos $\Delta$ of the scatteringly-reflected light from the inspected surface, or the two ellipso-parameters tan $\Psi$ and cos $\Delta$ and the reflected light intensity $I_0$ thereof, thereby inspecting the presence or absence of flaws in the form of surface irregularities with high accuracy.

Figure 20:
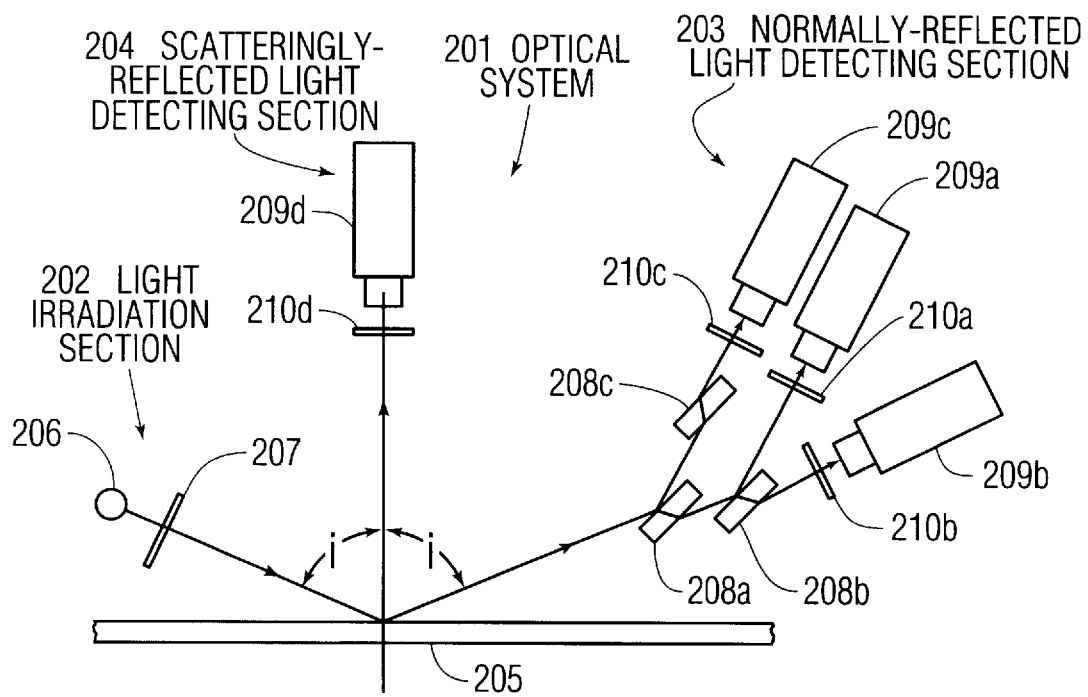
FIG. 20 is a layout view showing an optical system in an embodiment of the present invention.
Figure 21:
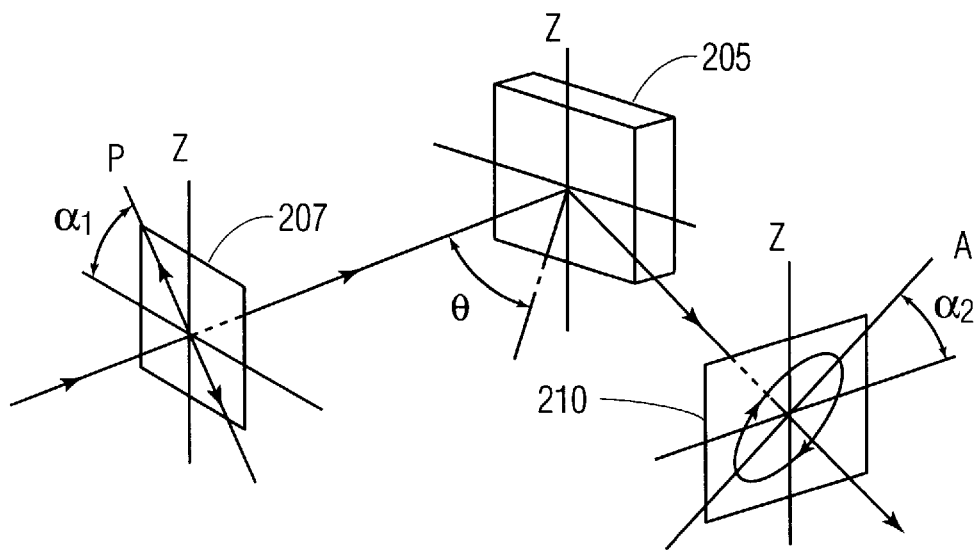
FIG. 21 is an explanatory view showing the operation principle of the optical system of FIG. 20.

FIG. 20 is a layout view of an optical system for use in the surface flaw detecting apparatus of this embodiment. As shown in FIG. 20, an optical system 101 comprises a light irradiating section 201, a normally-reflected light detecting section 203, and a scatteringly-reflected light detecting section 204. The light irradiating section 202 irradiates polarized light to the surface of a product to be inspected, e.g., a steel plate 205, over its full width at an incident angle i=60 degrees, for example. The light irradiating section 202 comprises a light source 206 and a polarizer 207 disposed in front of the light source 206. The light source 206 has the bar-like form to be capable of irradiating light over the full width of the inspected surface 205. The polarizer 207 comprises, e.g., a polarizing plate or filter and, as shown in an explanatory view of FIG. 21, it is arranged such that an angle $\alpha_1$ formed between the transmission axis P of the polarizer and the incident plane on the steel plate 205 is $\pi/4$. The normally-reflected light receiving section 203 receives light normally reflected from the steel plate 205 at a reflection angle i, and comprises beam splitters 208a, 208b, 208c each comprising a half mirror, for example, linear array cameras 209a, 209b, 209c each comprising a CCD camera, for example, and analyzers 210a, 210b, 210c disposed in front of light receiving surfaces of the linear array cameras 209a, 209b, 209c. Each camera is arranged so that the same position of the detection surface can be seen. The analyzers 210a, 210b, 210c each comprise, e.g., a polarizing plate or filter and, as shown in FIG. 21, they are arranged such that an angle $\alpha_2$ formed between the transmission axis A of each analyzer 210 and the incident plane on the steel plate 205 is 0 for the analyzer 210a, $\pi/4$ for the analyzer 210b, and $-\pi/4$ for the analyzer 210c. The scatteringly-reflected light receiving section 204 receives light scatteringly reflected from the steel plate 205 at a reflection angle of 0 degree, for example, and comprises a linear array camera 209d for scatteringly-reflected light and an analyzer 210d disposed in front of the linear array camera 209d for scatteringly-reflected light. The analyzer 210d also comprises, e.g., a polarizing plate or filter and is arranged such that the angle $\alpha_2$ formed between the transmission axis A of the analyzer and tile incident plane on the steel plate 205 is $\pi/2$.

Figure 22:
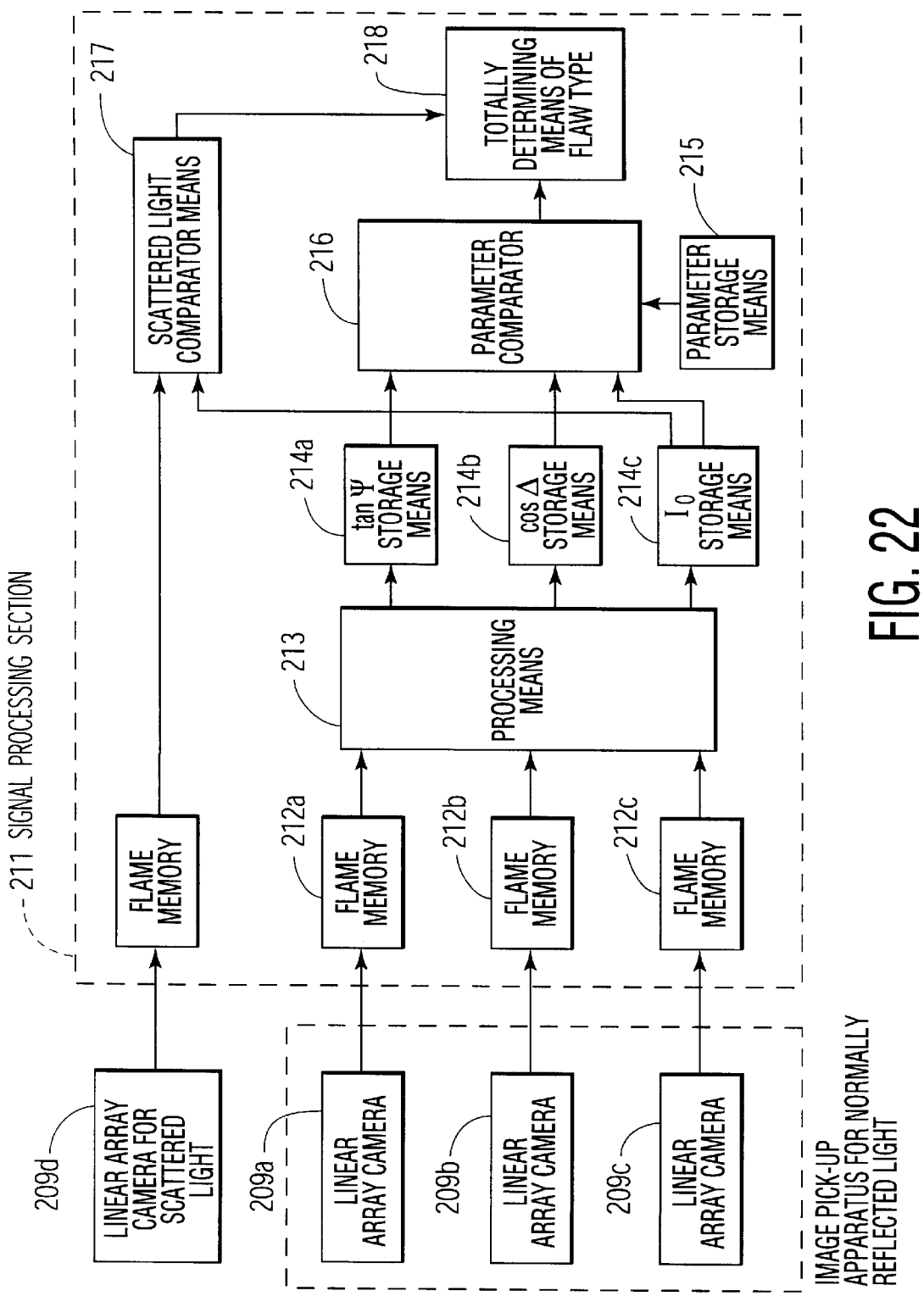
FIG. 22 is a block diagram showing the configuration of a signal processing section in the embodiment of FIG. 20.

As shown in a block diagram of FIG. 22, the linear array cameras 209a, 209b, 209c of the normally-reflected light detecting section 203 and the linear array camera 209d of the scatteringly-reflected light detecting section 204 are connected to a signal processing section 211. The signal processing section 211 comprises frame memories 212a, 212b, 212c for normally-reflected light, a frame memory 212d for scatteringly-reflected light, a CPU (processing means) 213, a tan $\Psi$ storage 214a, a cos $\Delta$ storage 214b, an $I_0$ storage 214c, a parameter storage 215, a parameter comparator 216, a scattered light comparator 217, totally determining means 218 of flaw type and output means which is not shown. Image signals output from the linear array cameras 209a, 209b, 209c are two-dimensionally developed in the frame memories 212a, 212b, 212c on a pixel-by-pixel basis, respectively. An image signal output from the linear array camera 209d for scatteringly reflected light is two-dimensionally developed in the frame memory 212d on a pixel-by-pixel basis. The CPU 213 reads the image signals for the same position on the steel plate 205 from the frame memories 212a, 212b, 212c successively, calculates the two ellipso-parameters, i.e., the amplitude reflectance ratio tan $\Psi$ and cos $\Delta$ indicative of the phase difference $\Delta$, and the intensity $I_0$ of the normally reflected light from the surface of the steel plate 205 for respective corresponding pixels, and then stores the calculated parameter values in the tan $\Psi$ storage 214a, the cos $\Delta$ storage 214b and the $I_0$ storage 214c. The parameter storage 215 stores various characteristic values of tan $\Psi$, cos $\Delta$ and the normally-reflected light intensity $I_0$ which have been determined beforehand and correspond to surface characteristics of the steel plate 205, i.e., patterned flaws such as unevenness in physical property values, unevenness in microscopic roughness, local presence of a thin oxide film or the like, and unevenness in thickness of a coating film. The parameter comparator 216 compares the values of tan $\Psi$, cos $\Delta$ and the normally-reflected light intensity $I_0$ stored respectively in the tan $\Psi$ storage 214a, the cos $\Delta$ storage 214b and the $I_0$ storage 214c with the characteristic values stored in the parameter storage 215 for each pixel, thereby determining the presence or absence of patterned flaws on the surface of the steel plate 205 and the type and extent thereof. The scattered light comparator 217 determines the presence or absence of flaws such as a vertical crack on the surface of the steel plate 205 and the extent thereof based on the normally-reflected light intensity $I_0$ with the scattered light intensity $I_4$. And total determination of the flaw type is performed finally by the totally determining means 218 of the flaw type.

Prior to describing the operation of the surface flaw detecting apparatus thus arranged, the principles for calculating the amplitude reflectance ratio tan $\Psi$, cos $\Delta$ and the intensity $I_0$ of the normally-reflected light from the surface of the steel plate 205 based on the light intensities detected by the three linear array cameras 209a, 209b, 209c will first be described.

Assuming that, as shown in FIG. 21, the angles formed between the transmission axis P of the polarizer 207 and the transmission axis A of each analyzer 210 and the incident plane on the steel plate 205 are $\alpha_1$ and $\alpha_2$, respectively, when a P-polarized light component and an S-polarized light component impinge upon the steel plate 205 at an arbitrary incident angle i and are reflected by the plate surface, the light intensity $I(\alpha_1, \alpha_2)$ of a resultant of the two components after passing through the analyzer 210 is expressed below, given amplitude reflectances of the P- and S-components being $r_P$ and $r_S$, respectively:

$$I(\alpha_1, \alpha_2) = |E_0\cos\alpha_1 \cdot r_P\cos\alpha_2 + E_0\sin\alpha_1 \cdot r_S\sin\alpha_2|^2$$

$$= 2I_0[\rho^2\cos^2\alpha_1 \cdot \cos^2\alpha_2 + \sin^2\alpha_1 \cdot \sin^2\alpha_2 + (1/2)\rho\sin 2\alpha_1 \cdot \sin 2\alpha_2 \cdot \cos\Delta]$$

where $$I_0 = |E_0|^2 \cdot R_s/2, r_P = \sqrt{R_P} \cdot \exp(i\phi_P),$$

$$r_s = \sqrt{R_s} \cdot \exp(i\phi_s), \rho = \sqrt{R_P}/\sqrt{R_s} = \tan\Psi,$$

and $\Delta = \phi_s - \phi_p$

Assuming now $\alpha_1 = \pi/4$, the light intensity $I_1$ passing through the analyzer 210a of $\alpha_2 = 0$ is given by $I_1 = I_0\rho^2$, the light intensity $I_2$ passing through the analyzer 210b of $\alpha_2 = \pi/4$ is given by $I_2 = I_0(1+\rho^2+2\rho\cos\Delta)/2$, and the light intensity $I_3$ passing through the analyzer 210c of $\alpha_2 = -\pi/4$ is given by $I_3 = I_0(1+\rho^2 2\rho\cos\Delta)/2$. From these light intensities $I_1$, $I_2$ and $I_3$, tan $\Psi$, cos $\Delta$ and the reflected light intensity $I_0$ are calculated as follows:

$$\tan\Psi = \sqrt{\frac{I_1}{I_2 + I_3 - I_1}}$$

$$\cos\Delta = \frac{I_2 - I_3}{2I_1} \tan\Psi$$

$$I_0 = I_2 + I_3 - I_1$$

The operation of the apparatus for detecting flaws based on the above principles will be described below. The polarized light irradiated through the light irradiation section 202 to the steel plate 205 moving at a constant speed and normally reflected by the surface of the steel plate 205 enters the linear array cameras 209a, 209b, 209c through the analyzers 210a, 210b, 210c. When the linear array cameras 209a, 209b, 209c detect the intensity of the normally reflected light, the linear array cameras 209a detects the light intensity $I_1$ as the analyzer 210a of $\alpha_2 = 0$ is disposed in front of the camera 209a, the linear array camera 209b detects the light intensity $I_2$ as the analyzer 210b of $\alpha_2 = \pi/4$ is disposed in front of the camera 209b, and the linear array camera 209c detects the light intensity $I_3$ as the analyzer 210c of $\alpha_2 = -\pi/4$ is disposed in front of the camera 209c. Images representing distributions of the light intensities $I_1$, $I_2$, $I_3$ detected by the linear array cameras 209a, 209b, 209c are two-dimensionally developed in the frame memories 212a, 212b, 212c, respectively. At the same time, the intensity $I_4$ of the scattered light from the surface of the steel plate 205 detected by the linear array camera 209d is two-dimensionally developed in the frame memory 212d.

The CPU 213 sequentially reads the light intensities $I_1$, $I_2$, $I_3$ developed in the frame memories 212a, 212b, 212c for respective corresponding pixels, calculates the amplitude reflectance ratio tan $\Psi$, cos $\Delta$ and the intensity $I_0$ of the normally reflected light, and stores the calculated values in the tan $\Psi$ storage 214a, the cos $\Delta$ storage 214b and the $I_0$ storage 214c. The parameter comparator 216 compares the values of tan $\Psi$, cos $\Delta$ and the normally-reflected light intensity $I_0$ stored respectively in the tan $\Psi$ storage 214a, the cos $\Delta$ storage 214b and the $I_0$ storage 214c with the characteristic values stored in the parameter storage 215 beforehand for each pixel, thereby determining the presence or absence of patterned flaws on the surface of the steel plate 205 and the type and extent thereof. On the other hand, the scattered light comparator 217 compares the scattered light intensity $I_4$ stored in the frame memory 212d with the normally-reflected light intensity $I_0$ stored in the $I_0$ storage 214c, thereby determining the presence or absence of flaws in the form of irregularities, such as a vertical crack, on the surface of the steel plate 205 and the extent thereof. The determined results of the parameter comparator 216 and the scattered light comparator 217 are totally determined by the totally determining means 218 of the flaw type. The totally determined results are sequentially output to recording or display means (not shown) through the output means 218 to clearly indicate the presence or absence of abnormality on the surface of the steel plate 205.

Thus, since the apparatus of this embodiment simultaneously detects not only the presence or absence of patterned flaws on the surface of the steel plate 205 and the type and extent thereof, but also the presence or absence of flaws in the form of irregularities and the extent thereof, it is possible to promptly and accurately detect the presence or absence of abnormality on the surface of the steel plate 205. For example, as compared with the conventional case of not considering tan $\Psi$, cos $\Delta$ and the normally-reflected light intensity $I_0$, the detection accuracy of a light patterned flaw can be raised from about 70% to about 95%, and the detection accuracy of a light irregularity flaw can be raised from about 80% to about 99% or more.

Figure 23:
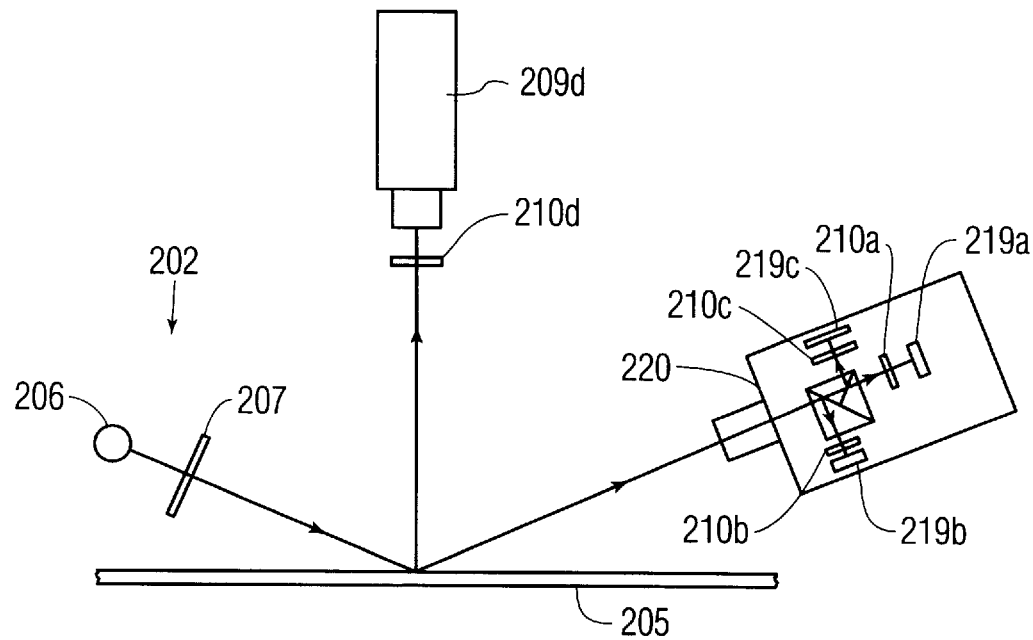
FIG. 23 is a layout view showing an optical system in another embodiment.

In the illustrated embodiment, the three linear array cameras 209a, 209b, 209c are provided in the normally-reflected light detecting section 203. As shown in FIG. 23, however, when the apparatus is modified so as to employ a three-plate type linear array camera 220 which incorporates one beam splitter 208, the three analyzers 210a, 210b, 210c, and three linear array cameras 219a, 219b, 219c, a patterned flaw and other various flaws on the surface of the steel plate 205 can also be detected as with the above embodiment. By so constructing the normally-reflected light detecting section 203 in a unitized structure, the degree of freedom in designing the installation space can be increased.

While the foregoing embodiment is described as providing the analyzer 210d in the scatteringly-reflected light detecting section 204, it is also possible to accurately detect irregularity flaws and patterned flaws on the surface of the steel plate 205 even if the polarizer 210d is omitted.

Figure 24:
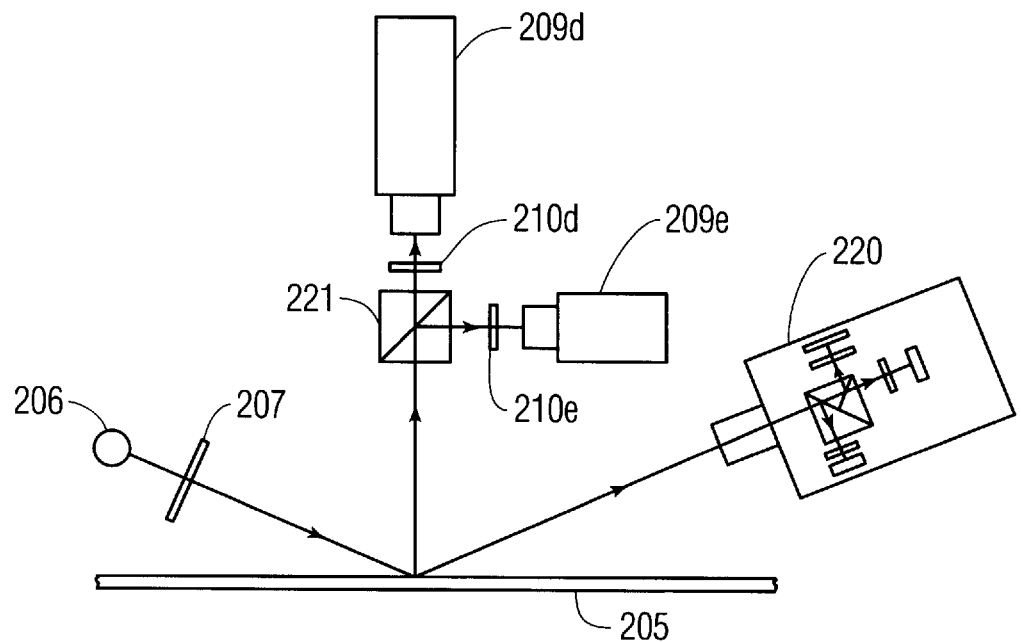
FIG. 24 is a layout view showing an optical system in another embodiment.

In the illustrated embodiment, one linear array camera 209d is provided in the scatteringly-reflected light detecting section 204. As shown in FIG. 24, however, the scatteringly-reflected light detecting section 204 may include, in addition to the analyzer 210d having the azimuth angle of $\pi/2$ and the linear array camera 209d for scatteringly-reflected light, an analyzer 210e having the azimuth angle of 0 and a linear array camera 209e for scatteringly-reflected light. In this case, the scatteringly reflected light is separated by a beam splitter 221 into two beams which are detected by the linear array cameras 209d, 209e for scatterintgly-reflected light, respectively. By so arranging the scatteringly-reflected light detecting section 204 as to detect both the intensity of the beam passing through the analyzer 210d having the azimuth angle of $\pi/2$ and the intensity of the beam passing through the analyzer 210e having the azimuth angle of 0, the detection accuracy of an irregularity flaw on the surface of the steel plate 205 can be improved to some extent in comparison with the foregoing embodiment.

Figure 25:
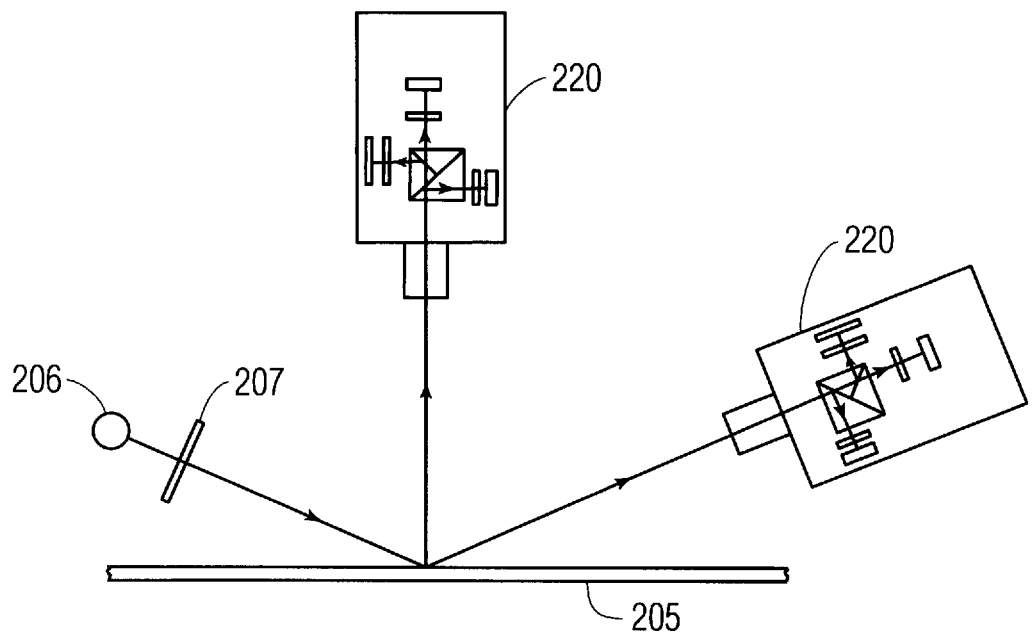
FIG. 25 is a layout view showing an optical system in another embodiment.

Alternatively, as shown in FIG. 25, the three-plate type linear array camera 220 incorporating the beam splitter 208, the three analyzers 210a, 210b, 210c, and the three linear array cameras 219a, 219b, 219c may be disposed in each of the scatteringly-reflected light detecting section 204 and the normally-reflected light detecting section 203. In this case, the two ellipso-parameters, i.e., tan $\Psi$ and cos $\Delta$, and the reflected light intensity $I_0$ can be measured for each of the scatteringly-reflected light and the normally-reflected light, enabling any types of flaws to be detected with high accuracy.

Figure 26:
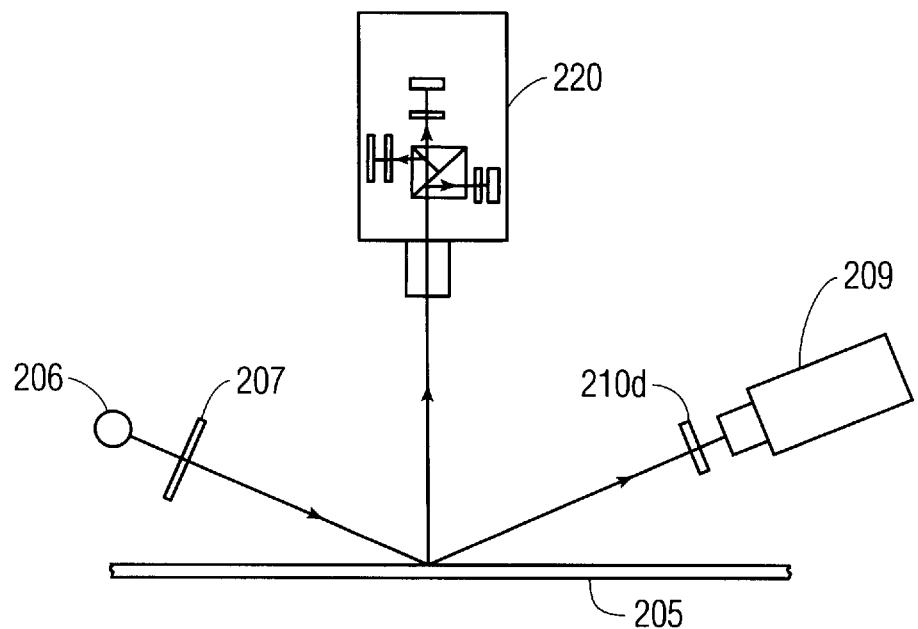
FIG. 26 is a layout view showing an optical system in another embodiment.
Figure 27:
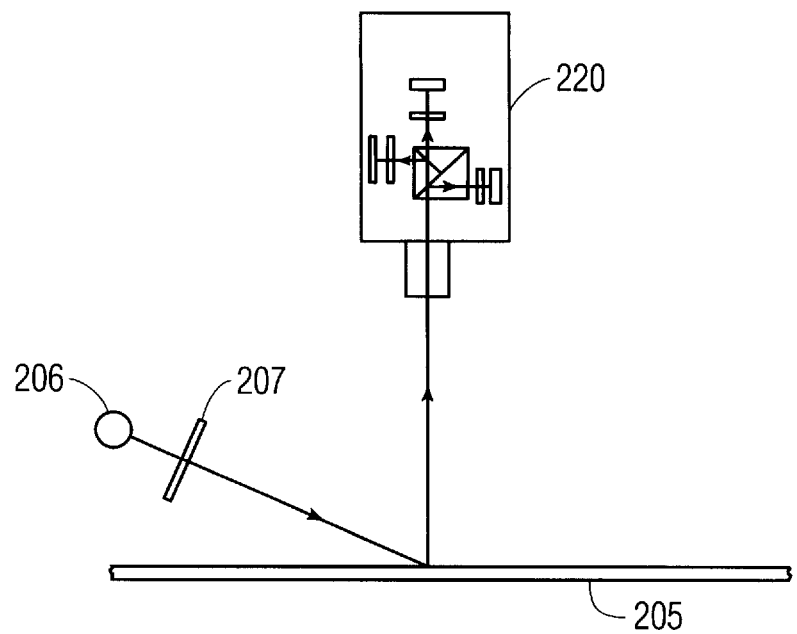
FIG. 27 is a layout view showing an optical system in another embodiment.

Further, when the apparatus is applied to mainly detect irregularity flaws on the surface of the steel plate 205 in a restricted field of applications, the optical system may be modified so as to include the three-plate type linear array camera 220 in the scatteringly-reflected light detecting section 204 and the analyzer 210d having the azimuth angle of $\pi/2$ and one linear array camera 209 in the normally-reflected light detecting section 203 as shown in FIG. 26, or include the three-plate type linear array camera 220 in the scatteringly-reflected light detecting section 204 alone as shown in FIG. 27. With these arrangements, the detection accuracy of such patterned flaws as having relatively small unevenness, but the detection accuracy of irregularity flaws can be increased by obtaining the two ellipso-parameters, i.e., tan $\Psi$ and cos $\Delta$, and the intensity $I_0$ of the scatteringly reflected light. Incidentally, the analyzer 210d having the azimuth angle of $\pi/2$ which is provided in the normally-reflected light detecting section 203 as shown in FIG. 26 is useful when oil is coated on the steel plate 205, but it may be dispensed with for steel plates not coated with oil.

While the foregoing embodiment is described as using the light source in the bar-like form, light from a laser beam source may condensed into the line form through a lens or a paraboloidal mirror for irradiation to the steel plate.

Further, in the foregoing embodiment, the presence of absence of patterned flaws and irregularity flaws on the surface of the steel plate 205 is detected from the two ellipso-parameters, i.e., tan $\Psi$ and cos $\Delta$, and the intensity $I_0$ of the reflected light, surface characteristics of the steel plate 205 may be detected from the ellipso-parameters tan $\Psi$ and cos $\Delta$ of the reflected light depending on the types of patterned flaws.

As described above, according to the surface flaw detecting apparatus of Embodiment-3, polarized light is irradiated to the inspected surface over its full width at a certain incident angle, normally-reflected light and scatteringly-reflected light from the inspected surface are detected, image signals of the normally-reflected light and the scatteringly-reflected light are compared with each other to detect flaws in the form of irregularities on the inspected surface, and the two ellipso-parameters, i.e., the amplitude reflectance ratio tan $\Psi$ and cos $\Delta$ indicative of the phase difference $\Delta$, of the reflected light from the inspected surface are calculated from at least one of the image signals of the normally-reflected light and the scatteringly-reflected light to detect, from changes in the two ellipso-parameters tan $\Psi$ and cos $\Delta$, the presence or absence of patterned flaws on the inspected surface. Therefore, the presence or absence of abnormality on the inspected surface can promptly be detected and the surface of a sheet-like product such as a steel plate can be inspected continuously on-line.

By calculating the intensity $I_0$ of the reflected light from the inspected surface along with the two ellipso-parameters tan $\Psi$ and cos $\Delta$ to detect characteristic change of the inspected surface from the two ellipso-parameters tan $\Psi$ and cos $\Delta$ and the reflected light intensity $I_0$, the presence or absence of various patterned flaws can be detected with higher accuracy.

Further, when the optical system is arranged so as to detect the two ellipso-parameters tan $\Psi$ and cos $\Delta$ of the scatteringly-reflected light from the inspected surface, or the two ellipso-parameters tan $\Psi$ and cos $\Delta$ and the reflected light intensity $I_0$ thereof to detect characteristic change of the inspected surface, the presence or absence of flaws in the form of irregularities on the inspected surface can be detected with high accuracy.

EMBODIMENT-4

A surface flaw detecting apparatus according to this embodiment comprises a light irradiating section, a three-plate type polarization linear array camera, and a signal processing section. The light irradiating section irradiates polarized light to a surface to be inspected. The three-plate type polarization linear array camera comprises a beam splitter for separating the incoming light into three beams, analyzers disposed in respective optical paths of the separated three beams and having azimuth angles of 0, $\pi/4$ and $-\pi/4$ and three linear array sensors for receiving the beams (lights) having passed through the analyzers. The linear array camera receives the reflected light from the inspected surface and outputs three different types of polarization image signals. The signal processing section processes polarization image signals output from the three-plate type polarization linear array camera, calculates the two ellipso-parameters, i.e., the amplitude reflectance ratio tan $\Psi$ and cos $\Delta$ indicative of the phase difference $\Delta$, and the intensity $I_0$ of the reflected light from the inspected surface, and determines the presence or absence of flaws on the inspected surface from the amplitude reflectance ratio tan $\Psi$, the phase difference $\Delta$ and the intensity $I_0$ of the reflected light calculated.

The surface flaw detecting apparatus of this embodiment comprises the light irradiating section, the three-plate type polarization linear array camera as a light receiving section, and the signal processing section. The light irradiating section has a light source arranged so as to irradiate emitted light to the inspected surface, e.g., the surface of a steel plate moving at a high speed, over its full width at a certain incident angle. A polarizer is disposed between the light source and the position on the inspected surface upon which the incident light impinges. The three-plate type polarization linear array camera receives the reflected light from the inspected surface and outputs three different types of polarization image signals. The linear array camera comprises a beam splitter, three analyzers and three linear array sensors each comprising, e.g., a CCD sensor. The beam splitter has two semi-transmissive reflecting surfaces which are each formed by laminating multilayer films of dielectrics on a light separating surface with vapor deposition. A first reflecting surface which receives the reflected light from the inspected surface is formed to have a 3:1 ratio of transmittance to reflectance, and a second reflecting surface which receives the light having passed through the first reflecting surface is formed to have a 1:1 ratio of transmittance to reflectance. The incoming light is separated by the beam splitter into three beams which are introduced to enter the respective analyzers. The three analyzers are arranged such that they have different azimuth angles from each other, i.e., such that the angles formed between their transmission axes and the incident plane on the inspected surface are 0, $\pi/4$ and $-\pi/4$. The three analyzers allow polarized lights having different polarizing planes from each other to enter the respective linear array sensors. The three linear array sensors receive the polarized lights having passed through the corresponding analyzers and output image signals representing intensity distributions of the respective polarized lights to the signal processing section. Since the reflected light from the inspected surface is received by one three-plate type polarization linear array camera within which the reflected light is separated into three beams having different polarizing planes from each other and the three beams are introduced to the three linear array cameras, the reflected light from the same position on the inspected surface can be introduced to the three linear array cameras at the same timing.

The signal processing section processes the polarization image signals output from the three-plate type polarization linear array camera, calculates the two ellipso-parameters, i.e., the amplitude reflectance ratio tan $\Psi$ and cos $\Delta$ indicative of the phase difference $\Delta$, and the intensity $I_0$ of the reflected light from the inspected surface, and compares the calculated amplitude reflectance ratio tan $\Psi$, phase difference $\Delta$ and intensity $I_0$ of the reflected light with characteristics of surface flaws which have been determined beforehand, thereby determining the degree of abnormality.

Figure 28:
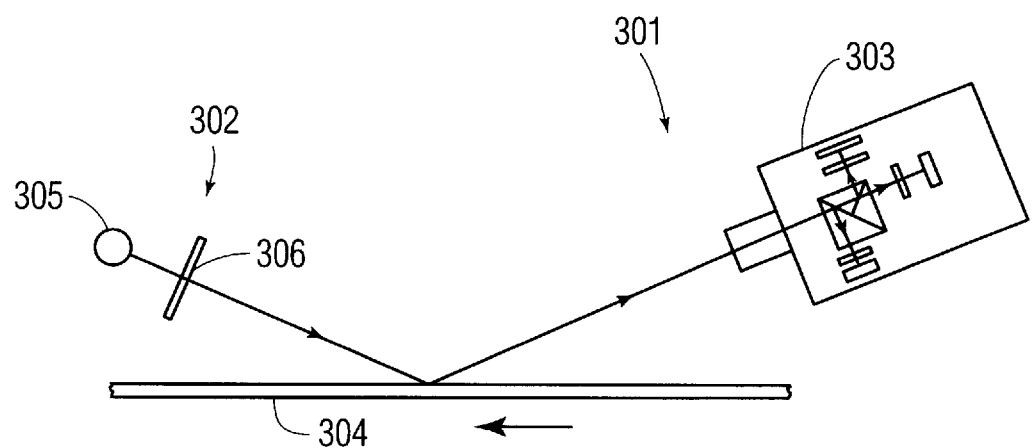
FIG. 28 is a layout view showing an optical system in an embodiment of the present invention.

FIG. 28 is a layout view of an optical system for use in the surface flaw detecting apparatus of this embodiment. As shown in FIG. 28, an optical system 301 comprises a light irradiating section 302 and a three-plate type polarization linear array camera 303. The light irradiating section 309 irradiates polarized light to the surface of a product to be inspected, e.g., a steel plate 304, at a certain incident angle. The light irradiating section 302 comprises a light source 305 and a polarizer 306 disposed in front of the light source 305. The light source 305 is formed of a bar-shaped light emitting device extending in the direction of width of the steel plate 304, and irradiates light over the full width of the steel plate 304. The polarizer 306 comprises, e.g., a polarizing plate or filter and, as shown in an explanatory view of FIG. 29, it is arranged such that an angle $\alpha_1$ formed between the transmission axis P of the polarizing plate and the incident plane on the steel plate 304 is $\pi/4$. As shown in a structural view of FIG. 30, the three-plate type polarization linear array camera 303 comprises a beam splitter 307, three analyzers 308a, 308b, 308c and three linear array sensors 309a, 309b, 309c. The beam splitter 307 consists of three prisms combined with each other so as to have two semi-transmissive reflecting surfaces which are each formed by laminating multilayer films of dielectrics on a light separating surface with vapor deposition. A first reflecting surface 307a which receives the reflected light from the steel plate 304 is formed to have a 3:1 ratio of transmittance to reflectance, and a second reflecting surface 307b which receives the light having passed through the first reflecting surface 307a is formed to have a 1:1 ratio of transmittance to reflectance. Thus, the beam splitter separates the reflected light from the steel plate 304 into three beams having the same light intensity. Incidentally, the optical path lengths from the incident surface of the beam splitter 307 to the respective emergent surfaces from which the separated three beams come out of the splitter are set to be the same. The analyzer 308a is disposed in an optical path of the light having passed through the second reflecting surface 307b and is oriented such that an azimuth angle $\alpha_2$, shown in FIG. 29, formed between the transmission axis A of the analyzer and the incident plane on the steel plate 304 is 0. The analyzer 308b is arranged in an optical path of the light reflected by the second reflecting surface 307b such that the azimuth angle $\alpha_2$ is $\pi/4$. The analyzer 308c is arranged in an optical path of the light reflected by the first reflecting surface 307a such that the azimuth angle $\alpha_2$ is $-\pi/4$. The linear array sensors 309a, 309b, 309c each comprise a CCD sensor, for example, and are disposed downstream of the analyzers 308a, 308b, 309c, respectively. Further, slits 310a, 310b, 310c for cutting off the light multi-reflected in the beam splitter 307 and useless scattered light are disposed between the beam splitter 307 and the analyzers 308a, 308b, 308c, respectively, and a lens group 311 disposed in front of the beam splitter 307. Gains of the linear array sensors 309a, 309b, 309c are adjusted so that all the sensors output signals of the same level when lights having the same intensity enter them.

Thus, with the above unitized structure that the analyzers 308a, 308b, 308 c and the linear array sensors 309a, 309b, 309c are provided in the respective optical paths of three beams branched by separating the incoming light, when the linear array sensors 309a, 309b, 309c, etc. are disposed near the feed pass of the steel plate 304 to detect the reflected light from the steel plate 304, position adjustment of the linear array sensors 309a, 309b, 309c, etc. is not necessary and the reflected light from the same position on the steel plate 304 can be detected by the three sensors at the same timing. Also, the three sets of linear array sensors 309a, 309b, 309c are all housed in one three-plate type polarization linear array camera 303 and the size of the entire detecting system is reduced. Therefore, the three-plate type polarization linear array camera 303 can easily be disposed in the optical path of the reflected light from the steel plate 304 and its mount position can optionally be selected, which increases the degree of freedom in design of the optical system 301.

Figure 31:
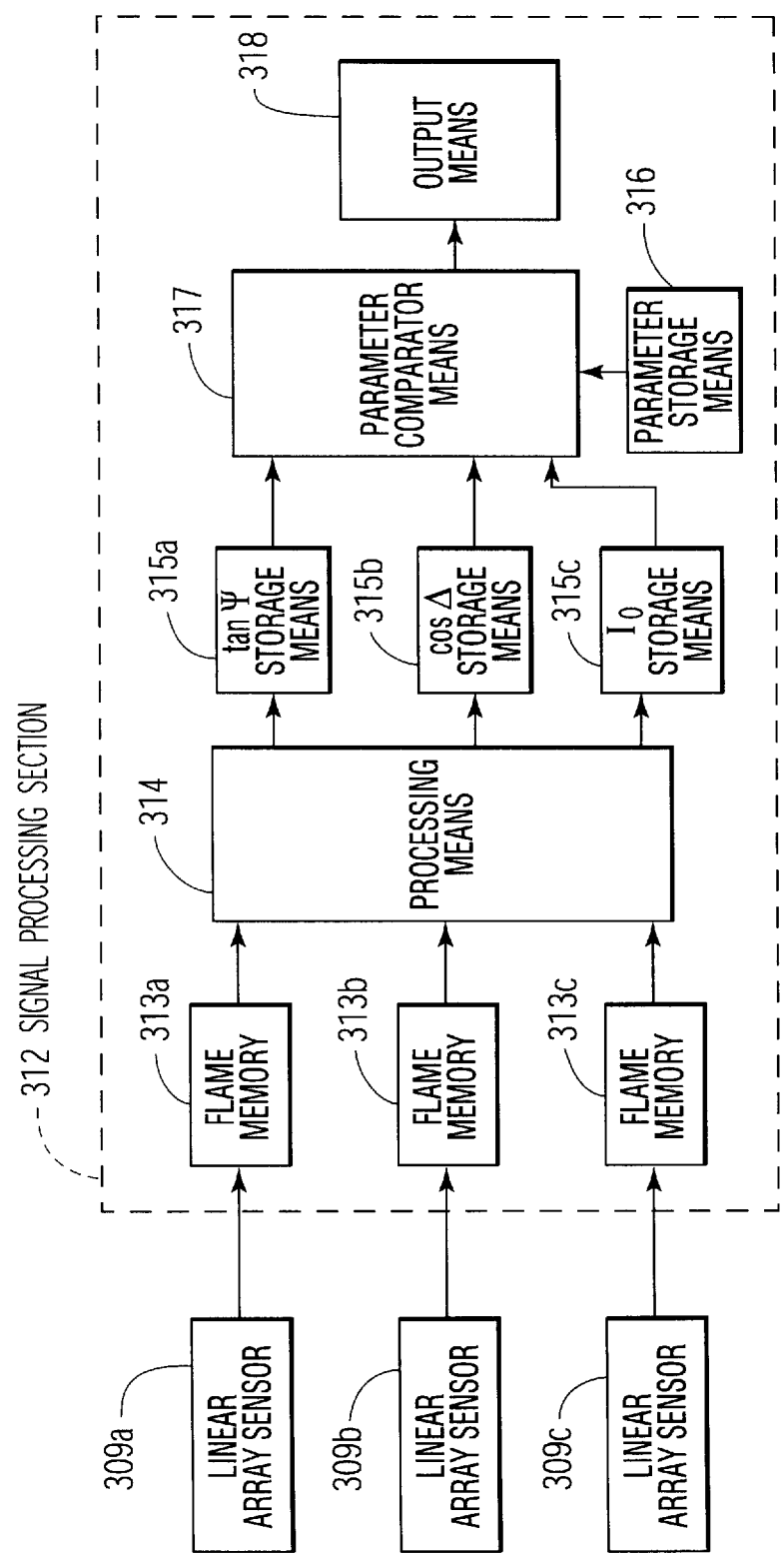
FIG. 31 is a block diagram showing a signal processing section in the embodiment of FIG. 28.

As shown in a block diagram of FIG. 31, the linear array sensors 309a, 309b, 309c of the three-plate type polarization linear array camera 303 are connected to a signal processing section 312. The signal processing section 312 comprises frame memories 313a, 313b, 313c, a CPU (processing means) 314, a tan $\Psi$ storage 315a, a cos $\Delta$ storage 315b, an $I_0$ storage 315c, a parameter storage 316, a parameter comparator 317, and output means 318. Image signals output from the linear array sensors 309a, 309b, 309c are two-dimensionally developed in the frame memories 313a, 313b, 313c on a pixel-by-pixel basis, respectively. The CPU 314 reads the image signals for the same position on the steel plate 304 from the frame memories 313a, 113b, 313c successively, calculates the two ellpso-parameters, i.e., the amplitude reflectance ratio tan Ψ and cos Δ indicative of the phase difference Δ, and the intensity $I_0$ of the reflected light from the surface of the steel plate 304 for respective corresponding pixels, and then stores the calculated parameter values in the tan Ψ storage 315a, the cos Δ storage 315b and the $I_0$ storage 315c. The parameter storage 316 stores various characteristic values of tan Ψ, cos Δ and the reflected light intensity $I_0$ which have been determined beforehand and correspond to surface characteristics of the steel plate 205, i.e., patterned flaws and irregularity flaws such as unevenness in physical property values, unevenness in microscopic roughness, local presence of a thin oxide film or the like, and unevenness in thickness of a coating film. The parameter comparator 317 compares the values of tan Ψ, cos Δ and the reflected light intensity $I_0$ stored respectively in the tan Ψ storage 315a, the cos Δ storage 315b and the $I_0$ storage 315c with the characteristic values stored in the parameter storage 316 for each pixel, thereby determining the presence or absence of patterned flaws and/or irregularity flaws on the surface of the steel plate 304 and the type and extent thereof.

Prior to describing the operation of the surface flaw detecting apparatus thus arranged, the principles for calculating the amplitude reflectance ratio tan Ψ, cos Δ and the intensity I of the reflected light from the surface of the steel plate 305 based on the light intensities detected by the three linear array sensors 309a, 309b, 309c will first be described.

Figure 29:
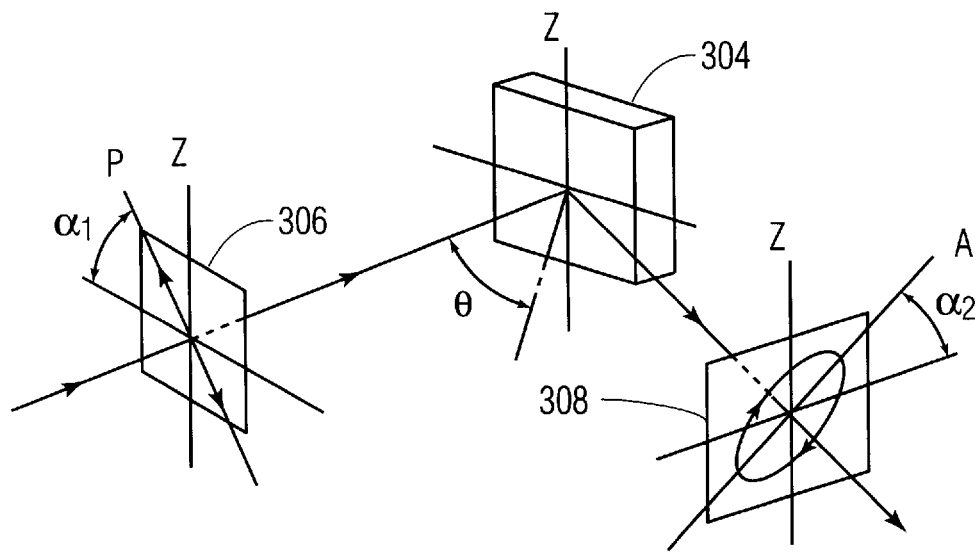
FIG. 29 is an explanatory view showing the operation principle of the optical system of FIG. 28.

Assuming that, in the case of the reflected light from the steel plate 304 entering each polarizer308 as shown in FIG. 29, the angles formed between the transmission axis P of the polarizing plate 306 and the transmission axis A of the analyzer 308 and the incident plane on the steel plate 304 are $\alpha_1$ and $\alpha_2$, respectively, when a P-polarized light component and an S-polarized light component impinge upon the steel plate 304 at an arbitrary incident angle i and are reflected by the plate surface, the light intensity $I(\alpha_1, \alpha_2)$ of a resultant of the two components after passing through the analyzer 308 is expressed below, given amplitude reflectances of the P- and S-components being $r_P$ and $r_S$, respectively:

$$I(\alpha_1, \alpha_2) = |E_0\cos\alpha_1 \cdot r_P\cos\alpha_2 + E_0\sin\alpha_1 \cdot r_S\sin\alpha_2|^2$$
$$= 2I_0[\rho^2\cos^2\alpha_1 \cdot \cos^2\alpha_2 + \sin^2\alpha_1 \cdot \sin^2\alpha_2 + (1/2)\rho\sin2\alpha_1 \cdot \sin2\alpha_2 \cdot \cos\Delta]$$

where $$I_0 = |E_0|^2 \cdot R_s/2, r_P = \sqrt{R_P} \cdot \exp(i\phi_P),$$

$$r_s = \sqrt{R_s} \cdot \exp(i\phi_s), \rho = \sqrt{R_P}/\sqrt{R_s} = \tan\Psi,$$

and $\Delta = \phi_s - \phi_p$

Assuming now $\alpha_1 = \pi/4$, the light intensity $I_1$ passing through the analyzer 308a of $\alpha_2 = 0$ is given by $I_1 = I_0\rho^2$, the light intensity $I_2$ passing through the analyzer 308b of $\alpha_2 = \pi/4$ is given by $I_2 = I_0(1+\rho^2+2\rho\cos\Delta)/2$, and the light intensity $I_3$ passing through the analyzer 308c of $\alpha_2 = -\pi/4$ is given by $I_3 = I_0(1+\rho^2-2\rho\cos\Delta)/2$. From these light intensities $I_1$, $I_2$ and $I_3$, tan Ψ, cos Δ and the reflected light intensity $I_0$ are calculated as follows:

$$\tan\Psi = \sqrt{\frac{I_1}{I_2 + I_3 - I_1}}$$

$$\cos\Delta = \frac{I_2 - I_3}{2I_1} \tan\Psi$$

$$I_o = I_2 + I_3 - I_1$$

Note that any of the light intensities $I_1$, $I_2$ and $I_3$ may be multiplieda constant depending on selection of amplifier gains of the cameras.

Figure 30:
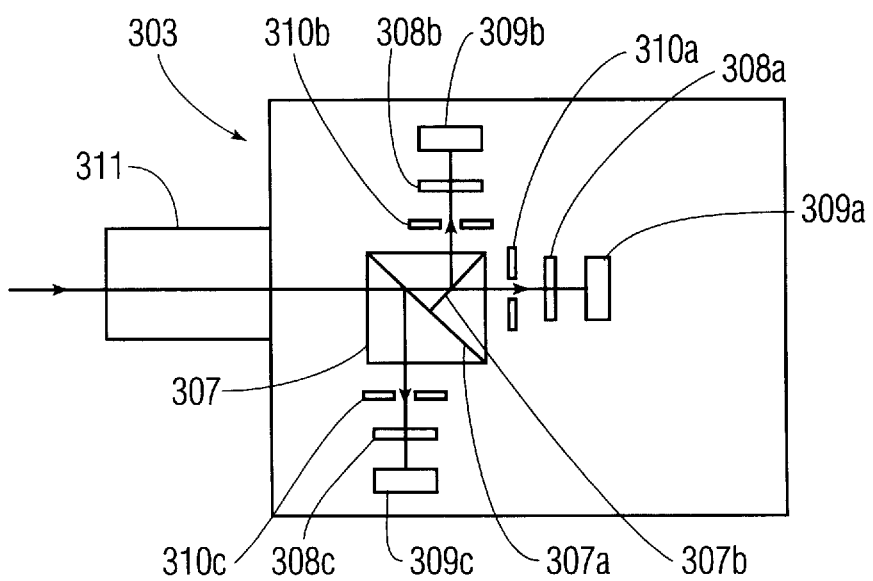
FIG. 30 is a view showing the configuration of a three-plate polarization linear array camera in the embodiment of FIG. 28.

In the above arrangement that the reflected light from the steel plate 304 is passed through the beam splitter 307 and then detected by the linear array sensors 309a, 309b, 309c through the analyzers 308a, 308b, 308c as shown in FIG. 30, assuming that the outputs of the linear array sensors 309a, 309b, 309c for the K-th pixel are $I_{1k}$, $I_{2k}$, $I^{3k}$, transmittance ratios of an S-polarized component to P-polarized component in the beam splitter 307 for the lights entering the linear array sensors 309b, 309c are τ2, τ3, and A=(τ2+τ3), B=(1+τ2²) and C=(1+τ3²) are given, the two ellipso-parameters tan Ψκ and cos Δκ for the K-th pixel and the reflected light intensity $I_{0k}$ representing the total light intensity of all the three K-th pixels are expressed below:

$$\tan\Psi_k = \sqrt{\frac{\tau 2 - \tau 3 - A - I_{1k}}{\tau 3 - B - I_{2k} + \tau 2 - C - I_{3k} - A - I_{1k}}}$$

$$\cos\Delta = \frac{\tau 3^2 - B - I_{2k} - \tau 2^2 - C - I_{3k} + (\tau 2^2 - \tau 3^2) - I_{1k}}{2 - \tau 2 - \tau 3 - A - I_{1k}} \times$$

$$\sqrt{\frac{\tau 2 - \tau 3 - A - I_{1k}}{\tau 3 - B - I_{2k} + \tau 2 - C - I_{3k} - A - I_{1k}}}$$

$$I_{0k} = \frac{\tau 3 - B - I_{2k} + \tau 2 - C - I_{3k} - A - I_{1k}}{\tau 2 - \tau 3 - A}$$

The operation of the apparatus for detecting flaws based on the above principles will be described below. The polarized light irradiated through the light irradiation section 302 to the steel plate 304 moving at a constant speed is reflected by the surface of the steel plate 304 and then received by the three-plate type polarization linear array camera 303. The reflected light from the steel plate 304 having entered the three-plate type polarization linear array camera 303 is separated by the beam splitter 307 into three beams which enter the linear array sensors 309a, 309b, 309c through the analyzers 308a, 308b, 308c. When the linear array sensors 309a, 309b, 309c detect the intensity of the reflected light, the linear array sensor 309a detects the light intensity $I_1$ as the analyzer 308a of $\alpha_2 = 0$ is disposed in front of the sensor 309a, the linear array sensor 309b detects the light intensity $I_2$ as the analyzer 308b of $\alpha_2 = \pi/4$ is disposed in front of the sensor 309b, and the linear array sensor 309c detects the light intensity $I_3$ as the analyzer 308c of $\alpha_2 = -\pi/4$ is disposed in front of the sensor 309c. Image signals representing the light intensities $I_1$, $I_2$, $I_3$ detected by the linear array sensors 309a, 309b, 309c are two-dimensionally developed in the frame memories 313a, 313b, 313c on pixel-by-pixel basis, respectively.

The CPU 314 sequentially reads the light intensities $I_1$, $I_2$, $I_3$ developed in the frame memories 313a, 313b, 313c for respective corresponding pixels, calculates the amplitude reflectance ratio tan $\Psi_k$, cos $\Delta_k$ and the intensity $I_{0k}$ of the reflected light, and stores the calculated values in the tan Ψ storage 315a, the cos Δ storage 315b and the $I_0$ storage 315c. The parameter comparator 317 compares the values of tan $\Psi_k$, cos $\Delta_k$ and the reflected light intensity $I_{0k}$ stored respectively in the tan Ψ storage 315a, the cos Δ storage 315b and the $I_0$ storage 315c with the characteristic values stored in the parameter storage 316 beforehand for each pixel, thereby determining the presence or absence of patterned flaws and/or irregularity flaws on the surface of the steel plate 304 and the type and extent thereof. The determined results of the parameter comparator 317 are sequentially output to recording or display means (not shown) through the output means 318 to clearly indicate the presence or absence of abnormality on the surface of the steel plate 304.

As described above, according to the surface flaw detecting apparatus of this embodiment, the three-plate type polarization linear array camera comprising three built-in linear array sensors, which receives the reflected light from the inspected surface and outputs three different types of polarization image signals, is used to provide the three different types of polarization image signals. Therefore, the three-plate type polarization linear array camera can easily be disposed in the optical path of the reflected light from the inspected surface and its mount position can optionally be selected, which increases the degree of freedom in design of the optical system in the surface flaw detecting apparatus utilizing polarization. Further, since the three linear array sensors are incorporated in one camera of unitized structure so that the reflected light from the same position on the inspected surface can be detected by the three sensors at the same time, the configuration of the signal processing section for processing image signals can be simplified and surface flaws on the inspected surface can be detected with high accuracy.

EMBODIMENT-5

A surface flaw detecting apparatus according to this embodiment comprises a light irradiating section, a light receiving section, and a signal processing section. The light irradiating section irradiates, to a surface to be inspected, polarized light being elongate in the direction width of the inspected surface. The light receiving section comprises three analyzers disposed in an optical path of the reflected light from the inspected surface and having different azimuth angles from each other, and three linear array sensors for receiving the lights having passed through the analyzers. Each of the linear array sensors receives the reflected light from the inspected surface and converts it into an image signal. The signal processing section normalizes and levels the image signals output from the linear array sensors, calculates relative values of the two ellipso-parameters, i.e., the amplitude reflectance ratio tan Ψ and cos Δ indicative of the phase difference Δ, and the intensity $I_0$ of the reflected light based on the normalized and leveled image signals, and determines the presence or absence of abnormality on the inspected surface from the calculated relative values of the amplitude reflectance ratio tan Ψ, the phase difference Δ and the reflected light intensity $I_0$.

In the surface flaw detecting apparatus of this embodiment, the light irradiating section is arranged so as to irradiate polarized light to the inspected surface over its full width at a certain incident angle, and the light receiving section is arranged so as to receive the reflected light from the inspected surface. The light receiving section includes a beam splitter for separating the incoming light into three beams, three sets of linear array cameras, each of which comprises, e.g., a CCD sensor, for receiving the separated three beams and outputting image signals, and three analyzers disposed between the beam splitter and the linear array cameras for converting the reflected light from the inspected surface into polarized lights having different oscillating planes from each other. The three analyzers are arranged such that they have different azimuth angles from each other, i.e., such that the angles formed between their transmission axes and the incident plane on the inspected surface are, e.g., 0, π/4 and −π/4.

The signal processing section normalizes and levels the image signals output from the linear array cameras such that the signal indicative of a normal portion represents the center luminance in the range of entire gradations, and converts the received image signals into image signals representing relative changes with respect to the normal portion. From these image signals representing relative changes with respect to the normal portion, the signal processing section calculates relative values of the two ellipso-parameters, i.e., the amplitude reflectance ratio tan Ψ and cos Δ indicative of the phase difference Δ, and the intensity $I_0$ of the reflected light, and produces relative value images of tan Ψ, cos Δ and $I_0$. From these relative value images of tan Ψ, cos Δ and $I_0$, the signal processing section detects relative changes in tan Ψ, cos Δ and $I_0$, thereby detecting the presence or absence of abnormality on the inspected surface of a steel plate or the like.

Figure 32:
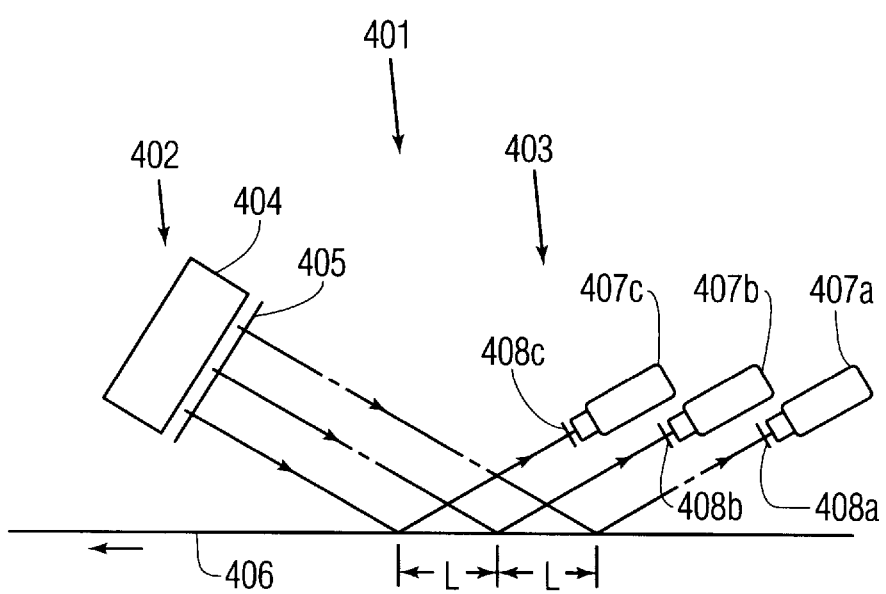
FIG. 32 is a layout view showing an optical system in an embodiment of the present invention.
Figure 33:
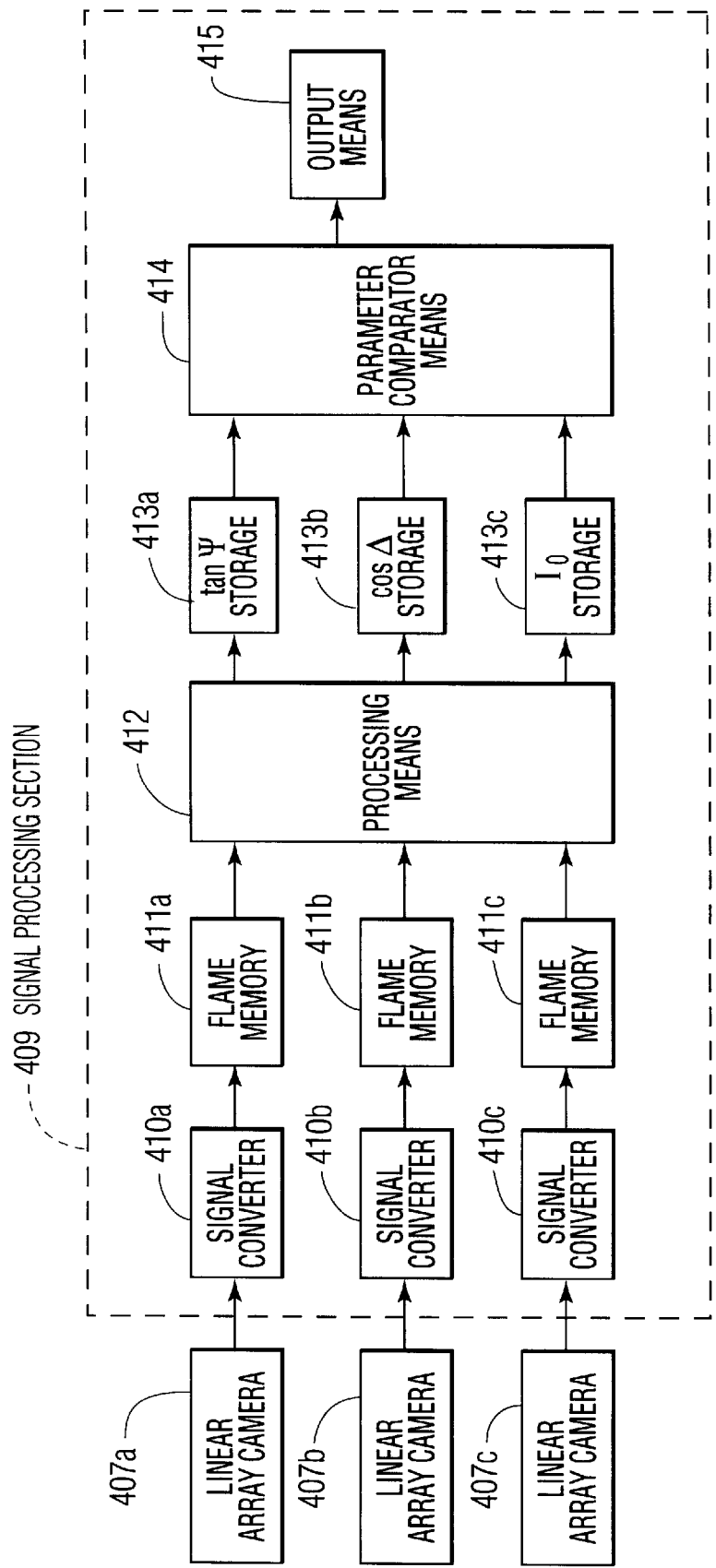
FIG. 33 is a block diagram showing a signal processing section in the embodiment of FIG. 32.

FIGS. 32 and 33 show an arrangement of the surface flaw detecting apparatus according to this embodiment. FIG. 32 is a layout view of an optical system and FIG. 33 is a block diagram showing the signal processing section. As shown in FIG. 32, an optical system 401 comprises a light irradiating section 402 and a light receiving section 403. The light irradiating section 402 has a light source 404 and a polarizer 405 disposed in front of the light source 404. The light source 404 comprises a planar light source which is formed to extend in the direction of width of a product to be inspected, e.g., a steel plate 406, and irradiates light of parallel flux to the surface of the steel plate 106 over a certain length. The polarizer 405 comprises, e.g., a polarizing plate or filter and, as shown in FIG. 34, it is arranged such that an angle $α_1$ formed between the transmission axis P of the polarizer and the incident plane on the steel plate 406 is π/4. The light receiving section 403 comprises three linear array cameras 407a, 407b, 407c and three analyzers 408a, 408b, 408c disposed in front of light receiving surfaces of the linear array cameras 407a, 407b, 407c. The linear array cameras 407a, 407b, 407c each comprising a group of CCD devices, for example, are arranged at respective positions shifted from each other in the moving direction of the steel plate 406, and detect the reflected light from the surface of the steel plate 406 for conversion into polarization image signals. The analyzers 408a, 408b, 408c each comprise, e.g., a polarizing plate or filter and, as shown in FIG. 34, they are arranged such that an angle $α_2$ formed between the transmission axis A of each analyzer 408 and the incident plane on the steel plate 406 is 0 for the analyzer 408a, π/4 for the analyzer 408b, and −π/4 for the analyzer 408c.

The signal processing section 409 comprises signal converters 410a, 410b, 410c, frame memories 411a, 411b, 411c, a CPU (processing means) 412, a tan Ψ storage 413a, a cos Δ storage 413b, an $I_0$ storage 413c, a parameter comparator 414, and output means 415. The signal converters 410a, 410b, 410c set, as reference levels, those signals of the polarization image signals output from the linear array cameras 407a, 407b, 407c which represent a normal portion on the surface of the steel plate 406, normalize and level the polarization image signals output from the linear array cameras 407a, 407b, 407c such that each signal indicative of the normal portion represents the center luminance in the range of entire gradations, and convert the received image signals into image signals representing relative changes with respect to the normal portion. Image signals output from the signal converters 410a, 410b, 410c are two-dimensionally developed in the frame memories 411a, 411b, 411c on a pixel-by-pixel basis, respectively. The CPU 412 reads the image signals for the same position on the steel plate 406 from the frame memories 411a, 411b, 411c successively, calculates the two ellipso-parameters, i.e., the amplitude reflectance ratio tan Ψ and cos Δ indicative of the phase difference Δ, and the intensity $I_0$ of the reflected light from the surface of the steel plate 406 for respective corresponding pixels, and then stores the calculated parameter values in the tan Ψ storage 413a, the cos Δ storage 413b and the $I_0$ storage 413c. The parameter comparator 414 determines the presence or absence of patterned flaws and/or irregularity flaws on the surface of the steel plate 406 and the type thereof from level changes in the values of tan Ψ, cos Δ and the reflected light intensity $I_0$ stored respectively in the tan Ψ storage 413a, the cos Δ storage 413b and the $I_0$ storage 413c.

Prior to describing the operation of the surface flaw detecting apparatus thus arranged, the principles for calculating the amplitude reflectance ratio tan Ψ, cos Δ and the intensity $I_0$ of the reflected light from the surface of the steel plate 406 based on the light intensities detected by the three linear array cameras 407a, 407b, 407c will first be described.

Assuming that, in the case of the reflected light from the steel plate 406 entering each polarizer 408 as shown in FIG. 34, the angles formed between the transmission axis P of the polarizer 405 and the transmission axis A of the analyzer 408 and the incident plane on the steel plate 406 are $\alpha_1$ and $\alpha_2$, respectively, when a P-polarized light component and an S-polarized light component impinge upon the steel plate 406 at an arbitrary incident angle i and are reflected by the plate surface, the light intensity $I(\alpha_1, \alpha_2)$ of a resultant of the two components after passing through the analyzer 408 is expressed below, given amplitude reflectances of the P- and S-components being $r_P$ and $r_S$, respectively:

$$I(\alpha_1, \alpha_2) = |E_0\cos\alpha_1 \cdot r_P\cos\alpha_2 + E_0\sin\alpha_1 \cdot r_S\sin\alpha_2|^2$$
$$= 2I_0[\rho^2\cos^2\alpha_1 \cdot \cos^2\alpha_2 + \sin^2\alpha_1 \cdot \sin^2\alpha_2 + (1/2)\rho\sin2\alpha_1 \cdot \sin2\alpha_2 \cdot \cos\Delta]$$

where $$I_0 = |E_0|^2 \cdot R_s/2, r_P = \sqrt{R_P} \cdot \exp(i\phi_p),$$
$$r_s = \sqrt{R_s} \cdot \exp(i\phi_s), \rho = \sqrt{R_P}/\sqrt{R_s} = \tan\Psi,$$

and $\Delta = \phi_s - \phi_p$

Assuming now $\alpha_1=\pi/4$, the light intensity $I_1$ passing through the analyzer 408a of $\alpha_2=0$ is given by $I_1=I_0\rho^2$, the light intensity $I_2$ passing through the analyzer 408b of $\alpha_2=\pi/4$ is given by $I_2=I_0(1+\rho^2+2\rho\cos\Delta)/2$, and the light intensity $I_3$ passing through the analyzer 408c of $\alpha_2=\pi/4$ is given by $I_3=I_0(1+\rho^2-2\rho\cos\Delta)/2$. From these light intensities $I_1$, $I_2$ and $I_3$, tan Ψ, cos Δ and the reflected light intensity $I_0$ are calculated as follows:

$$\tan\Psi = \sqrt{\frac{I_1}{I_2+I_3-I_1}}$$

$$\cos\Delta = \frac{I_2-I_3}{2I_1}\tan\Psi$$

$$I_0 = I_2 + I_3 - I_1$$

Note that any of the light intensities $I_1$, $I_2$ and $I_3$ may be multiplied a constant depending on selection of amplifier gains of the cameras.

The operation of the apparatus for detecting flaws based on the above principles will be described below. The polarized light irradiated through the light irradiating section 402 to the steel plate 406 moving at a constant speed is reflected by the plate surface and enters the linear array cameras 407a, 407b, 407c through the analyzers 408a, 408b, 408c. When the linear array cameras 407a, 407b, 407c detect the intensity of the reflected light coming from the steel plate 406, the linear array camera 407a detects the light intensity $I_1$ as the analyzer 408a of $\alpha_2=0$ is disposed in front of the camera 407a, the linear array camera 407b detects the light intensity $I_2$ as the analyzer 408b of $\alpha_2=\pi/4$ is disposed in front of the camera 407b, and the linear array camera 407c detects the light intensity $I_3$ as the analyzer of 408c of $\alpha_2=-\pi/4$ is disposed in front of the camera 407c. If the gain of the linear array camera 407a is set to ½ of the gains of the linear array cameras 407b, 407c so that the polarization image signals output from the linear array cameras 407a, 407b, 407c have output levels comparable to each other, the light intensity $I_1$ in the above formulae represents a value twice the light intensity actually detected by the linear array camera 407a.

Figure 35A:
Figure 36A:
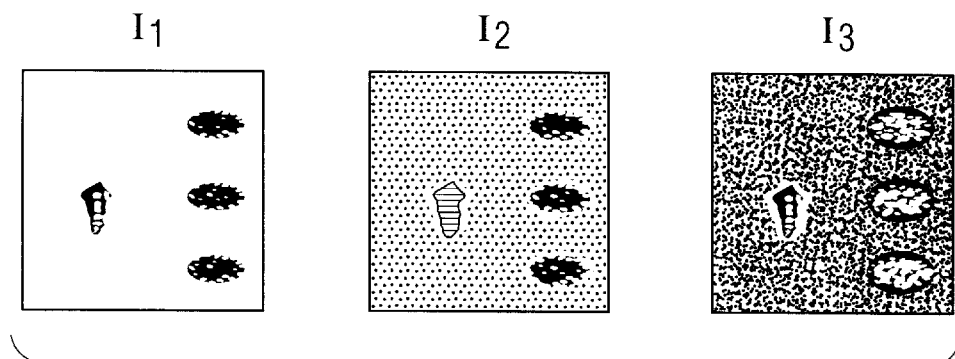
FIGS. 36(a) to 36(c) are screen representations showing images subjected to the normalizing process in the embodiment of FIG. 32.
Figure 36B:
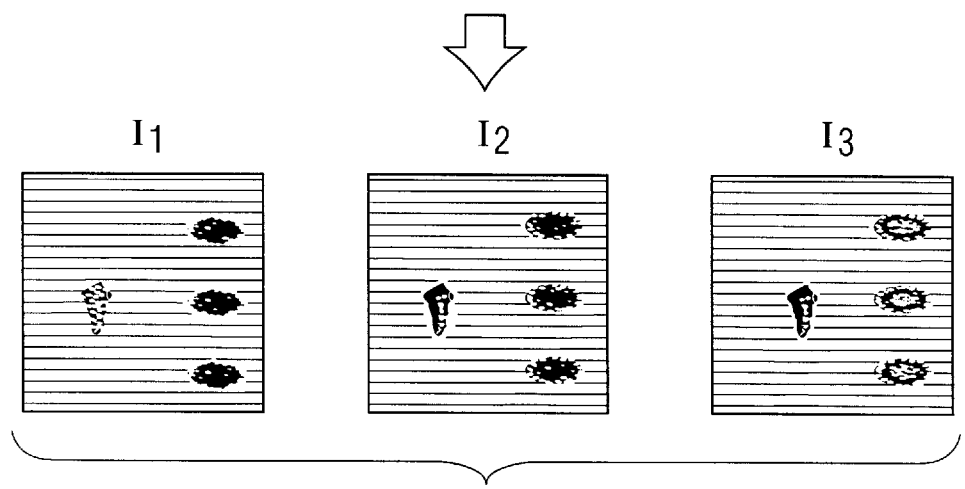
Figure 36C:
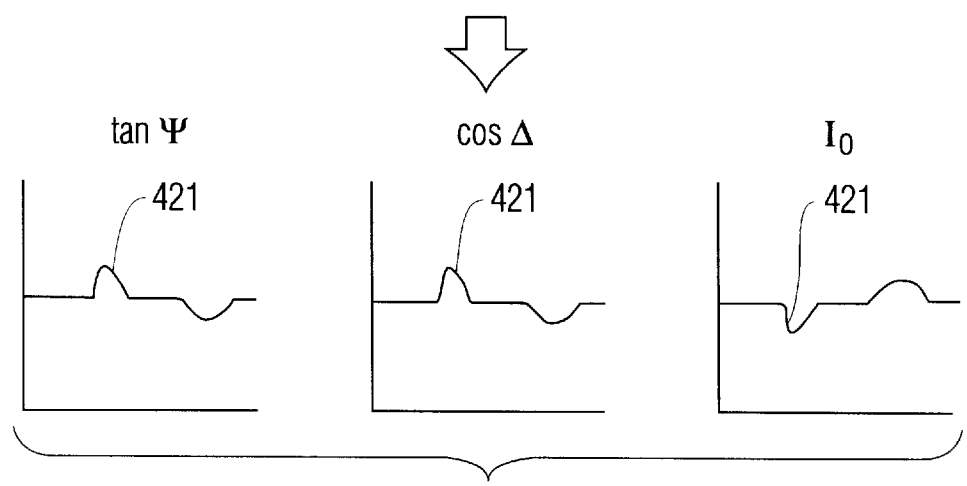

The polarization image signals representing the light intensities $I_1$, $I_2$, $I_3$ detected by the linear array cameras 407a, 407b, 407c are sent to the signal converters 410a, 410b, 410c, respectively. The signal converters 410a, 410b, 410c normalize and level the polarization image signals representing the light intensities $I_1$, $I_2$, $I_3$ received thereby such that each image signal indicative of the normal portion represents the center luminance in the range of entire gradations, while using the image signal indicative of the normal portion as a reference level, and convert the received image signals into image signals representing relative changes with respect to the normal portion. For example, the polarization image signals representing the light intensities $I_1$, $I_2$, $I_3$ detected by the linear array cameras 407a, 407b, 407c, shown in FIG. 35(a), are normalized and leveled as shown in FIG. 35(b). Specifically, each of the polarization image signals is normalized with the image signal indicative of the normal portion as a reference level such that image signal indicative of the normal portion represents the gradation 128, i.e., the center luminance in the range of total 256 gradations. Simultaneously, the light intensities $I_1$, $I_2$, $I_3$ are each averaged over a predetermined moving average range in the widthwise direction to determine the average luminance for leveling. The image signals representing relative changes in the normalized and leveled values with respect to the value corresponding to the normal portion are stored in the frame memories 411a, 411b, 411c on a pixel-by-pixel basis. The images before and after the light intensities $I_1$, $I_2$, $I_3$ are normalized and leveled as explained above are shown in FIGS. 36(a) and 36(b), respectively. In FIG. 36(a), the polarization image signals representing the light intensities $I_1$, $I_2$, $I_3$ detected by the linear array cameras 407a, 407b, 407c form images of which tones are different depending on actual luminance values of the light intensities $I_1$, $I_2$, $I_3$. On the other hand, as shown in FIG. 36(b), the images representing the normalized relative change signals are varied in tone such that abnormal portions appear brighter or darker than the normal portion having the same density as a reference. By so normalizing the light intensities $I_1$, $I_2$, $I_3$ detected by the linear array cameras 407a, 407b, 407c with respect to the normal portion as a reference, the problem such as drifts in gains of the linear array cameras 407a, 407b, 407c is avoided and the images precisely depending on the light intensities $I_1$, $I_2$, $I_3$ are obtained.

Figure 37A:
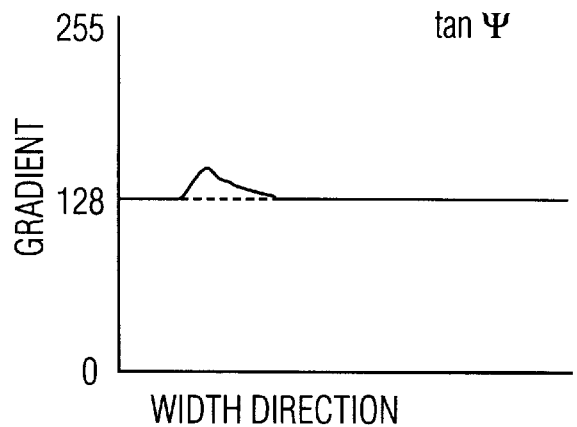
FIGS. 37(a) to 37(c) are screen representations showing images of tan $\Psi$, cos $\Delta$ and $I_0$ in the embodiment of FIG. 32.
Figure 37B:
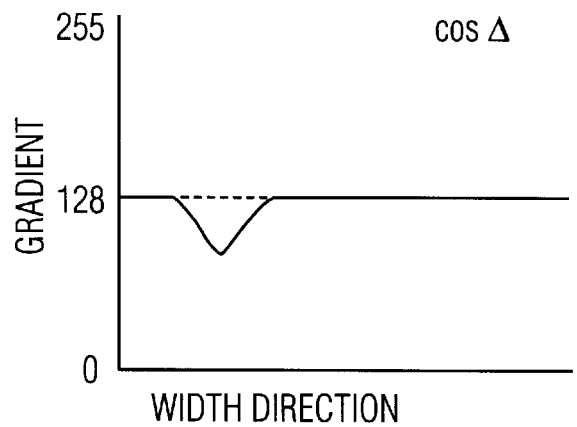
Figure 37C:
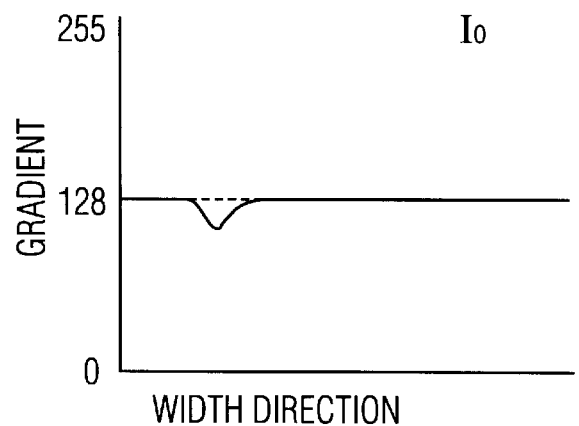

The CPU 412 reads the image signals representing relative changes in the light intensities $I_1$, $I_2$, $I_3$ developed in the frame memories 411a, 411b, 411c successively, calculates the amplitude reflectance ratio tan Ψ, cos Δ and the intensity $I_0$ of the reflected light for respective corresponding pixels, and then stores the calculated parameter values, as image data of tan Ψ, cos Δ and $I_0$, in the tan Ψ storage 413a, the cos Δ storage 413b and the $I_0$ storage 413c. Images of tan Ψ, cos Δ and $I_0$ provided as a result of the above calculation are relative value images with the normal portion as a reference, as shown in FIGS. 37(a) to 37(c). As to cos Δ, for example, the image is produced with the normal portion of Δ=90 degrees as a reference such that the abnormal portions become bright or dark. The relative value images of tan Ψ, cos Δ and $I_0$ are indicated on a display (not shown).

Based on level changes in the values of tan Ψ, cos Δ and the reflected light intensity $I_0$ stored respectively in the tan Ψ storage 413a, the cos Δ storage 413b and the $I_0$ storage 413c, the parameter comparator 414 determines the presence or absence of patterned flaws and/or irregularity flaws on the surface of the steel plate 406 and the type thereof, the determined results being output to a recorder or a display through the output means 415. More specifically, as will be seen from the images of tan Ψ, cos Δ and $I_0$, the abnormal portions of the steel plate 406 have different polarities with respect to the normal portion as a reference depending on the types of abnormality, i.e., flaws. For example, a flaw 421 caused by inclusions within the steel plate 406 shows positive levels in the images of tan Ψ and cos Δ, but a negative level in the image of $I_0$. On the other hand, oil stains show positive, negative and positive levels in the images of tan Ψ, cos Δ and $I_0$, respectively, or positive levels in all the images. Thus, the type of abnormality can be discriminated depending on the levels of tan Ψ, cos Δ and $I_0$.

By so producing the relative value images through normalization by which the image signal indicative of the normal portion is set to the gradation 128, i.e., the center luminance in the range of total 256 gradations, changes in the ellipso-parameters tan Ψ and cos Δ in the abnormal portion are made appear notedly. More specifically, in spite of that gradations in image processing generally range from 0 to 255, when the gradation of the normal portion as to the light intensity $I_3$ detected by the linear array camera 407c is low, the entire image becomes very dark as shown in, by way of example, the $I_3$ image of FIG. 36(a). If absolute values of the ellipso-parameters tan Ψ and cos Δ are calculated using such image data, changes in the ellipso-parameters tan Ψ and cos Δ in the abnormal portion would not appear apparently, resulting in a difficulty to detect flaws. With this embodiment, such a drawback can be eliminated.

Figure 38:
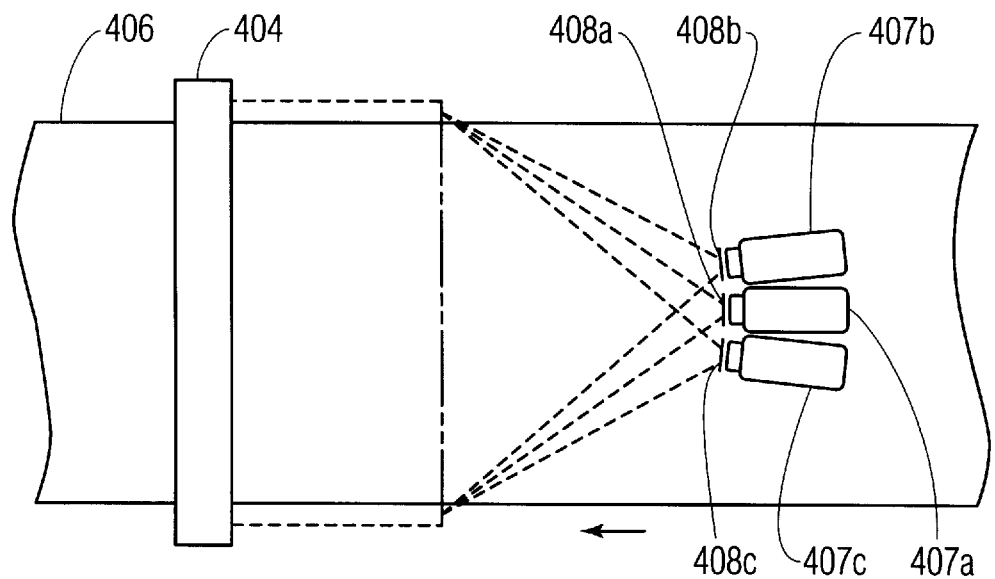
FIG. 38 is a plan view showing an optical system in another embodiment.
Figure 39:
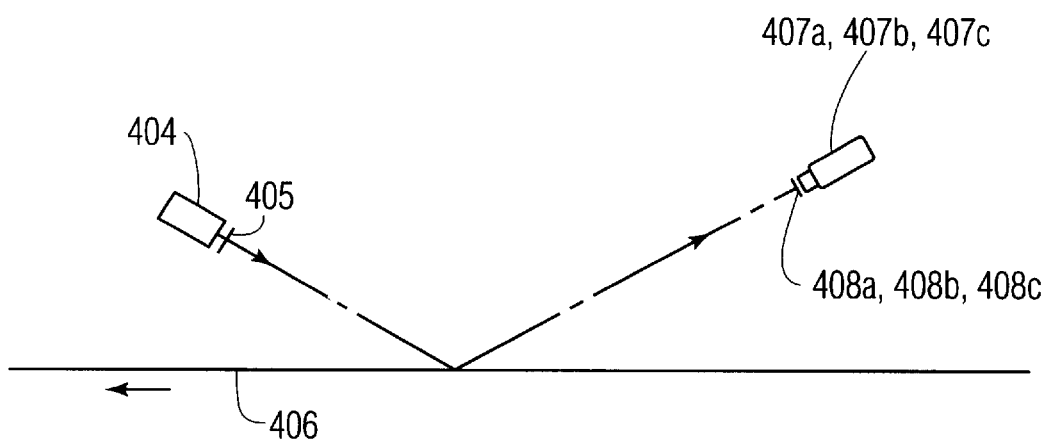
FIG. 39 is a side view showing the optical system in the embodiment of FIG. 38.

In the above illustrated embodiment, the linear array cameras 407a, 407b, 407c in the light receiving section 403 are disposed at positions shifted from each other in the moving direction of the steel plate 406. As shown in a plan view of FIG. 38 and a side view of FIG. 39, however, the linear array cameras 407a, 407b, 407c may be disposed at the same height on a line perpendicular to the moving direction of the steel plate 406 so that the reflected light from the same position on the steel plate 406 is detected by the linear array cameras 407a, 407b, 407c simultaneously.

Though the foregoing embodiment explaines the case that the linear cameras are disposed at positions shifted each other, the reflected light can be splitted by the beam splitter as shown in FIG. 28 and received. The receiving of reflected light does not depend on the form of the optical system.

Figure 40:
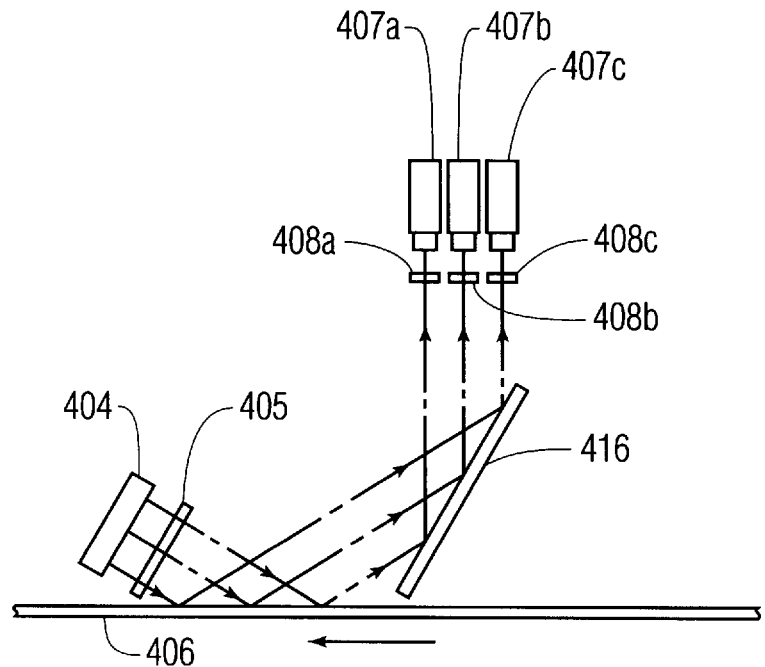
FIG. 40 is a side view showing an optical system in another embodiment.

In the foregoing embodiments, the polarized light emitted though the light irradiating section 402 is directly irradiated to the surface of the steel plate 406 and the reflected light there from is directly received by the linear array cameras 407a, 407b, 407c, As shown in FIG. 40, however, the optical system may be modified such that light emitted from the light Source 404 is irradiated to the surface of the steel plate 106 at an predetermined incident angle through the polarizer 405, and the reflected light therefrom is first reflected by a mirror 416 and then received by the linear array cameras 407a, 407b, 407c disposed perpendicularly to the surface of the steel plate 406. By so arranging the light irradiating section 402 and the light receiving section 403, an installation space necessary for the optical system 401 can be reduced and the degree of freedom in design of the on-line system can be improved. Since this embodiment makes evaluation based on not absolute changes, but relative changes in tan Ψ, cos Δ and $I_0$, an effect of the mirror 416 made of aluminum or the like upon polarization is not problematic and, hence, the degree of freedom in design of construction and installation of the optical system 401.

As described above, according to Embodiment-5, polarized light is irradiated to the inspected surface, the reflected light from the inspected surface is received through analyzers having different azimuth angles from each other, light intensity distributions of polarized lights having different oscillating planes are measured, and the measured light intensity distributions are normalized and leveled such that a normal portion corresponds to the center luminance in the range of entire gradations, for conversion into image signals representing relative changes with respect to the normal portion. Therefore, the problem such as drifts in gains of the cameras in the light receiving section is avoided and the images precisely depending on the actual light intensities can be produced.

Also, since the two ellipso-parameters tan Ψ and cos Δ and the intensity $I_0$ of the reflected light are calculated from the relative value images produced as above, changes in the two ellipso-parameters tan Ψ and cos Δ and the intensity $I_0$ of the reflected light in the abnormal portion are made apparently distinctive. As a result, the presence or absence of abnormality on the surface of a sheet-like product and the type thereof can accurately be detected on-line.

Additionally, since not absolute values, but relative values of the ellipso-parameters are measured, strict requirements for the optical system and the signal processing section are greatly moderated, the cost the entire apparatus can be reduced and set-up and adjustment of the apparatus can also be facilitated.

EMBODIMENT-6

A surface flaw detecting apparatus according to this embodiment comprises a light irradiating section, a light receiving section, and a signal processing section. The light irradiating section irradiates polarized light to a surface to be inspected. The light receiving section includes a plurality of light receiving optical systems for receiving at least three polarized lights having polarizing planes of particular different angles, and detects the reflected light from the inspected surface for conversion into image signals. The signal processing section normalizes respective light intensity distributions output from the light receiving optical systems with respect to reference values, and compares change polarities and amounts (deviations) of the normalized light intensity distributions with predetermined patterns for determining the flaw type.

Preferably, the signal processing section not only normalizes respective light intensity distributions output from the light receiving optical systems with respect to reference values and compares change polarities and deviations of the normalized light intensity distributions with predetermined patterns for determining the flaw type, but also calculates visually-equivalent changes in the light intensities from the respective light intensity distributions output from the light receiving optical systems and compares the calculated changes in the light intensities with predetermined patterns for determining the flaw grade.

Polarized light is sensitive to physical properties of a reflecting surface, particularly a thin film. The direction in which polarized light has the maximum intensity is also changed depending on physical properties of a reflecting surface. Flaws on metal surfaces are marked if some parts have different surface characteristics from a normal portion and hence have different physical properties from the matrix, or if some parts have different surface geometrical configurations, such as irregularities, from a normal portion. The former flaws can be detected by utilizing polarized light, and the latter flaws can be detected from change in the reflected light intensity because the surface reflectance is varied with the latter flaws.

In this embodiment, therefore, the light irradiating section is arranged so as to irradiate polarized light to the inspected surface over its full width at a certain incident angle, and the light receiving section is arranged so as to receive the reflected light from the inspected Surface. The light receiving section includes a beam splitter for separating the incoming light into three beams, three sets of linear array cameras, each of which comprises, e.g., a CCD sensor, for receiving the separated three beams and outputting image signals, respectively, and three analyzers disposed between the beam splitter and the linear array cameras for converting the reflected light from the inspected surface into polarized lights having different oscillating planes from each other. The three analyzers are arranged such that they have different azimuth angles from each other, i.e., such that the angles formed between their transmission axes and the incident plane on the inspected surface are, e.g., 0, $\pi/4$ and $-\pi/4$.

The signal processing section normalizes and levels the image signals output from the linear array cameras after shading compensation such that the signal indicative of a normal portion represents the center density in the range of entire gradations, and converts the received image signals into light intensity signals representing relative changes with respect to the normal portion. The signal processing section compares change polarities and deviations in distributions of those three light intensity signals representing relative changes with respect to the normal portion with the predetermined patterns for detecting changes in the polarized condition. From the change polarities and the magnitudes of the deviations in the distributions of those three light intensity signals with respect to the normal portion, the signal processing section determines the type of the flaw which has different surface physical properties from the matrix.

Further, in addition to the above process, the signal processing section calculates visually-equivalent change in the light intensity, i.e., the intensity of the reflected light not divided into polarized light components, from the respective light intensity distributions output from the light receiving optical systems and compares the calculated changes in the light intensities with the predetermined patterns. From the change polarities and the magnitudes of deviations of the calculated changes in the light intensities, the signal processing section determines the grade of the flaw which has different surface geometrical configurations with respect to the normal section, such as a flaw in the form of irregularities.

Figure 41:
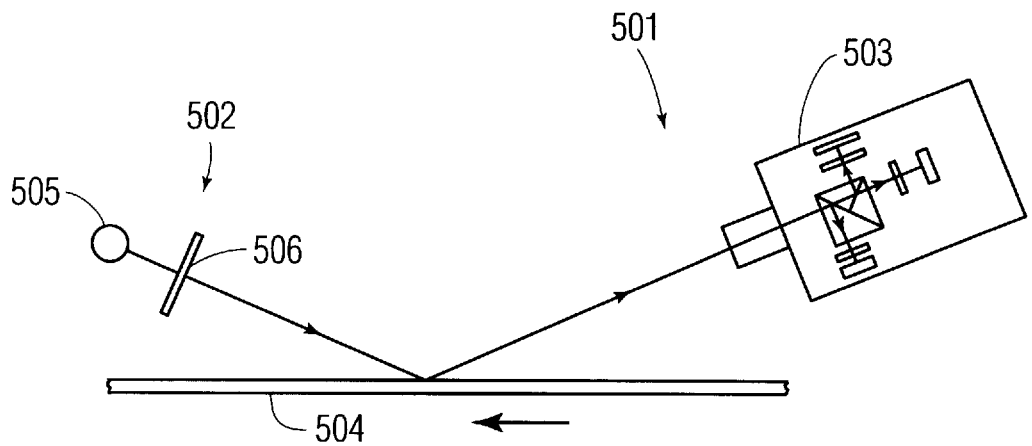
FIG. 41 is a layout view showing an optical system in an embodiment of the present invention.
Figure 42:
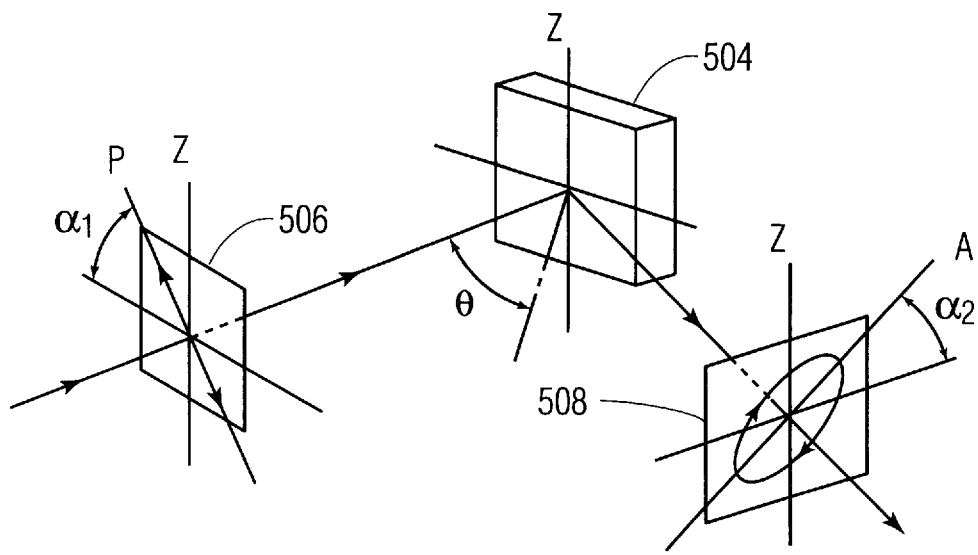
FIG. 42 is an explanatory view showing the operation principle of the optical system in the embodiment of FIG. 41.
Figure 43:
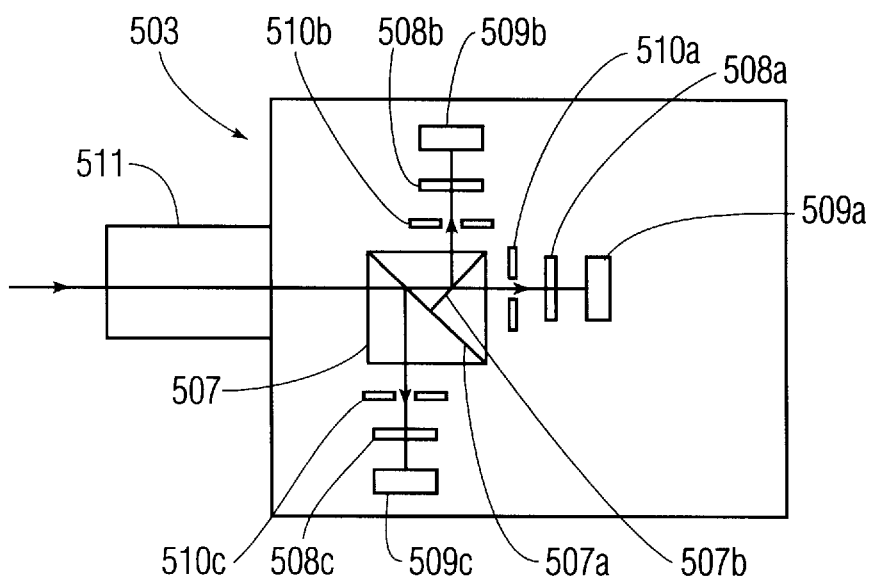
FIG. 43 is a view showing the configuration of a three-plate polarization linear array camera in the embodiment of FIG. 41.

FIG. 41 is a layout view of an optical system for use in the surface flaw detecting apparatus of this embodiment. As shown in FIG. 41, an optical system 501 comprises a light irradiating section 502 and a three-plate type polarization linear array camera 503. The light irradiating section 502 irradiates polarized light to the surface of a product to be inspected, e.g., a steel plate 504, at a certain incident angle. The light irradiating section 502 comprises a light source 505 and a polarizer 506 disposed in front of the light source 505. The light source 505 is formed of a bar-shaped light emitting device extending in the direction of width of the steel plate 504, and irradiates light over the full width of the steel plate 504. The polarizer 506 comprises, e.g., a polarizing plate or filter and, as shown in an explanatory view of FIG. 42, it is arranged such that an angle $\alpha_1$ formed between the transmission axis P of the polarizing plate and the incident plane on the steel plate 504 is $\pi/4$. As shown in a structural view of FIG. 43, the three-plate type polarization linear array camera 503 comprises a beam splitter 507, three analyzers 508a, 508b, 508c and three linear array sensors 509a, 509b, 509c. The beam splitter 507 consists of three prisms combined with each other so as to have two semi-transmissive reflecting surfaces which are each formed by laminating multilayer films of dielectrics on a light separating surface with vapor deposition. A first reflecting surface 507a which receives the reflected light from the steel plate 504 is formed to have an approximately 2:1 ratio of transmittance to reflectance, and a second reflecting surface 507b which receives the light having passed through the first reflecting surface 507a is formed to have a 1:1 ratio of transmittance to reflectance. Thus, the beam splitter separates the reflected light from the steel plate 504 into three beams having the same light intensity. Incidentally, the optical path lengths from the incident surface of the beam splitter 507 to the respective emergent surfaces from which the separated three beams come out of the splitter are set to be the same. The analyzer 508a is disposed in an optical path of the light having passed through the second reflecting surface 507b and is oriented such that an azimuth angle $\alpha_2$, shown in FIG. 42, formed between the transmission axis A of the analyzer and the incident plane on the steel plate 504 is 0. The analyzer 508b is arranged in an optical path of the light reflected by the second reflecting surface 507b such that the azimuth angle $\alpha_2$ is $\pi/4$. The analyzer 508c is arranged in an optical path of the light reflected by the first reflecting surface 507a such that the azimuth angle $\alpha_2$ is $-\pi/4$. The linear array sensors 509a, 509b, 509c each comprise a CCD sensor, for example, and are disposed downstream of the analyzers 508a, 508b, 509c, respectively. Further, slits 510a, 510b, 510c for cutting off the light multi-reflected in the beam splitter 507 and useless scattered light are disposed between the beam splitter 507 and the analyzers 508a, 508b, 508c, respectively, and a lens group 511 is disposed in front of the beam splitter 507. Gains of the linear array sensors 509a, 509b, 509c are adjusted so that all the sensors output signals of the same level when lights having the same intensity enter them.

Thus, with the above unitized structure that the analyzers 508a, 508b, 508c and the linear array sensors 509a, 509b, 509c are provided in the respective optical paths of three beams branched by separating the incoming light, when the linear array sensors 509a, 509b, 509c, etc. are disposed near the feed pass of the steel plate 504 to detect the reflected light from the steel plate 504, position adjustment of the linear array sensors 509a, 509b, 509c, etc. is not necessary and the reflected light from the same position on the steel plate 504 can be detected by the three sensors at the same timing. Also, the three sets of linear array sensors 509a, 509b, 509c are all housed in one three-plate type polarization linear array camera 503 and the size of the entire detecting system is reduced. Therefore, the three-plate type polarization linear array camera 503 can easily be disposed in the optical path of the reflected light from the steel plate 504 and its mount position can optionally be selected, which increases the degree of freedom in design of the optical system 501.

Figure 44:
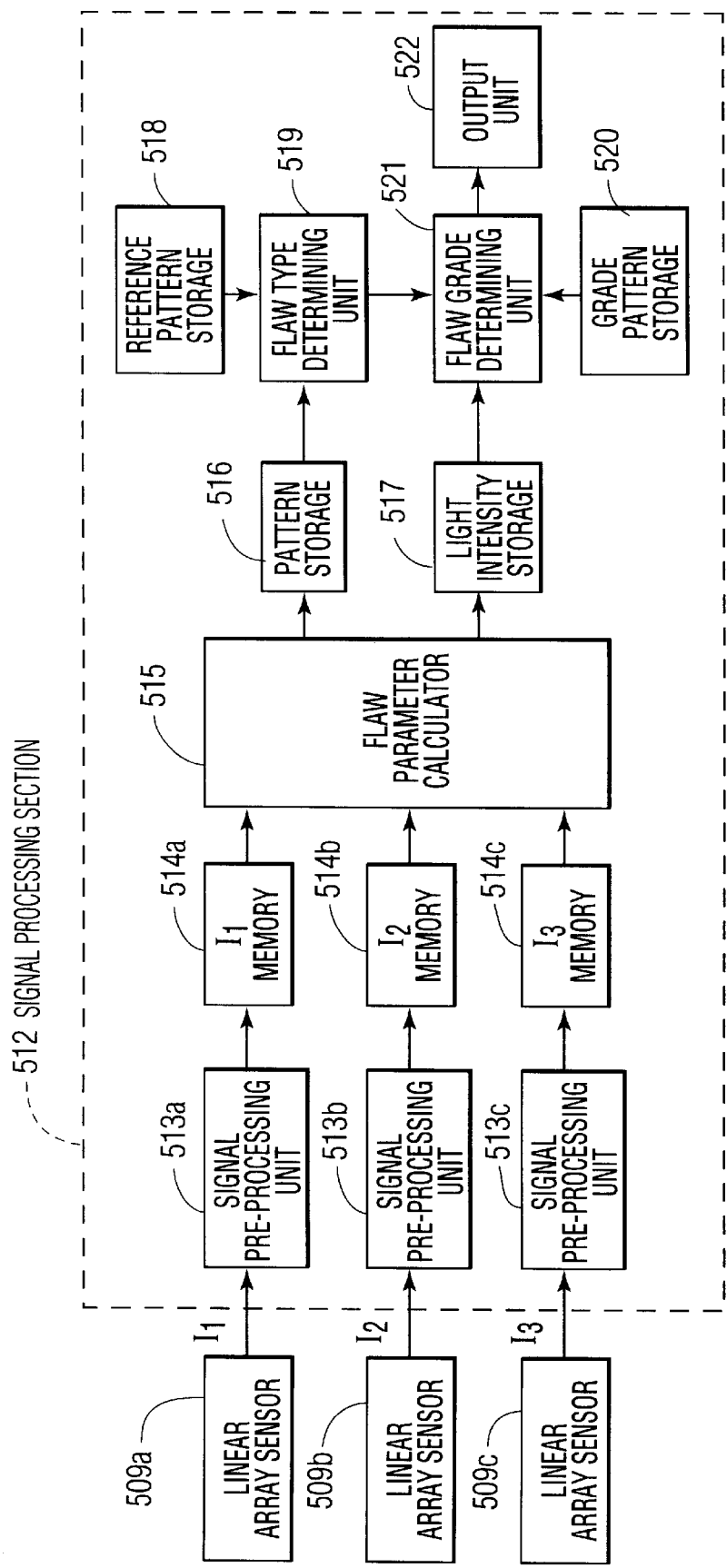
FIG. 44 is a block diagram showing a signal processing section in the embodiment of FIG. 41.

As shown in a block diagram of FIG. 44, the linear array sensors 509a, 509b, 509c of the three-plate type polarization linear array camera 503 are connected to a signal processing section 512. The signal processing section 512 comprises signal pre-processing units 513a, 513b, 513c, an $I_1$ memory 514a, an $I_2$ memory 514b, an $I_3$ memory 514c, a flaw parameter calculator 515, a pattern storage 516, a light intensity storage 517, a reference pattern storage 518, a flaw type determining unit 519, a grade pattern storage 520, a flaw grade determining unit 521, and an output unit 522. The signal pre-processing units 513a–513c performs shading compensation and so on to compensate for effects of gain variations in the widthwise direction, etc. contained in polarized-light intensity signals $I_1$, $I_2$, $I_3$ output from the linear array sensors 509a–509c, normalizes each of the compensated signals with the signal indicative of a normal portion as a reference level such that the signal indicative of the normal portion represents the gradation 128, i.e., the center density in the range of total 256 gradations, and stores the normalized light intensity signals $I_1$, $I_2$, $I_3$ in the $I_1$ memory 514a, the $I_2$ memory 514b and the $I_3$ memory 514c, respectively. The flaw parameter calculator 515 calculates not only a polarity pattern representing whether peak values, which correspond to a flaw, appeared in distributions of the light intensity signals $I_1$, $I_2$, $I_3$ stored in the $I_1$ memory 514a, the $I_2$ memory 514b and the $I_3$ memory 514c are positive (plus) or negative (minus) with respect to the gradation 128, i.e., the value indicative of the normal portion, as a reference, but also a value pattern representing the deviations of the above peak values with respect to the gradation 128 as a reference, and also calculates the maximum visually-equivalent intensity Imax of the light not divided into polarized light components from the light intensity signals corresponding to the flaw. The pattern storage 516 stores the calculated polarity pattern and value pattern, and the light intensity storage 517 stores the calculated maximum visually-equivalent light intensity Imax. The reference pattern storage 518 stores in advance various polarity patterns, value patterns, and corresponding flaw types. The flaw type determining unit 519 compares the polarity pattern and the value pattern stored in the pattern storage 516 with the various polarity patterns and value patterns stored in the reference pattern storage 518 for determining the flaw type. The grade pattern storage 520 stores in advance a grade reference pattern representative of flaw grades depending the light intensity for each of flaws. The flaw grade determining unit 521 compares the maximum visually-equivalent light intensity Imax stored in the light intensity storage 517 and the flaw type determined by the flaw type determining unit 519 with the grade reference patterns stored in the grade pattern storage 520 for the respective flaw types, thereby determining the flaw grade. The flaw type and grade output from the flaw grade determining unit 521 are output to a display or a recorder (not shown) through the output unit 522.

The operation of the thus-arranged apparatus for detecting flaws on the surface of the steel plate 504 will be described below.

The polarized light irradiated through the light irradiation section 502 to the steel plate 504 moving at a constant speed is reflected by the surface of the steel plate 504 and then received by the three-plate type polarization linear array camera 503. The reflected light from the steel plate 504 having entered the three-plate type polarization linear array camera 503 is separated by the beam splitter 507 into three beams which enter the linear array sensors 509a, 509b, 509c through the analyzers 508a, 508b, 508c. Because of the analyzers 508a–509c being disposed in front of the linear array sensors 509a–509c, respectively, when the linear array sensors 509a–509c detect the intensity of the reflected light, they detect the light intensities $I_1$, $I_2$, $I_3$ of different polarized light components and send the detected values to the signal processing section 512.

Figure 45A:
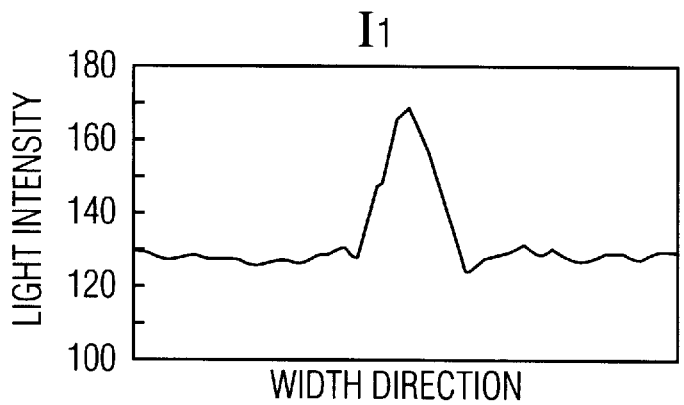
FIGS. 45(a) to 45(c) are light intensity distribution charts showing flaw signals.
Figure 45B:
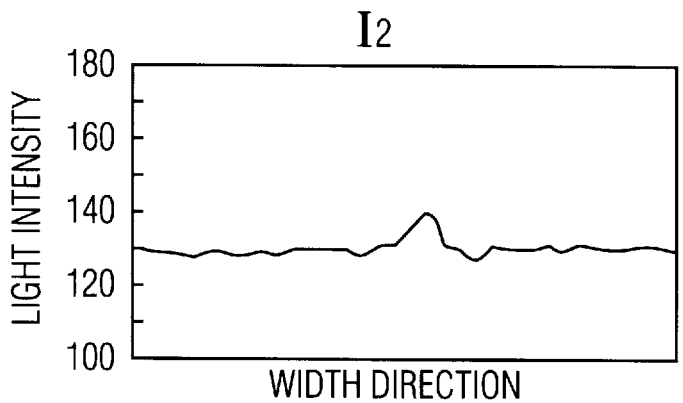
Figure 45C:
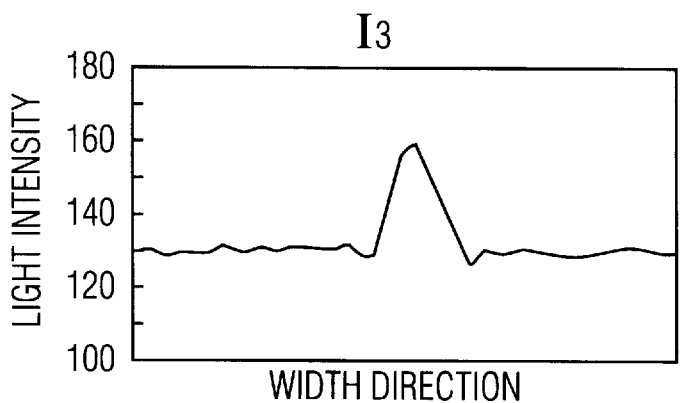
Figure 47A:
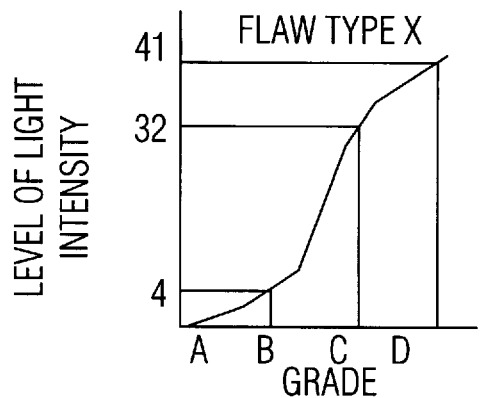
FIGS. 47(a) to 47(d) are graphs showing correlation between light intensity levels and grades.
Figure 47B:
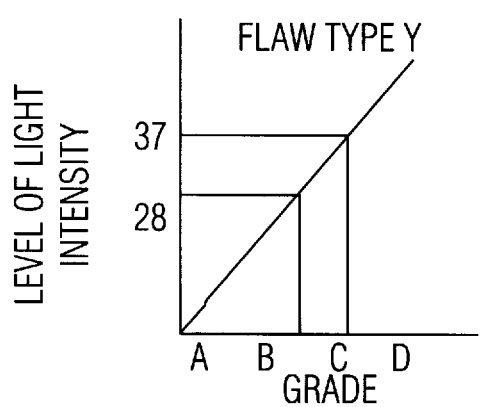
Figure 47C:
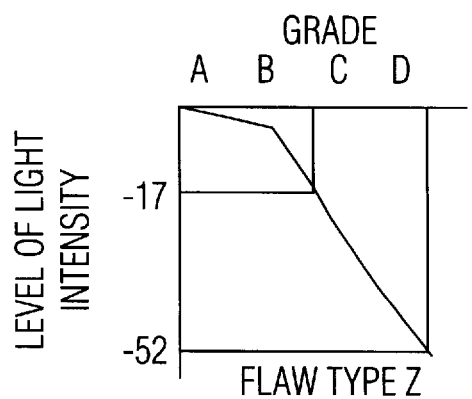
Figure 47D:
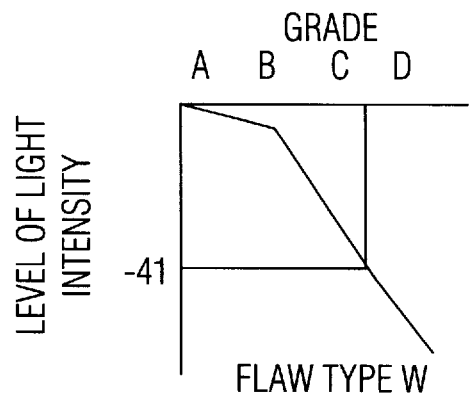

The signal pre-processing units 513a–513c in the signal processing section 512 performs shading compensation and so on to compensate for effects of gain variations in the widthwise direction, etc. contained in the polarized-light intensity signals $I_1$, $I_2$, $I_3$ output from the linear array sensors 509a–509c. Then, the signal pre-processing units 513a–513c normalize each of the compensated signals such that the signal indicative of the normal portion represents the gradation 128, by way of example, as shown in flaw signal distribution charts of FIGS. 45(a) to 45(c). The normalized light intensity signals $I_1$, $I_2$, $I_3$ are stored in the $I_1$ memory 514a, the $I_2$ memory 514b and the $I_3$ memory 514c, respectively. FIG. 45(a) shows distribution of the light intensity signal $I_1$, FIG. 45(b) shows distribution of the light intensity signal $I_2$, and FIG. 45(c) shows distribution of the light intensity signal $I_3$. The flaw parameter calculator 515 calculates not only a polarity pattern representing whether peak values, which correspond to a flaw, appeared in the distributions of the light intensity signals $I_1$, $I_2$, $I_3$ stored in the $I_1$ memory 514a, the $I_2$ memory 514b and the $I_3$ memory 514c are plus or minus with respect to the gradation 128, i.e., the value indicative of the normal portion, but also a value pattern representing the deviations of the above peak values with respect to the gradation 128 as a reference. In the example shown in FIG. 45, since the peak values corresponding to a flaw in the normalized light intensity signals $I_1$, $I_2$, $I_3$ are all deviated to the plus side from the gradation 128, a polarity pattern of (+, +, +) is calculated. Then, the deviations of the peak values corresponding to a flaw in the light intensity signals $I_1$, $I_2$, $I_3$ with respect to the gradation 128 as a reference is given by (+38, +10, +32). These deviations are normalized into (1.0, 0.26, 0.84) with the maximum value among them as a reference. These values (1.0, 0.26, 0.84) normalized with the maximum value of the deviations as a reference is calculated as a value pattern. The calculated polarity pattern and value pattern are stored in the pattern storage 516. The flaw parameter calculator 515 also calculates the maximum visually-equivalentintensity Imax of the light not divided into polarized light components from the distributions Of the light intensity signals $I_1$, $I_2$, $I_3$ corresponding to the flaw in accordance with the formula of Imax=MAX[$I_2$(x)+$I_3$(x)–$I_1$(x)]. The calculated maximum visually-equivalent light intensity Imax is stored in the light intensity storage 517. In the example shown in FIG. 45, since the deviations of the peak values corresponding to a flaw in the distributions of the light intensity signals $I_1$, $I_2$, $I_3$ are (+38, +10, +32), the maximum visually-equivalent light intensity Imax is "4".

Various polarity patterns and value patterns for a plurality of flaw types depending on the extent of each flaw are determined beforehand by experiments and stored in the reference pattern storage 518, by way of example, as shown in FIG. 46. In FIG. 46, X to W indicate flaw types listed in the order from a low degree of harmfulness to a high degree of harmfulness, for example. FIG. 46 also lists polarity patterns and reference values of value patterns corresponding to the flaw types X to W. Further, the correlation between levels of the light intensity and flaw grades for each of the flaw types X to W is examined beforehand and stored in the grade pattern storage 520, by way of example, as shown in a correlation table of FIG. 47.

The flaw type determining unit 519 compares the polarity pattern and the value pattern stored in the pattern storage 516, e.g., the polarity pattern (+, +, +) and the value pattern (1, 0.26, 0.84) in the example shown in FIG. 45, with the reference patterns, shown in FIG. 44, stored in the reference pattern storage 518, thereby determining the flaw type. In the example shown in FIG. 45, the detected flaw is determined as a type X flaw. FIG. 48 lists examples of results obtained by determining the types of a plurality of different flaws A to H based on the polarity patterns and the value patterns in such a way. When determining the flaw type, even for the flaws B and C having the same polarity pattern (−, −, −), these flaws can be classified into the type Y having a low degree of harmfulness and the type Z having a high degree of harmfulness based on their value patterns. It is thus possible to determine the flaw type correctly. Further, even if one of three signs of the polarity pattern is reversed or "0" depending on the flaw condition, as found with the flaw G, the flaw pattern can correctly be determined in combination with its value pattern. Additionally, since the flaw type is determined based on the polarity patterns and the value patterns, the process necessary for determining the flaw type is simplified so that the flaw type can precisely be determined in a shorter time.

On the other and, the flaw grade determining unit 521 compares the maximum visually-equivalent light intensity Imax stored in the light intensity storage 517 and the flaw type determined by the flaw type determining unit 519 with the table showing the correlation between levels of the light intensity and flaw grades, stored in the grade pattern storage 520, in accordance with corresponding one of the flaw types X to W, thereby determining the flaw grade. For example, when the flaw type is X and the maximum visually-equivalent light intensity Imax is "4", the flaw grade is ranked B. When the flaw type is Y and the maximum visually-equivalent light intensity Imax is "37", the flaw grade is ranked C. Thus, since the flaw grade is determined from the maximum visually-equivalentlight intensity Imax and the flaw type, it is possible to discriminate not only the extent of a patterned flaw, including no irregularities, on the surface of the steel plate 504, but also the extent of an irregularity flaw with good accuracy. The flaw grade determining unit 521 outputs both the flaw type determined by the flaw type determining unit 519 and the flaw grade determined by itself to the output unit 522. The output unit 522 then outputs the flaw type and grade from the flaw grade determining unit 521 to a display or a recorder.

As described above, according to Embodiment-6, the polarized light is irradiated to the inspected surface at a certain incident angle, distributions of the light intensities of a plurality of polarized light components of the reflected light from the inspected surface are detected, the detected light intensity distributions are each normalized to calculate change polarities and deviations in the distributions of the polarized-light intensity signals with respect to a normal portion, and the calculated change polarities and deviations are compared with predetermined patterns for determining the flaw type. Therefore, the flaw type can promptly be discriminated through a simple process.

Also, since visually-equivalent change in the light intensity, i.e., the intensity of the reflected light not divided into polarized light components, is calculated from the respective light intensity distributions output from the light receiving optical systems and the flaw grade is determined from the visually-equivalent change in the light intensity, not only the extent of a patterned flaw, including no irregularities, but also the extent of an irregularity flaw can be discriminated with good accuracy.

Additionally, since the flaw type and grade are determined in a prompt manner with a simple process, the construction of the apparatus itself can be simplified, and abnormal portions on the surface of a sheet-like product moving at a high speed can precisely be detected on-line.

EMBODIMENT-7

A surface flaw detecting apparatus according to this embodiment comprises a light irradiating section, a light detecting section, and a signal processing section. The light irradiating section irradiates polarized light to a surface to be inspected over its full width. The light detecting section comprises beam splitters for separating the reflected light from the inspected surface into three beams, analyzers disposed in respective optical paths of the separated three beams and having different azimuth angles from each other, and linear array sensors for receiving the beams (lights) having passed through the analyzers. The light detection section receives the reflected light from the inspected surface for conversion into image signals. The signal processing section comprises a flaw candidate area extractor, a parameter calculator and a determining unit. The flaw candidate area extractor compares density levels of polarization images input from the three sets of linear array sensors with reference density levels, and extracts, as flaw candidate areas, the areas in which the measured density levels of the polarization images are out of the vicinity of the respective reference density levels. The parameter calculator calculates the ellipso-parameters and the intensity of the reflected light based on the measured light intensities of pixels within the extracted flaw candidate areas. The determining unit compares characteristics of the calculated ellipso-parameters and intensity of the reflected light with predetermined characteristics of surface flaws for determining the type and grade of a surface flaw.

The surface flaw detecting apparatus of this embodiment comprises the light irradiating section, the light detecting section, and the signal processing section. The light irradiating section has a light source arranged so as to irradiate emitted light to the inspected surface over its full width at a certain incident angle. A polarizing plate is disposed between the light source and the position on the inspected surface upon which the incident light impinges. The light detecting section comprises three sets of linear array sensors and three analyzers disposed in front of respective light receiving surface of the linear array sensors. The three analyzers are arranged such that they have different azimuth angles from each other, i.e., such that the angles formed between their transmission axes and the incident plane on the inspected surface are, e.g., 0, $\pi/4$ and $-\pi/4$. The three sets of linear array sensors receive the polarized lights having passed through the corresponding analyzers and output images representing intensity distributions of the respective polarized lights to the signal processing section.

The signal processing section comprises the flaw candidate area extractor, the parameter calculator and the determining unit. The flaw candidate area extractor stores in advance reference density levels indicating the normal condition of the inspected Surface, or automatically determines reference density levels from peak values or variations of the measured data. The flaw candidate area extractor compares density levels of the polarization images input from the three sets of linear array sensors with the predetermined reference density levels, and extracts, as flaw candidate areas, the areas in which the measured density levels of the polarization images are out of the vicinity of the respective reference density levels. From the measured light intensities of the pixels within the extracted flaw candidate areas, the parameter calculator calculates the two ellipso-parameters tan $\Psi$ and cos $\Delta$ and the intensity of the reflected light. Thus, the area of those pixels which are to be subjected to processing is restricted and the processing time is cut down. Further, since the flaw candidate areas are specified prior to starting calculation in the parameter calculator, the signal levels indicative of a flow can be prevented from lowering and accuracy of flaw detection is increased correspondingly. The determining unit compares characteristics of the calculated ellipso-parameters and reflected light intensity with the predetermined characteristics of surface flaws, thereby determining the extent of abnormality.

Figure 49:
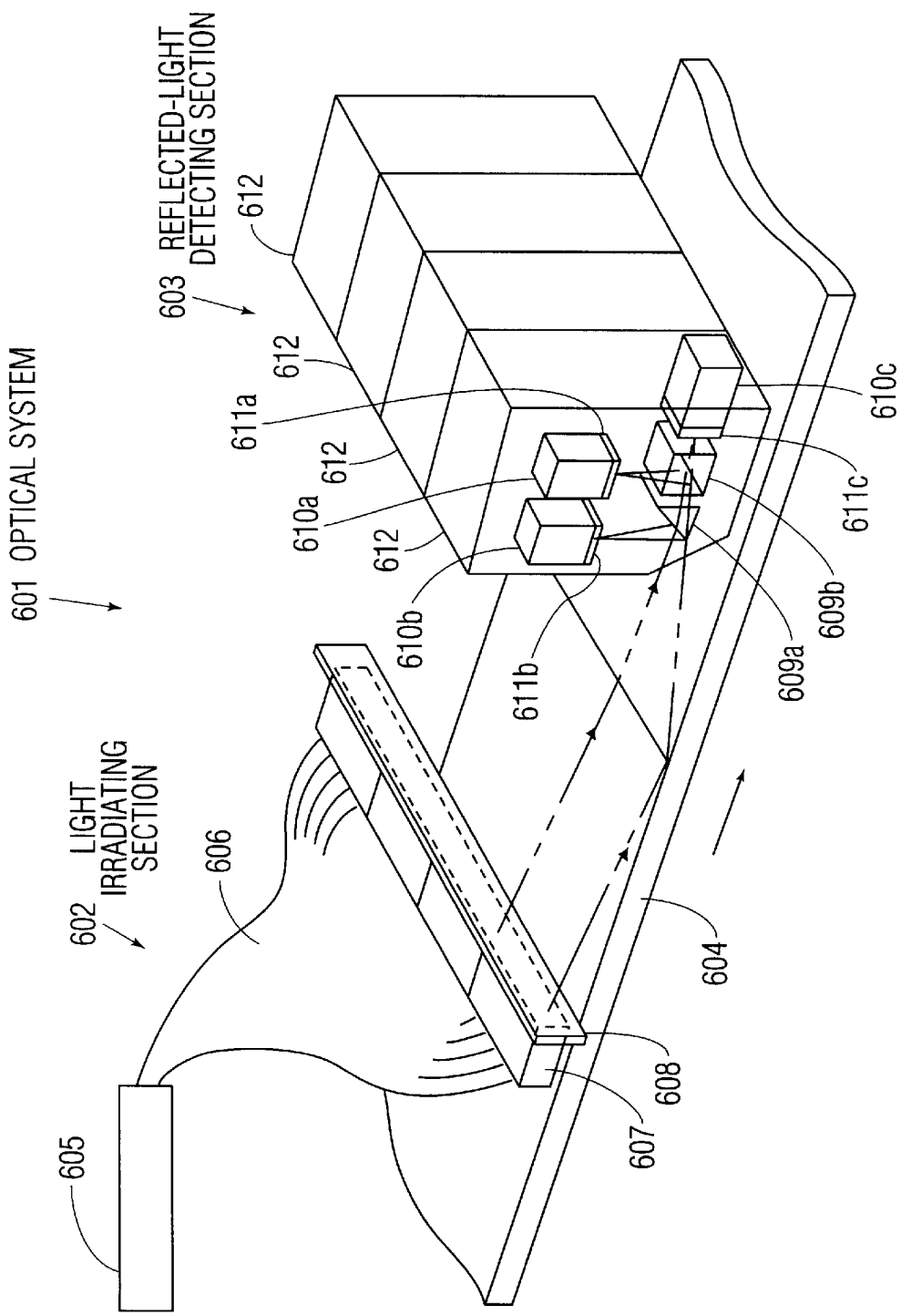
FIG. 49 is a layout view showing an optical system in an embodiment of the present invention.

FIG. 49 is a layout view of an optical system for use in the surface flaw detecting apparatus of this embodiment. As shown in FIG. 49, an optical system 601 comprises a light irradiating section 602 and a reflected light detecting section 603. The light irradiating section 602 irradiates polarized light to the surface of a product to be inspected, e.g., a steel plate 604, over its full width at a certain incident angle. The light irradiating section 602 comprises a light source 605, a bundle of optical fibers 606 having one ends disposed to face a front surface of the light source 605, a group of lenses 607 disposed at the other ends of the optical fibers 606, and a polarizer 608 disposed in front of the group of lenses 607. In the light irradiating section 602, if a bar-shaped light source extending in the direction of width of the steel plate 604 is used as the light source 605, the bundle of the optical fibers 606 and the group of lenses 607 may be dispensed with. The polarizer 608 comprises, e.g., a polarizing plate or filter and, as shown in an explanatory view of FIG. 50, it is arranged such that an angle $\alpha_1$ formed between the transmission axis P of the polarizing plate and the incident plane on the steel plate 604 is $\pi/4$. The reflected-light detecting section 603 receives the light normally reflected by the steel plate 604 at a reflection angle i. The reflected-light detecting section 603 comprises beam splitters 609, 609b, linear array cameras 610a, 610b, 610c each comprising a CCD camera, for example, and analyzers 611a, 611b, 611c disposed in front of respective light receiving surfaces of the linear array cameras 610a, 610b, 610c, which make up a plurality of image pickup devices 612 arranged side by side in the direction of width of the steel plate 604. The analyzers 611a, 611b, 611c each comprise, e.g., a polarizing plate or filter and, as shown in FIG. 50, they are arranged such that an angle $\alpha_2$ formed between the transmission axis A of each analyzer 611 and the incident plane on the steel plate 604 is 0 for the analyzer 611a, $\pi/4$ for the analyzer 611b, and $-\pi/4$ for the analyzer 611c.

Figure 51:
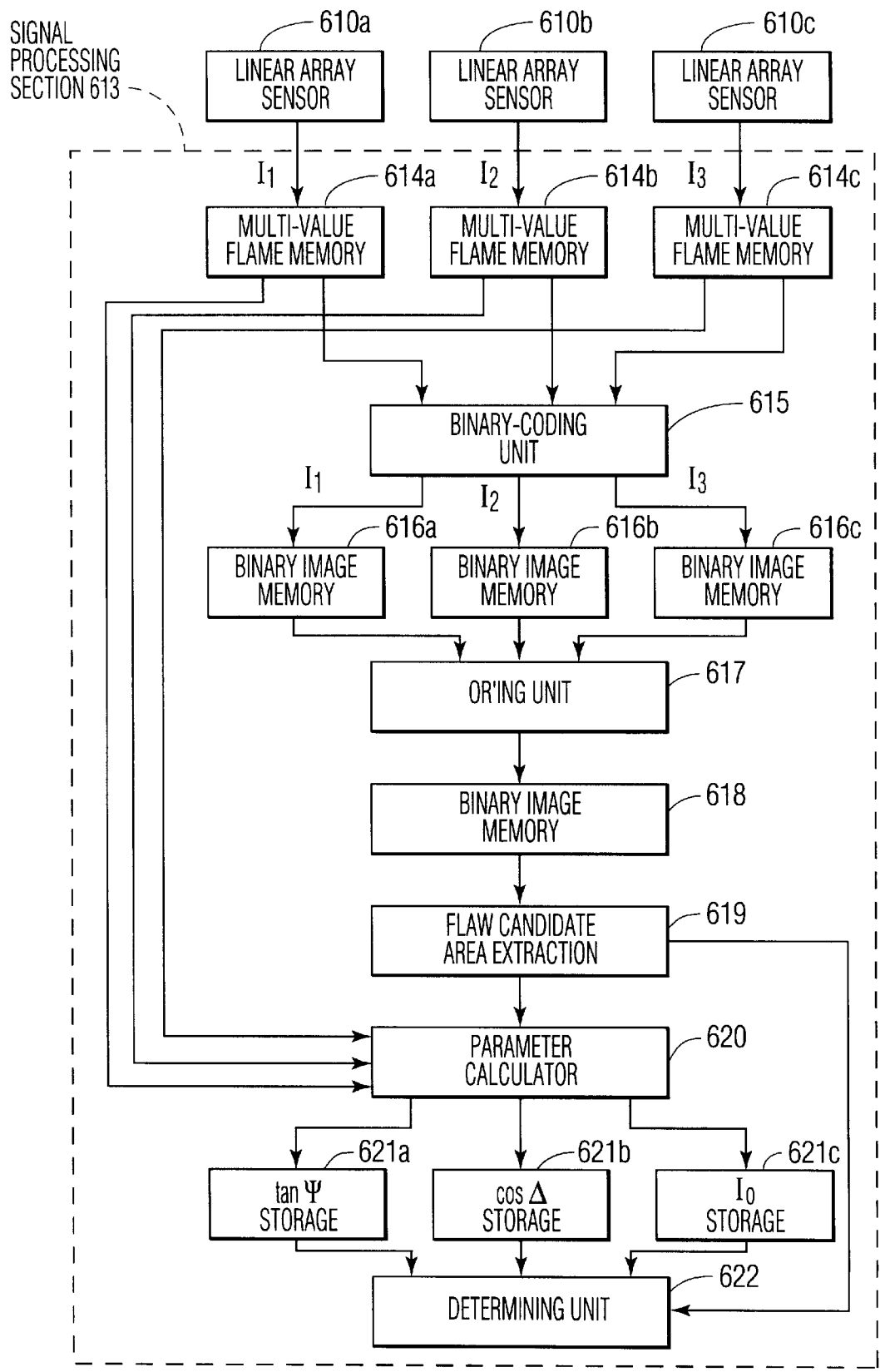
FIG. 51 is a block diagram showing a signal processing section in the embodiment of FIG. 49.

As shown in a block diagram of FIG. 51, the linear array cameras 610a, 610b, 610c of the reflected-light detecting section 603 are connected to a signal processing section 613. The signal processing section 613 comprises multi-value frame memories 614a, 614b, 614c, a binary-coding unit 615, binary image memories 616a, 616b, 616c, an OR'ing unit 617, a binary image memory 618, a flaw candidate area extractor 619, a parameter calculator 620, a tan $\Psi$ storage 621a, a cos $\Delta$ storage 621b, an $I_0$ storage 621c, and a determining unit 622. Image signals representing the reflected light intensities $I_1$, $I_2$, $I_3$ output fi0111 the linear array cameras 610a, 610b, 610c are two-dimensionally developed in the multi-value frame memories 614a, 614b, 614c on a pixel-by-pixel basis to form respective polarization images. The binary-coding unit 615 binary-codes the polarization images stored in the multi-value frame memories 614a, 614b, 614c, and stores the coded binary values in the binary image memories 616a, 616b, 616c, respectively. The OR'ing unit 617 calculates logical OR's of the binary images stored in the binary image memories 616a, 616b, 616c for each pixel, and stores the resulting ORed image in the binary image memory 618. The flaw candidate area extractor 619 specifies the position of a flaw candidate area from the densities of respective pixels of the binary image stored in the binary image memory 618. The parameter calculator 620 calculates the two ellipso-parameters, i.e., the amplitude reflectance ratio tan $\Psi$ and cos $\Delta$ indicative of the phase difference $\Delta$, and the intensity $I_0$ of the reflected light from the surface of the steel plate 604 for respective corresponding pixels from the image signals representing the light intensities $I_1$, $I_2$, $I_3$ at the position within the specified flaw candidate area, and then stores the calculated parameter values in the tan $\Psi$ storage 621a, the cos $\Delta$ storage 621b and the $I_0$ storage 621c, respectively. Various characteristic values of tan $\Psi$, cos $\Delta$ and the reflected light intensity $I_0$ which have been determined beforehand and correspond to surface characteristics of the steel plate 604, i.e., patterned flaws and irregularity flaws such as unevenness in physical property values, unevenness in microscopic roughness, local presence of a thin oxide film or the like, and unevenness in thickness of a coating film, are stored in the determining unit 622. The determining unit 622 compares the values of tan $\Psi$, cos $\Delta$ and the reflected light intensity $I_0$ stored respectively in the tan $\Psi$ storage 621a, the cos $\Delta$ storage 621b and the $I_0$ storage 621c with the characteristic values stored beforehand for each pixel, thereby determining the presence or absence of patterned flaws and/or irregularity flaws on the surface of the steel plate 604 and the type and extent thereof.

Prior to describing the operation of the surface flaw detecting apparatus thus arranged, the principles for calculating the amplitude reflectance ratio tan $\Psi$, cos $\Delta$ and the intensity $I_0$ of the reflected light from the surface of the steel plate 604 based on the light intensities detected by the three linear array cameras 610a, 610b, 610c will first be described.

Figure 50:
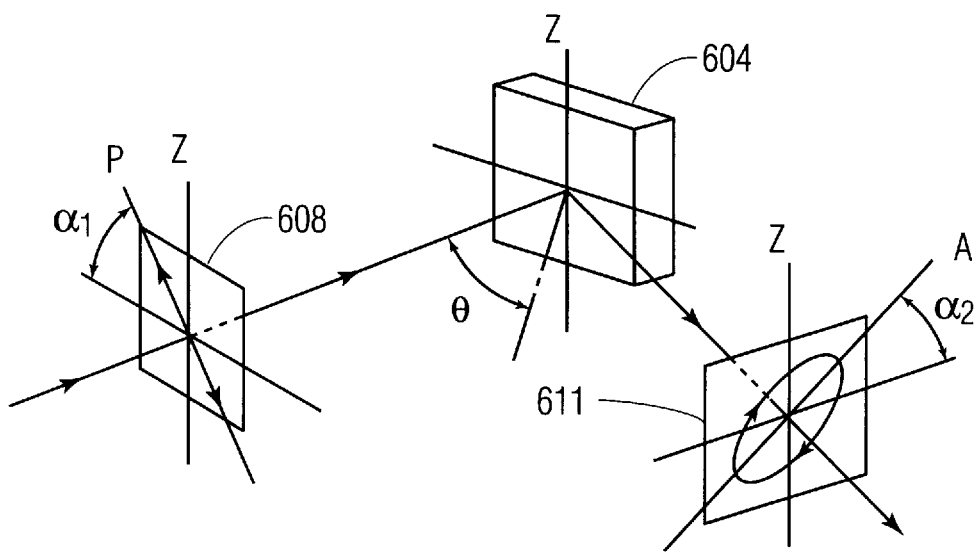
FIG. 50 is an explanatory view showing the operation principle of the optical system in the embodiment of FIG. 49.

Assuming that, as shown in FIG. 50, the angles formed between the transmission axis P of the polarizer 608 and the transmission axis A of each analyzer 611 and the incident plane on the steel plate 604 are $\alpha_1$ and $\alpha_2$, respectively, when a P-polarized light component and an S-polarized light component impinge upon the steel plate 604 at an arbitrary incident angle i and are reflected by the plate surface, the light intensity $I(\alpha_1, \alpha_2)$ of a resultant of the two components after passing through the analyzer 611 is expressed below, given amplitude reflectances of the P- and S-components being $r_P$ and $r_S$, respectively:

$$I(\alpha_1, \alpha_2) = |E_0 \cos\alpha_1 \cdot r_P \cos\alpha_2 + E_0 \sin\alpha_1 \cdot r_s \sin\alpha_2|^2$$
$$= 2I_0[\rho^2 \cos^2\alpha_1 \cdot \cos^2\alpha_2 + \sin^2\alpha_1 \cdot \sin^2\alpha_2 +$$
$$(1/2)\rho \sin 2\alpha_1 \cdot \sin 2\alpha_2 \cdot \cos\Delta]$$

where $$I_0 = |E_0|^2 \cdot R_s/2, r_p = \sqrt{R_P} \cdot \exp(i\phi_p),$$

$$r_s = \sqrt{R_s} \cdot \exp(i\phi_s), \rho = \sqrt{R_P}/\sqrt{R_s} = \tan\Psi,$$

and $\Delta = \phi_p - \phi_s$

Assuming now $\alpha_1 = \pi/4$, the light intensity $I_1$ passing through the analyzer 611a of $\alpha_2 = 0$ is given by $I_1 = I_0 \rho^2$, the light intensity $I_2$ passing through the analyzer 611b of $\alpha_2=\pi/4$ is given by $I_2=I_0(1+\rho^2+2\rho\cos \Delta)/2$, and the light intensity $I_3$ passing through the analyzer 611c of $\alpha_2=-\pi/4$ is given by $I_3=I_0(1+\rho^2-2\rho\cos \Delta)/2$. From these light intensities $I_1$, $I_2$ and $I_3$, tan $\Psi$, cos $\Delta$ and the reflected light intensity $I_0$ are calculated as follows:

$$\tan\Psi = \sqrt{\frac{I_1}{I_2+I_3-I_1}}$$

$$\cos\Delta = \frac{I_2-I_3}{2I_1} \tan\Psi$$

$$I_0 = I_2 + I_3 - I_1$$

Note that any of the light intensities $I_1$, $I_2$ and $I_3$ may be milltiplieda constant depending on selection of amplifier gains of the cameras.

Figure 52A:
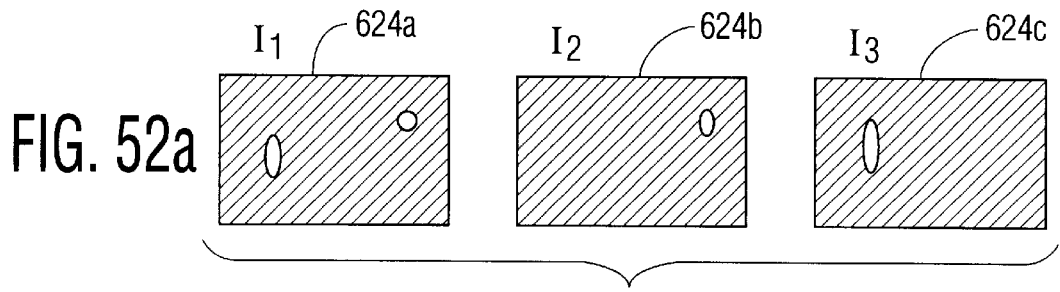
FIGS. 52(a) to 52(d) are image representations for explaining the operation of the embodiment of FIG. 49.

The operation of the apparatus for detecting flaws based on the above principles will be described below. The polarized light irradiated through the light irradiating section 602 to the steel plate 604 moving at a constant speed is reflected by the plate surface and enters the linear array cameras 610a, 610b, 610c through the analyzers 611a, 611b, 611c. When the linear array cameras 610a, 610b, 610c detect the intensity of the reflected light, the linear array camera 610a detects the light intensity $I_1$ as the analyzer 611a of $\alpha_2=0$ is disposed in front of the camera 610a, the linear array camera 610b detects the light intensity $I_2$ as the analyzer 611b of $\alpha_2=\pi/4$ is disposed in front of the camera 610b, and the linear array camera 610c detects the light intensity $I_3$ as the analyzer 611c of $\alpha_2=-\pi/4$ is disposed in front of the camera 610c. The image signals representing the light intensities $I_1$, $I_2$, $I_3$ detected by the linear array cameras 610a, 610b, 610c are two-dimensionally developed in the multi-value frame memories 614a, 614b, 614c on a pixel-by-pixel basis, respectively, to thereby form an $I_1$ polarization image 624a, an $I_2$ polarization image 624b and an $I_3$ polarization image 624c as shown in image explanatory views of FIG. 52(a). Here, the linear array cameras 610a, 610b, 610c are optically adjusted in position and angle to pick up the same viewfield so that the light intensities $I_1$, $I_2$, $I_3$ detected at the same timing show the intensities of polarized components of the light reflected from the same position on the steel plate 604. If the light reflected from the same position cannot be detected by the linear array cameras 610a, 610b, 610c at the same timing, delay circuits or the like may additionally be connected to output terminals of the linear array cameras 610a, 610b, 610c so as to make the picked-up images in match with the same detected position in timing.

Figure 52B:
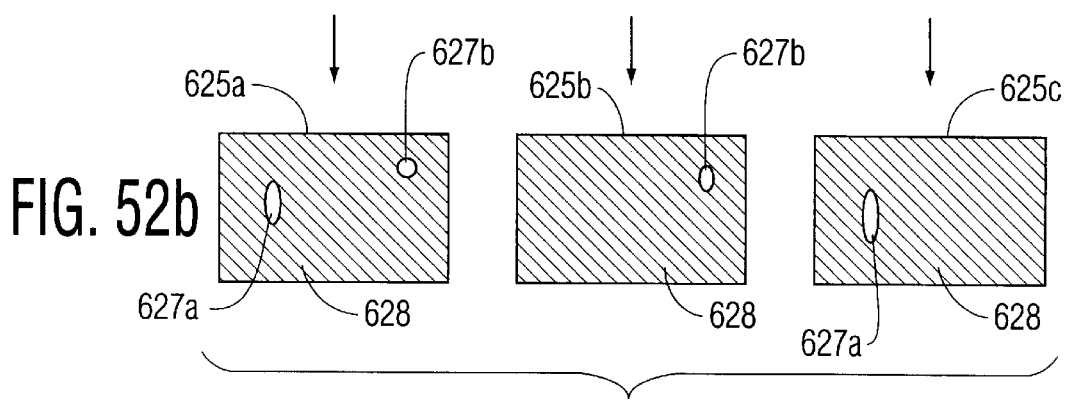
Figure 53:
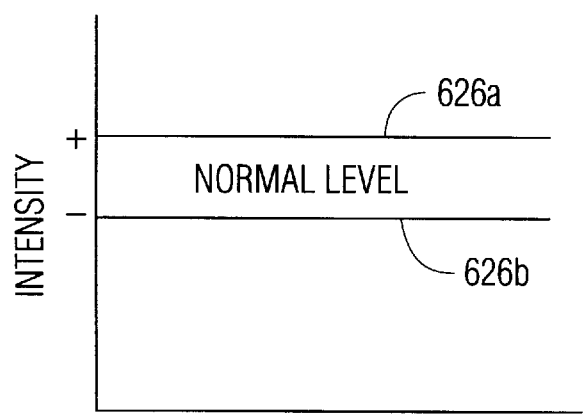
FIG. 53 is a density characteristic graph showing a binary-coding level.

The multi-value frame memories 614a, 614b, 614c each comprise horizontal 1024 pixels×vertical 200 lines, for example, samples one line data of 1024 pixels at the same timing, and stores the sampled data sequentially until reaching 200 lines, thereby forming the $I_1$ polarization image 624a, the $I_2$ polarization image 624b and the $I_3$ polarization image 624c. The binary-coding unit 615 binary-codes the $I_1$ polarization image 624a, the $I_2$ polarization image 624b and the $I_3$ polarization image 624c, as shown in FIG. 52(b), in accordance with binary-coding levels determined beforehand depending on surface roughness of the steel plate 604 and oil coated condition on the plate surface. Resulting binary images 525a, 525b, 525c are stored respectively in the binary image memories 616a, 616b, 616c. In the binary-coding process, while each of the binary-coding levels is determined depending on surface roughness of the steel plate 604 and oil coated condition on the plate surface, that level may be determined automatically from peak values or variations in the measured data and set to a noise level. Also, flaws show levels higher or lower the level indicative of a normal portion depending on the flaw types. As shown in FIG. 53, therefore, the binary-coding is performed by setting two binary-coding levels 626a, 626b which are positive and negative with respect to the normal level. As a result, as shown in FIG. 52(b), flaw portions 627a, 627b are indicated white and a normal portion 628 is indicated black, by way of example.

Figure 52C:
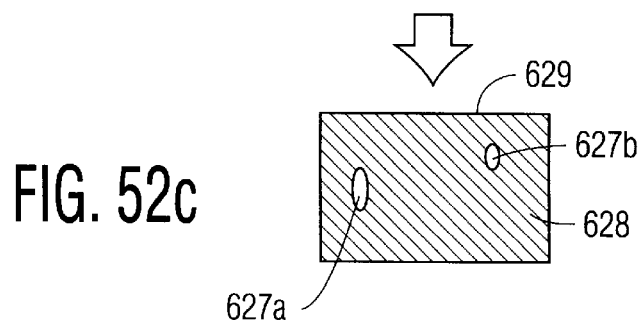
Figure 52D:
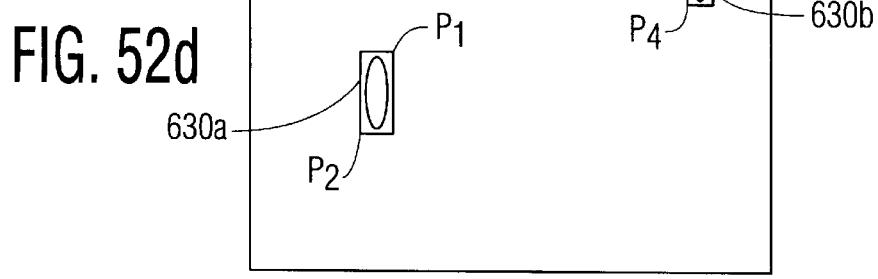

There are three binary images 625a, 625b, 625c representing $I_1$, $I_2$, $I_3$ and, as shown in FIG. 52(b), the flaw portions 627a, 627b are not always detected as abnormal values in common to the three images. As shown in FIG. 52(c), therefore, the OR'ing unit 615 calculates logical OR's of the binary images of $I_1$, $I_2$, $I_3$ for each pixel, and stores the resulting ORed image 629 in the binary image memory 618. The flaw candidate area extractor 619 determines the position of each of white areas showing the flaw portions 627a, 627b in the ORed image 629 stored in the binary image memory 618. Then, as shown in FIG. 52(d), the flaw candidate area extractor 619 extracts, as flaw candidate areas 630a, 630b, rectangular portions circumscribing the white areas, specifies the flaw candidate areas 630a, 630b by reading the coordinate values of two points for each area, e.g., upper right points $P_1$, $P_3$ and lower left points $P_2$, $P_4$, and sends the coordinate values to the parameter calculator 620. The parameter calculator 620 reads, from the multi-value frame memories 614a, 614b, 614c, the light intensities $I_1$, $I_2$, $I_3$ of each pixel within the flaw candidate areas 630a, 630b sent thereto, calculates the two ellipso-parameters, i.e., the amplitude reflectance ratio tan $\Psi$ and the phase difference cos $\Delta$, and the intensity $I_0$ of the reflected light from the surface of the steel plate 604 for each pixel, and then stores the calculated parameter values in the tan $\Psi$ storage 621a, the cos $\Delta$ storage 621b and the $I_0$ storage 621c sequentially. Thus, since the ellipso-parameters, etc. are calculated for only each of the pixel within the flaw candidate areas 630a, 630b, the processing time is much cut down as compared with the case of calculating those parameters for all the pixels in the entire image.

The determining unit 622 compares the values of tan $\Psi$, cos $\Delta$ and the reflected light intensity $I_0$ stored respectively in the tan $\Psi$ storage 621a, the cos $\Delta$ storage 621b and the $I_0$ storage 621c with the characteristic values of the surface of the steel plate 604 stored beforehand for each pixel, thereby determining the flaw type and grade depending on a combination of which ones of the parameters are changed. The determined results are output to display or recording means (not shown). Incidentally, while unevenness in oil coating shows high density levels in the polarization images and is extracted as a flaw, it can be determined as not a flaw it a degree of the unevenness does not amount to a surface flaw, judging from the combination of tan $\Psi$, cos $\Delta$ and the reflected light intensity $I_0$.

Also, by arranging the determining unit 622 to output not only the flaw type and grade, but also the coordinate values of the flaw candidate areas 630a, 630b extracted and specified by the flaw candidate area extractor 619, the flaw size can also be detected and, hence, the flaw condition can be detected more precisely.

When detecting surface flaws of the steel plate 604 as explained above, the size of surface flaws of the steel plate 604 is usually 5 mm ore less wide and 200 mm or less long, and the frequency of flaw occurrence is about once several tens meters in the longitudinal direction of the steel plate. Therefore, if the multi-value frame memories 614a–614c are each configured to have the size of horizontal 1024 pixels× vertical 200 lines, for example, as mentioned above, this size of each of the multi-value frame memories 614a–614c corresponds to a 500 mm width×1.0 m long area of the steel plate 604 on condition that resolution per pixel is of horizontal 0.5 mm×vertical 5 mm. Accordingly, the number of pixels in one image corresponding to a surface flaw is approximately horizontal 10 pixels ×vertical 40 pixels, and the processing time required for calculating the ellipso-parameters, etc. is 1/500 or less as compared with the case of calculating them for all the pixels of the entire image. As a result, the calculation can be completed in several 10's msec without using any special processing unit. Even when the steel plate 604 is moving at a speed of several 100's m per minute, for example, the time necessary for forming an image of 200 lines is several 100's sec. This means that flaws on the moving steel plate 4 can reliably be detected on-line.

As described above, according to Embodiment-7, density levels of the polarization images of the inspected surface input from the three sets of linear array sensors are compared with reference density levels, the areas in which the measured density levels of the polarization images are out of the vicinity of the respective reference density levels are extracted as flaw candidate areas, and the ellipso-parameters and the reflected light intensity for use in determining flaws on the inspected surface are calculated from the measured light intensities of the pixels within the extracted flaw candidate areas. Therefore, the area of those pixels which are to be subjected to processing is restricted and the processing time is much cut down as compared with the case of calculating such parameters for all the pixels of the polarization image. Consequently, surface flaws of a sheet-like material, such as a steel plate, moving at a high speed can precisely be detected on-line.

Additionally, since a processing capability required for the entire apparatus can be held down, the system configuration of the entire apparatus can be simplified and the apparatus cost can also be reduced.

Moreover, since the flaw position is detected by the polarization images having a high S/N at flaw portion as compared with the images of ellipso-parameters, the flaw can be caught with accuracy and without overlooking.

EMBODIMENT-8

A surface flaw detecting apparatus according to this embodiment comprises a light irradiating section, a light receiving section, and a signal processing section. The light irradiating section irradiates polarized light to a surface to be inspected over its full width. The light receiving section comprises beam splitters for separating the reflected light from the inspected surface into three beams, analyzers disposed in respective optical paths of the separated three beams and having different azimuth angles from each other, and linear array sensors for receiving the beams (lights) having passed through the analyzers. The light receiving section receives the reflected light from the inspected surface for conversion into image signals. The signal processing section comprises a parameter calculator, a flaw candidate area extractor, a feature quantity calculator and a flaw determining unit. The parameter calculator calculates the ellipso-parameters and the intensity of the reflected light based on the light intensities of polarization images input from the linear array sensors. The flaw candidate area extractor extracts, as flaw candidate areas, the areas in which density levels of the images of the ellipso-parameters and the reflected light intensity are out of the vicinity of the respective reference density levels corresponding to the background levels. The feature quantity calculator calculates polarities indicating whether maximum values or average values of the ellipso-parameters and the reflected light intensity within the extracted flaw candidate areas are larger or smaller than those values indicative of a normal portion, and calculates a flaw feature quantity in a combination of the calculated polarities of the ellipso-parameters and the reflected light intensity. The flaw determining unit determines the type of a surface flaws from the calculated flaw feature quantity.

Preferably, in addition to the flaw feature quantity in a combination of the polarities of the ellipso-parameters and the reflected light intensity within the flaw candidate area, the feature quantity calculator also calculates another flaw feature quantity in a combination of the polarities of the light intensities in the polarization images within the flaw candidate area. The flaw determining unit determines the type and grade of a surface flaws from both the calculated flaw feature quantity in a combination of the polarities of the ellipso-parameters and the reflected light intensity and the calculated flaw feature quantity in a combination of the light intensities.

The surface flaw detecting apparatus of this embodiment comprises the light irradiating section, the light receiving section, and the signal processing section. The light irradiating section has a light source arranged so as to irradiate emitted light to the inspected surface over its full width at a certain incident angle. A polarizer is disposed between the light source and the position on the inspected surface upon which the incident light impinges, so that polarized light having a certain polarizing plane is irradiated to the inspected surface. The light receiving section comprises three sets of linear array sensors and three analyzers disposed in front of respective light receiving surface of the linear array sensors. The three analyzers are arranged such that they have different azimuth angles from each other, i.e., such that the angles formed between their transmission axes and the incident plane on the inspected surface are, e.g., 0, $\pi/4$ and $-\pi/4$. The three sets of linear array sensors receive the polarized lights having passed through the corresponding analyzers and output images representing intensity distributions of the respective polarized lights to the signal processing section.

The signal processing section comprises the parameter calculator, the flaw candidate area extractor, and the flaw determining unit. From the light intensities of the polarization images input from the three sets of linear array sensors, the parameter calculator calculates the two ellipso-parameters tan $\Psi$ and cos $\Delta$ and the intensity $I_0$ of the reflected light to produce a tan $\Psi$ image, a cos $\Delta$ image and an $I_0$ image. The flaw candidate area extractor stores in advance reference density levels indicating the normal condition of the inspected surface, or automatically determines reference density levels from peak values or variations of the measured data. The flaw candidate area extractor compares density levels of the three sets of tan $\Psi$ image, a cos $\Delta$ image and an $I_0$ image with the reference density levels, and extracts, as flaw candidate areas, the areas in which the density levels of the tan $\Psi$ image, the cos $\Delta$ image and the $I_0$ image are out of the vicinity of the reference density levels. Then, the feature quantity calculator reads the two ellipso-parameters tan $\Psi$ and cos $\Delta$ and the reflected light intensity $I_0$ for each of pixels within the extracted flaw candidate areas, calculates not only polarities indicating whether maximum values and average values of the ellipso-parameters and the reflected light intensity are larger or smaller than those values indicative of a normal portion, but also deviations (change amounts) thereof with respect to the normal portion, and calculates a flaw feature quantity in a combination of the calculated polarities of the ellipso-parameters and the reflected light intensity. The flaw determining unit determines the type of a surface flaw from the calculated flaw feature quantity in a combination of the polarities of the ellipso-parameters and the reflected light intensity.

Thus, since the presence or absence of flaws is determined by detecting the ellipso-parameters tan $\Psi$ and cos $\Delta$ which are varied sensitively depending on surface characteristics of the inspected surface, it is possible to measure change in surface properties which cannot be detected by utilizing-scattering or diffraction of light. Also, since the flaw candidate areas are specified and the flaw type is determined from both the combination of the polarities of the two ellipso-parameters tan $\Psi$ and cos $\Delta$ and the reflected light intensity $I_0$, the flaw type can be determined in a simplified manner and accuracy of flaw detection is improved.

Further, by determining a surface flaw based on not only the combination of the polarities of the two ellipso-parameters tan $\Psi$ and cos $\Delta$ and the reflected light intensity $I_0$ within the flaw candidate areas, but also the combination of the measured light intensities representing the flaw, the flaw type and grade can be determined in more detail.

Figure 54:
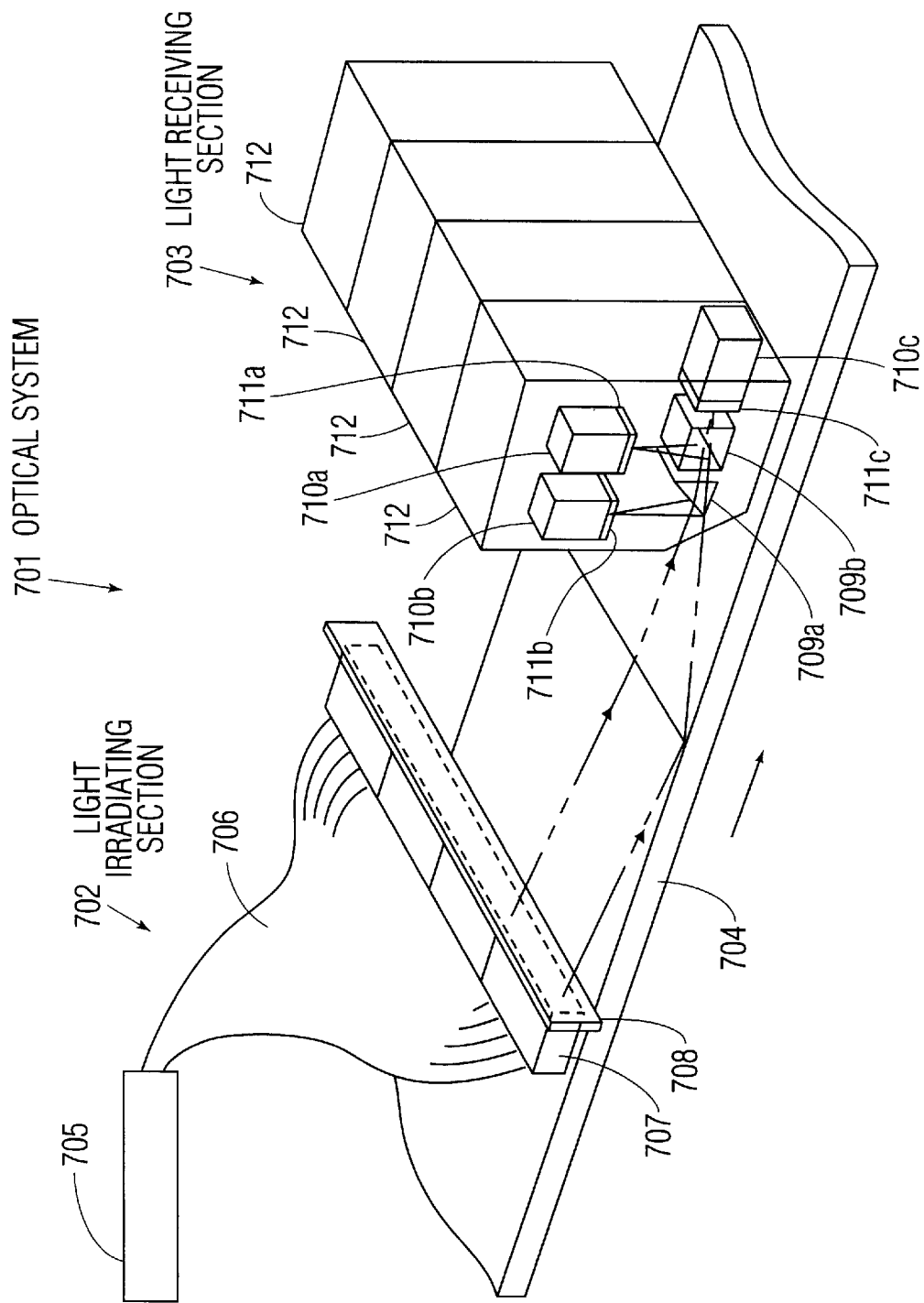
FIG. 54 is a layout view showing an optical system in an embodiment of the present invention.
Figure 55:
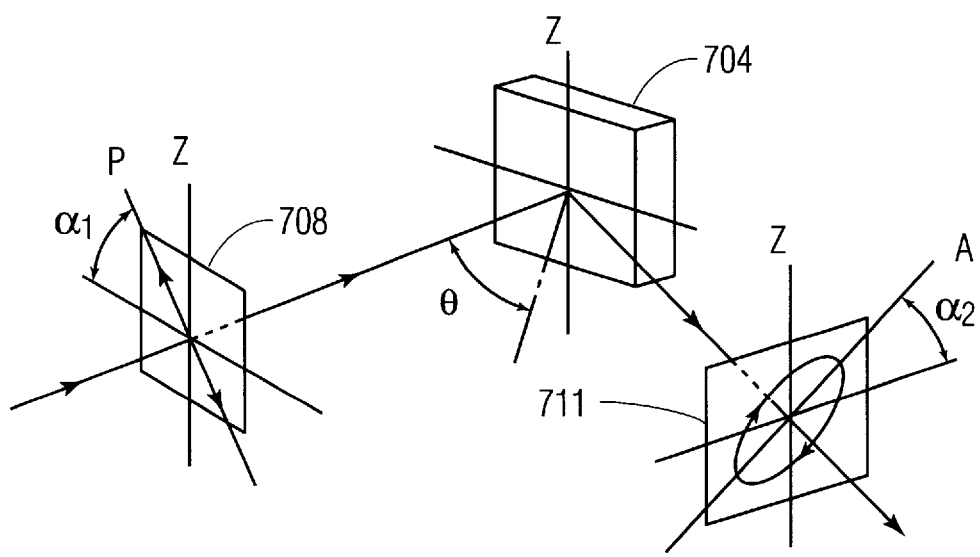
FIG. 55 is an explanatory view showing the operation principle of the optical system in the embodiment of FIG. 54.

FIG. 54 is a layout view of an optical system for use in the surface flaw detecting apparatus of this embodiment. As shown in FIG. 54, an optical system 701 comprises a light irradiating section 702 and a light receiving section 703. The light irradiating section 702 irradiates polarized light to the surface of a product to be inspected, e.g., a steel plate 704, over its full width at a certain incident angle. The light irradiating section 702 comprises a light source 705, a bundle of optical fibers 706 having one ends disposed to face a front surface of the light source 705, a group of lenses 707 disposed at the other ends of the optical fibers 706, and a polarizer 708 disposed in front of the group of lenses 707. In the light irradiating section 702, if a bar-shaped light source extending in the direction of width of the steel plate 704 is used as the light source 705, the bundle of the optical fibers 706 and the group of lenses 707 may be dispensed with. The polarizer 708 comprises a polarizing plate or filter and, as shown in an explanatory view of FIG. 55, it is arranged such that an angle $\alpha_1$ formed between the transmission axis P of the polarizer and the incident plane on the steel plate 704 is $\pi/4$. The light receiving section 703 receives the light normally reflected by the steel plate 704 at a reflection angle $\theta$. The light receiving section 703 comprises beam splitters 709a, 709b, linear array cameras 710a, 710b, 710c each comprising a CCD camera, for example, and analyzers 711a, 711b, 711c disposed in front of respective light receiving surfaces of the linear array cameras 710a, 710b, 710c, which make up a plurality of image pickup devices 712 arranged side by side in the direction of width of the steel plate 704. The analyzers 711a, 711b, 711c each comprise a polarizing plate or filter and, as shown in FIG. 55, they are arranged such that an angle $\alpha_2$ formed between the transmission axis A of each analyzer 711 and the incident plane on the steel plate 704 is 0 for the analyzer 711a, $\pi/4$ for the analyzer 711b, and $-\pi/4$ for the analyzer 711c. The linear array cameras 710a, 710b, 710c output image signals, each being a one-line signal, representing the light intensities $I_1$, $I_2$, $I_3$ of polarized components of the reflected light from the steel plate 704 at a certain period.

Figure 56:
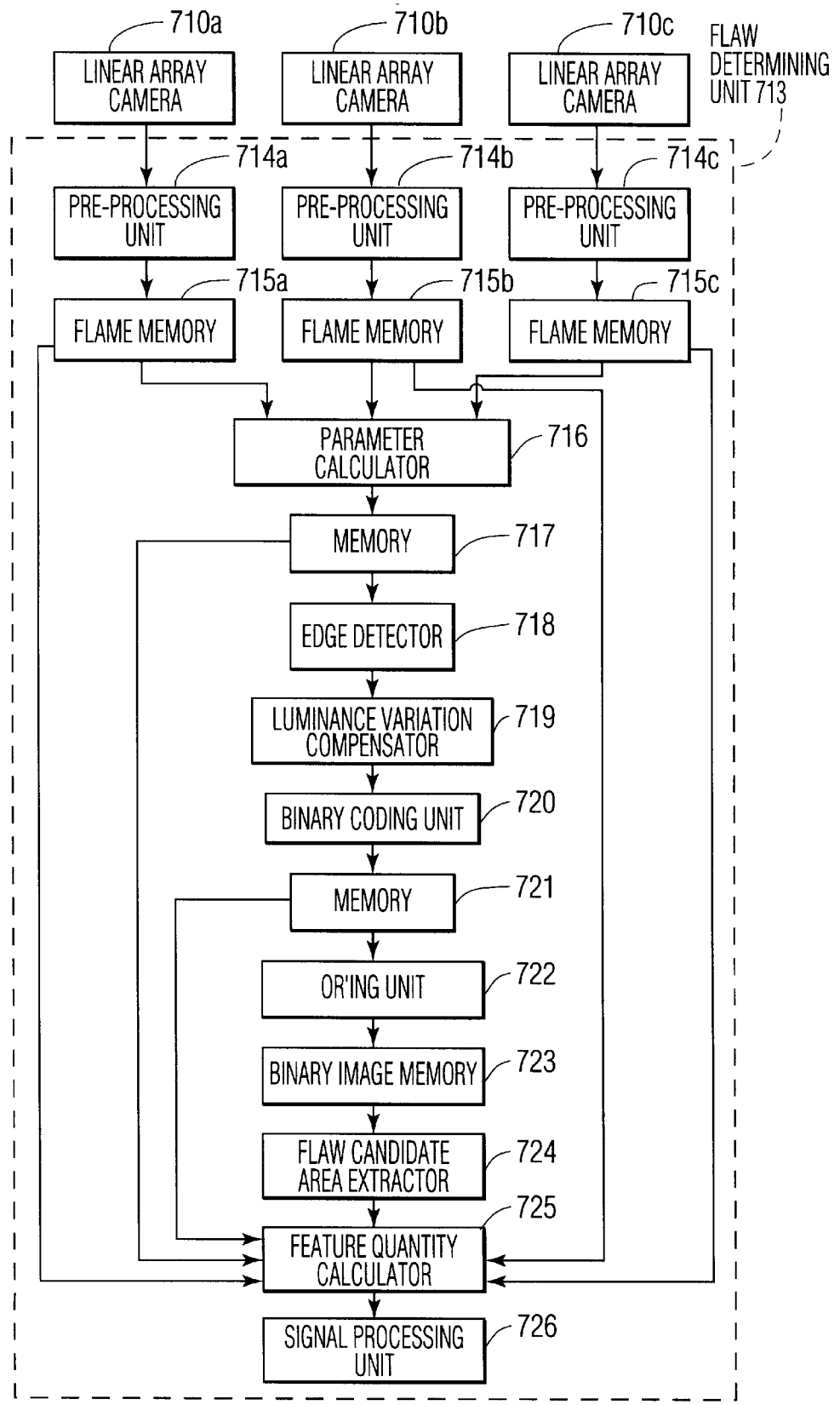
FIG. 56 is a block diagram showing a signal processing section in the embodiment of FIG. 54.

As shown in a block diagram of FIG. 56, the linear array cameras 710a, 710b, 710c of the light receiving section 703 are connected to a signal processing section 713. The signal processing section 713 comprises pre-processing units 714a, 714b, 714c, frame memories 715a, 715b, 715c, a parameter calculator 716, a memory 717, an edge detector 718, a luminance variation compensator 719, a binary-coding unit 720, a memory 721, an OR'ing unit 722, a binary image memory 723, a flaw candidate area extractor 724, a feature quantity calculator 725, and a determining unit 726.

The pre-processing units 714a–714c calculate arithmetic means of the image signals representing the reflected light intensities $I_1$, $I_2$, $I_3$ output from the linear array cameras 710a–710c, detect the distance through which a feed line of the steel plate 704 has moved, and sends the resulting arithmetic mean signals to the frame memories 715a–715c in units of one-line. The frame memories 715a–715c each comprise horizontal 1024 pixels×vertical 200 lines, for example, samples one line data of 1024 pixels at the same timing, and stores the sampled data sequentially until reaching 200 lines, thereby forming a two-dimensional polarization image. The parameter calculator 716 calculates the two ellipso-parameters, i.e., the amplitude reflectance ratio tan $\Psi$ and cos $\Delta$ indicative of the phase difference $\Delta$, and the intensity $I_0$ of the reflected light from the surface of the steel plate 704 based on the image signals representing the light intensities $I_1$, $I_2$, $I_3$, for respective corresponding pixels of the polarization images stored in the frame memories 715a–715c, and then stores the calculated parameter values in the memory 717 as a tan $\Psi$ image, a cos $\Delta$ image and an $I_0$ image, respectively. The edge detector 718 detects edges of the steel plate 704 in the tan $\Psi$ image, the cos $\Delta$ image and the $I_0$ image. The luminance variation compensator 719 compensates for light intensity variations in the widthwise direction due to variations in light intensity of the light source 705 and variations in reflectance of the steel plate, as well as sensitivity variations. The binary-coding unit 720 binary-codes the tan $\Psi$ image, the cos $\Delta$ image and the $I_0$ image, and stores the resulting binary images in the memory 721. The OR'ing unit 722 calculates logical OR's of the binary images of tan $\Psi$, cos $\Delta$ and $I_0$ stored in the memory 721 for each pixel, and then stores the resulting ORed image in the binary image memory 723. The flaw candidate area extractor 724 specifies the position of a flaw candidate area from the densities of respective pixels of the binary image stored in the binary image memory 723. The feature quantity calculator 725 reads tan $\Psi$, cos $\Delta$ and $I_0$ for each of pixels within the flaw candidate area, and calculates maximum values or average values thereof to determine a feature quantity. The flaw determining unit 726 determines flaw types from polarities indicating whether the peak values (the value whose absolute value become maximum) or average values of tan $\Psi$, cos $\Delta$ and $I_0$ within the flaw candidate area are larger or smaller than those values indicative of a normal portion with respect to the normal portion.

Prior to describing the operation of the surface flaw detecting apparatus thus arranged, the principles for calculating the amplitude reflectance ratio tan $\Psi$, cos $\Delta$ and the intensity $I_0$ of the reflected light from the surface of the steel plate 704 based on the light intensities detected by the three linear array cameras 710a, 710b, 710c will first be described.

Assuming that, as shown in FIG. 55, the angles formed between the transmission axis P of the polarizer 708 and the transmission axis A of each analyzer 711 and the incident plane on the steel plate 704 are $\alpha_1$ and $\alpha_2$, respectively, when a P-polarized light component and an S-polarized light component impinge upon the steel plate 704 at an arbitrary incident angle $\theta$ and are reflected by the plate surface, the light intensity $I(\alpha_1, \alpha_2)$ of a resultant of the two components after passing through the analyzer 711 is expressed below, given amplitude reflectances of the P- and S-components being $r_P$ and $r_S$, respectively:

$$I(\alpha_1, \alpha_2) = |E_0\cos\alpha_1 \cdot r_p\cos\alpha_2 + E_0\sin\alpha_1 \cdot r_s\sin\alpha_2|^2$$

$$= 2I_0[\rho^2\cos^2\alpha_1 \cdot \cos^2\alpha_2 + \sin^2\alpha_1 \cdot \sin^2\alpha_2 +$$

$$(1/2)\rho\sin 2\alpha_1 \cdot \sin 2\alpha_2 \cdot \cos\Delta]$$

where $$I_0 = |E_0|^2 \cdot R_s/2, r_p = \sqrt{R_p} \cdot \exp(i\phi_p),$$

$$r_s = \sqrt{R_s} \cdot \exp(i\phi_s), \rho = \sqrt{R_p}/\sqrt{R_s} = \tan\Psi,$$

and $\Delta = \phi_p - \phi_s$

Assuming now $\alpha_1 = \pi/4$, the light intensity $I_1$ passing through the analyzer 711a of $\alpha_2 = 0$ is given by $I_1 = I_0\rho^2$, the light intensity $I_2$ passing through the analyzer 711b of $\alpha_2 = \pi/4$ is given by $I_2 = I_0(1+\rho^2+2\rho\cos\Delta)/2$, and the light intensity $I_3$ passing through the analyzer 711c of $\alpha_2 = -\pi/4$ is given by $I_3 = I_0(1+\rho^2-2\rho\cos\Delta)/2$. From these light intensities $I_1$, $I_2$ and $I_3$, tan $\Psi$, cos $\Delta$ and the reflected light intensity $I_0$ are calculated as follows:

$$\tan\Psi = \sqrt{\frac{I_1}{I_2+I_3-I_1}}$$

$$\cos\Delta = \frac{I_2-I_3}{2I_1}\tan\Psi$$

$$I_0 = I_2 + I_3 - I_1$$

Note that any of the light intensities $I_1$, $I_2$ and $I_3$ may be multiplieda constant depending on selection of amplifier gains of the cameras.

Figure 57A:
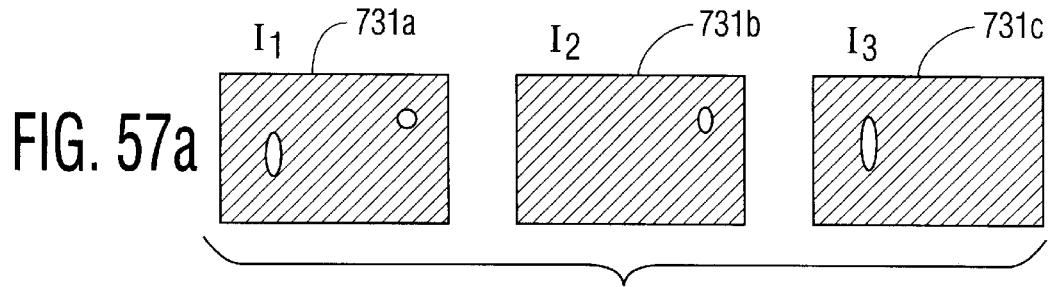
FIGS. 57(a) to 57(d) are image representations for explaining the operation of the embodiment of FIG. 54.

The operation of the apparatus for detecting flaws based on the above principles will be described below. The polarized light irradiated through the light irradiating section 702 to the steel plate 704 moving at a constant speed is reflected by the plate surface and enters the linear array cameras 710a, 710b, 710c through the analyzers 711a, 711b, 711c after being separated into three beams by the splitters 709a, 709b. When the linear array cameras 710a, 710b, 710c detect the intensity of the reflected light, the linear array camera 710a detects the light intensity $I_1$ as the analyzer 711a of $\alpha_2 = 0$ is disposed in front of the camera 710a, the linear array camera 710b detects the light intensity $I_2$ as the analyzer 711b of $\alpha_2\pi/4$ is disposed in front of the camera 710b, and the linear array camera 710c detects the light intensity $I_3$ as the analyzer 711c of $\alpha_2 = -\pi/4$ is disposed in front of the camera 710c. The image signals representing the light intensities $I_1$, $I_2$, $I_3$ detected by the linear array cameras 710a, 710b, 710c are pre-processed by the pre-processing units 714a, 714b, 714c and then two-dimensionally developed in the frame memories 715a, 715b, 715c on a pixel-by-pixel basis, respectively, to thereby form an $I_1$ polarization image 726a, an $I_2$ polarization image 726b and an $I_3$ polarization image 726c as shown in image explanatory views of FIG. 57(a). Here, the linear array cameras 710a, 710b, 710c are optically adjusted in position and angle to pick up the same field of view so that the light intensities $I_1$, $I_2$, $I_3$ detected at the same timing show the intensities of polarized components of the light reflected from the same position on the steel plate 704. If the light reflected from the same position cannot be detected by the linear array cameras 710a, 710b, 710c at the same timing, delay circuits or the like may additionally be connected to output terminals of the linear array cameras 710a, 710b, 710c so as to make the picked-up images with in match the same detected position in timing.

Figure 58:
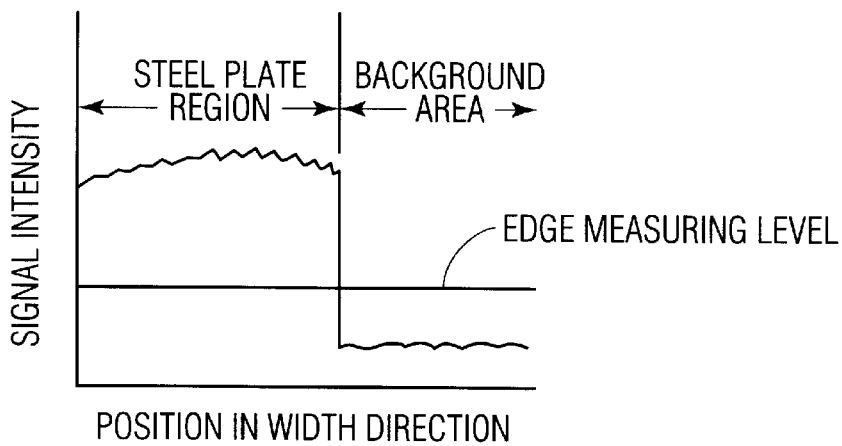
FIG. 58 is a signal intensity distribution chart for explaining the edge detecting operation.
Figure 59A:
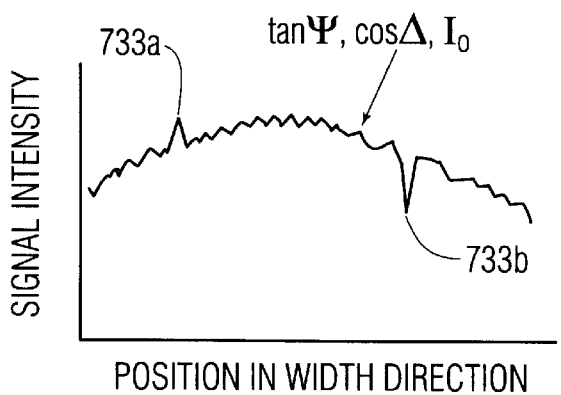
FIGS. 59(a) to 59(c) are charts for explaining the luminance unevenness compensating operation.
Figure 59B:
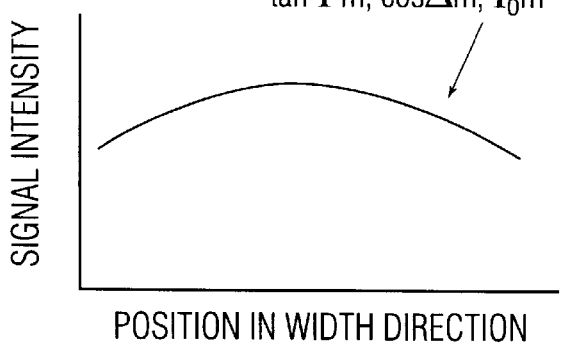
Figure 59C:
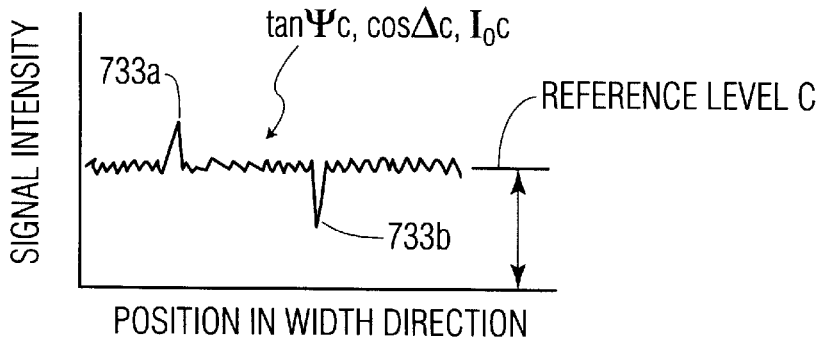

Based on the image signals representing the light intensities $I_1$, $I_2$, $I_3$ for respective corresponding pixels of polarization images 731a to 731c stored in the frame memories 715a–715c, the parameter calculator 716 calculates the two ellipso-parameters, i.e., the amplitude reflectance ratio tan $\Psi$ and cos $\Delta$ indicative of the phase difference $\Delta$, and the intensity $I_0$ of the reflected light from the surface of the steel plate 704, and then stores the calculated parameter values in the memory 717 as tan $\Psi$ image data, a cos $\Delta$ image data and $I_0$ image data, respectively. In the region of the steel plate 704 appearing in each of the tan $\Psi$ image, the cos $\Delta$ image and the $I_0$ image developed in the memory 717, as shown in FIG. 58, a background area outside the region of the steel plate 704 shows a much lower signal level. By utilizing the above fact, the edge detector 718 specifies the point at which the signal level is abruptly changed, as an edge of the steel plate 704, to thereby define a signal processing region. As shown in FIG. 59(a), for example, the intensity of the one-line signal representing each of tan $\Psi$, cos $\Delta$ and $I_0$ for pixels within the signal processing region contains remarkable variations in the widthwise direction. Therefore, the luminance variation compensator 719 calculates a moving mean of the one-line signal over several tens sampling points to the left and right from each reference point at the center in the widthwise direction, and produces moving mean signals tan $\Psi$m, cos $\Delta$m and $I_0$m as shown in FIG. 59(b). Then, as shown in FIG. 59(c), compensated signals tan $\Psi$c, cos $\Delta$c and $I_0$c are calculated in accordance with the following equations for each pixel from the signals tan $\Psi$, cos $\Delta$ and $I_0$ before calculating the moving means and the moving mean signals tan $\Psi$m, cos $\Delta$m and $I_0$m. Note that A is a constant in the following equations.

$$\tan\Psi c = A\frac{\tan\Psi - \tan\Psi m}{\tan\Psi} + C$$

$$\cos\Delta c = A\frac{\cos\Delta - \cos\Delta m}{\cos\Delta} + C$$

$$I_0c = A\frac{I_0 - I_0m}{I_0} + C$$

Figures 60, 61, 62:
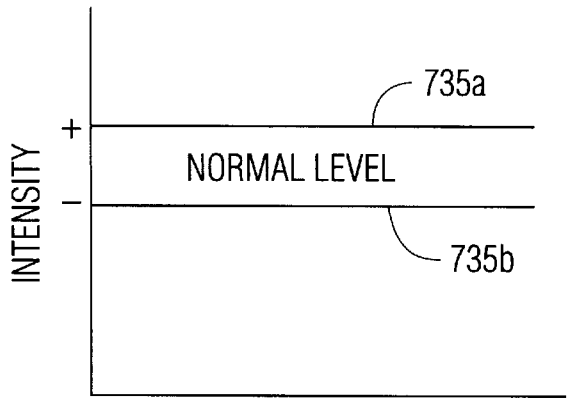
FIG. 60 is a density characteristic graph showing a binary-coding level.
FIG. 61 is a table of polarity characteristics of flaw types for cold-rolled steel plates.
FIG. 62 is a table of polarity characteristics of flaw types for plated steel plates.

In each of the signals resulted from compensating for luminance variations, as shown in FIG. 59(c), a signal level indicative of a flaw 733a which appears brighter than a normal portion 734 (see FIG. 59(b)), i.e., a flaw-free surface of the steel plate 704, is higher than a reference level C indicative of the normal portion 734, and a signal level indicative of a flaw 733b which appeals darker than the normal portion is lower than the reference level C. The thus-compensated images are binary-coded by the binary-coding unit 720 to produce binary images of tan $\Psi$c, cos $\Delta$c and $I_0$c which are stored in the memory 721. In the binary-coding process, while each of the binary-coding levels, i.e., the reference level C, is determined depending on surface roughness of the steel plate 704 and oil coated condition on the plate surface, that level may be determined automatically from peak values or variations in the measured data and set to a noise level. Also, flaws show levels higher or lower the level indicative of the normal portion depending on the flaw types. As shown in FIG. 60, therefore, the binary-coding is performed by setting two binary-coding levels 735a, 735b which are positive and negative with respect to the normal level. Then, the area in which the signal levels are out of the range between the positive binary-coding level 735a and the negative binary-coding level 735b is indicated white, meaning the flaw or abnormal portion, whereas the area in which the signal levels are within the range between the two binary-coding level 735a and 735b is indicated black, meaning the normal portion.

Figure 57B:
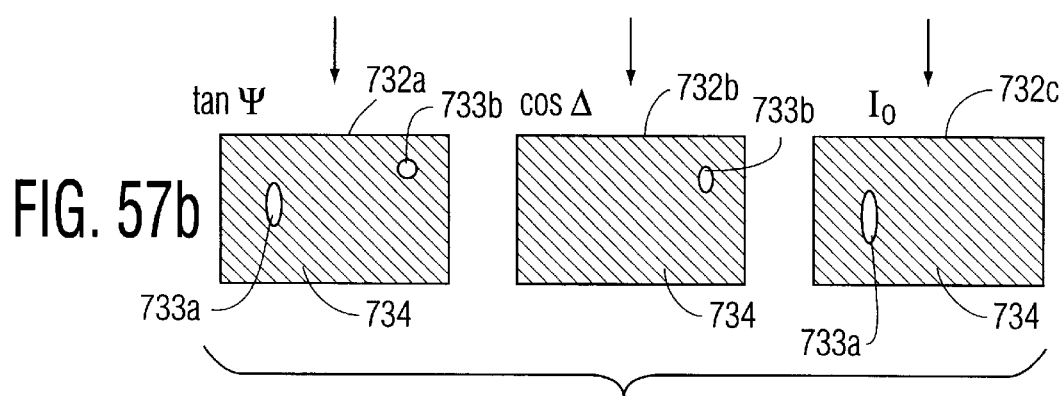
Figure 57C:
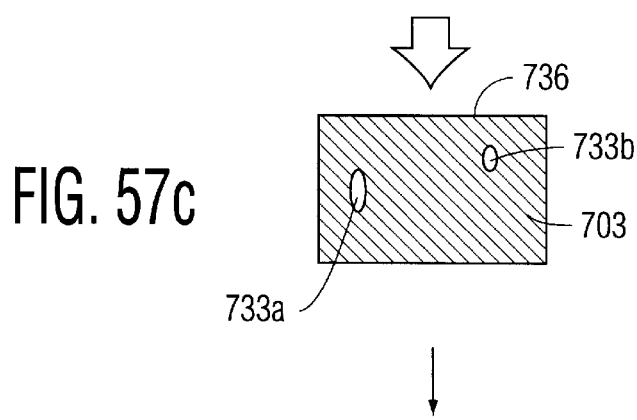
Figure 57D:
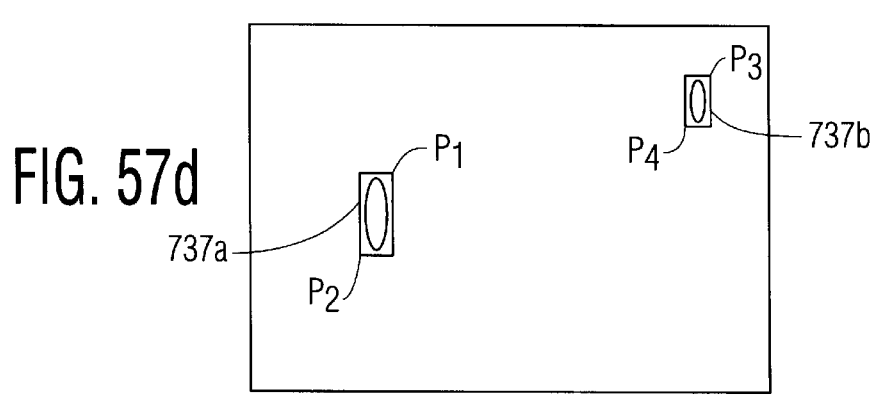

There are three binary images representing tan $\Psi$c, cos $\Delta$c and $I_0$c and, as shown in FIG. 57(b), the flaw 733a, 733b are not always detected as abnormal values in common to the three images. Therefore, the OR'ing unit 722 calculates logical OR's of the binary images of tan Ψc, cos Δc and $I_0$c stored in the memory 721 for each pixel, and then stores an ORed image 726 in the binary image memory 723. The flaw candidate area extractor 724 determines the position of each of white areas showing the flaw 733a, 733b in the ORed image 736 stored in the binary image memory 723. Then, as shown in FIG. 57(d), the flaw candidate area extractor 724 extracts, as flaw candidate areas 737a, 737b, rectangular portions circumscribing the white areas, specifies the flaw candidate areas 737a, 737b by reading the coordinate values of two points for each area, e.g., upper right points $P_1$, $P_3$ and lower left points $P_2$, $P_4$, and sends the coordinate values to the feature quantity calculator 725. The feature quantity calculator 725 reads tan Ψc, cos Δc and $I_0$c for each of pixels within the flaw candidate areas 737a, 737b, and calculates peak values or average values thereof. Then, the feature quantity calculator 725 determines polarities indicating whether the peak values or average values of tan Ψc, cos Δc and $I_0$c within the flaw candidate areas 737a, 737b are larger or smaller than the reference values indicative of the normal portion, and calculates a feature quantity Epp of a polarity pattern by using, e.g., an equation of Epp=9Δp+3Ψp+Ip where Δp represents the polarity of cos Δc, Ψp represents the polarity of tan Ψc, and Ip represents the polarity of $I_0$c. By way of example, each of Δp, Ψp, Ip is set to give "2" when the parameter value is positive, "1" when it is the same as that indicative of the normal portion, and "0" when it is negative.

The flaw determining unit 726 determines the flaw type from the feature quantity Epp for each of the flaw candidate areas 737a, 737b. FIG. 61 shows, by way of example, results of examining polarity changes of tan Ψc, cos Δc and $I_0$c and calculating their flaw quantities E for different flaw types S, T, U, V and W found on surfaces of cold-rolled steel plates. FIG. 62 shows, by way of example, results of examining polarity changes of tan Ψc, cos Δc and $I_0$c and calculating their flaw quantities E for different flaw types S, X, Y, V and W found on surfaces of plated steel plates. The flaw determining unit 726 determines the flaw type based on the above flaw feature quantities E of various flaws and the flaw feature quantity Epp calculated by the feature quantity calculator 725. Although the flaw types cannot be discriminated specifically from one or twos of tan Ψc, cos Δc and $I_0$c, the flaw types can more precisely be discriminated in more detail from a combination of the three polarities of tan Ψc, cos Δc and $I_0$c as shown in FIGS. 61 and 62. For cold-rolled steel plates, by way of example, a flaw having the flaw feature quantity Epp of "0" is judged to be type T, a flaw having the flaw feature quantity Epp of "1" is judged to be type V, a flaw having the flaw feature quantity Epp of "12" is judged to be type W, a flaw having the flaw feature quantity Epp of "18" is judged to be type S, and a flaw having the flaw feature quantity Epp of "24" is judged to be type U.

When the inspector visually judges flaws, the flaws belonging to the same type, e.g., type S, are discriminated more specifically depending on lengths, widths and so on of the flaws. In view of that, the feature quantity calculator 725 also calculates, in addition to the feature quantity Epp of a polarity pattern of tan Ψc, cos Δc and $I_0$c of the pixels within each of the flaw candidate areas 737a, 737b, polarity changes of the light intensities $I_1, I_2, I_3$ of the pixels within each of the flaw candidate areas 737a, 737b with respect to the normal portion, determines a flaw feature quantity Epp of a polarity pattern of the light intensities from the calculated polarity changes in a like manner to the above, and discriminates the flaw type, which can not be determined from the flaw feature quantity Epp representing the polarity pattern of tan Ψc, cos Δc and $I_0$c, based on the flaw feature quantity Ipp representing the polarity pattern of the light intensities $I_1, I_2, I_3$ corresponding to the flaw in more detail. By so determining the flaw type and grade, flaws can precisely be discriminated as with the case of the inspector visually inspecting the flaws.

While the above embodiment is described as calculating tan Ψc, cos Δc and $I_0$c directly from the polarization images, it is also possible to first detect a flaw candidate area by the polarization images and then calculate tantc, cos Δc and $I_0$c for each of pixels within only the flaw candidate area, or calculate tan Ψc, cos Δc and $I_0$c from typical values, e.g., peak or average values, within the flaw candidate area, thereby the feature quantity Epp can be determined.

While the above embodiment is described as using the one-dimensional linear array cameras 710a–710c to detect the reflected light from the steel plate 704, the reflected light from the steel plate 704 may be detected by two-dimensional cameras.

As described above, according to Embodiment-8, a flaw candidate area is extracted from each of three different polarization images, polarities indicating whether peak values or average values of the two ellipso-parameters tan Ψ, cos Δ and the reflected light intensity $I_0$ of pixels within the extracted flaw candidate areas are larger or smaller than those values indicative of a normal portion are calculated, and the flaw type is determined from the flaw feature quantity representing a combination of changes in the calculated polarities of the two ellipso-parameters tan Ψ, cos Δ and the reflected light intensity $I_0$. It is therefore possible to measure change in surface properties which cannot be detected by utilizing scattering or diffraction of light and to improve accuracy of flaw detection.

Also, by evaluating a flaw based on not only the combination of polarities changes of the two ellipso-parameters tan Ψ, cos Δ and the reflected light intensity $I_0$ within the flaw candidate area, but also a combination of polarity changes of the three different measured light intensities corresponding to the flaw, the flaw type and grade can be discriminated more specifically.

What is claimed is:

1. A method for detecting a surface flaw comprising the steps of:
   (a) irradiating a polarized light to a surface of a sample to be inspected and determining ellipso-parameters (Ψ, Δ) of reflected light from the surface of said sample;
   (b) irradiating a light to a same position as irradiated by the polarized light in said step (a) and determining an intensity (I) of reflected light from the surface of said sample; and
   (c) determining a type and grade of a flaw on the surface of said sample based on the ellipso-parameters (Ψ, Δ) determined in said step (a) and the reflected light intensity (I) determined in said step (b).

2. An apparatus for detecting a surface flaw comprising:
   (a) a first measuring device for irradiating a polarized light to a surface to be inspected, and for measuring ellipso-parameters (Ψ, Δ) of reflected light from the surface;
   (b) a second measuring device for irradiating light to a same position as irradiated by the polarized light, and for measuring an intensity (I) of a reflected light from said position; and (c) an output device for outputting a three-dimensional coordinate position of $\Psi$, $\Delta$, I representing said reflected light from the surface, while sorting said position into a preset zone.

3. The apparatus of claim 2, wherein said first measuring device (a) comprises an irradiating device for irradiating the polarized light to the surface, and a light receiving device for receiving the reflected light from the surface; and said light receiving device comprises a plurality of two-dimensional image pickup devices, and the ellipso-parameters ($\Psi$, $\Delta$) of said reflected light are calculated using measured values for respective pixels corresponding to a same reflecting point.

4. The apparatus of claim 2, wherein said first measuring device (a) comprises an irradiating device for irradiating the polarized light to the surface, and a light receiving device for receiving the reflected light from the surface;

said irradiating device comprises a monochromatic light source as a light source of the polarized light, and optical fibers for irradiating the polarized light over a predetermined range of the surface; and said light receiving device comprises a plurality of ellipso-meters for cooperatively receiving said reflected light from the surface.

5. An apparatus for detecting a surface flaw comprising;

(a) a light irradiating device for irradiating a polarized light as a parallel light flux to a surface of a sample to be inspected;

(b) a light receiving device, disposed in respective different optical paths of a reflected light from the surface, for receiving said reflected light from the surface and for converting said received reflected light into image signals;

(c) said light receiving device comprising three analyzers having different azimuth angles from each other, and three linear array sensors for receiving light which has passed through said analyzers so as to produce said image signals; and (d) a signal processing device for processing said image signals produced by said three linear array sensors, wherein said signal processing device calculates an amplitude reflectance ratio tan $\Psi$, cos $\Delta$ indicative of a phase difference $\Delta$ and an intensity $I_0$ of said reflected light from the surface, producing a tan $\Psi$ image, a cos $\alpha$ image and an $I_0$ image, and evaluates surface characteristics from densities of respective corresponding pixels on the tan $\Psi$ image, the cos $\Delta$ image and the $I_0$ image.

6. An apparatus for detecting a surface flaw comprising;

(a) a light irradiating device for irradiating a polarized light to a surface of a sample to be inspected over a full width thereof;

(b) a first detecting device for detecting specularly reflected light from the surface, said first detecting device being disposed in an optical path of the specularly reflected light from the surface;

(c) a second detecting device for detecting scatteringly-reflected light from the surface, said second detecting device being disposed in an optical path of the scatteringly-reflected light from the surface;

(d) at least one of said first detecting device and said second detecting device comprising an optical system for separating incoming light into three beams, analyzers disposed in respective optical paths of the separated three beams and having different azimuth angles from each others and three image pickup devices for receiving light which has passed through said analyzers; and (e) a signal processing device for comparing image signals from said first detecting device and said second detecting device, processing the image signals from said three image pickup devices which have received the light which has passed through said analyzers so as to calculate two ellipso-parameters, including an amplitude reflectance ratio tan $\Psi$ and cos $\Delta$ indicative of a phase difference $\Delta$, of said reflected light from the surface, whereby characteristics of the surface are evaluated from a result of a comparison between the specularly reflected light and the scatteringly-reflected light, as well as the amplitude reflectance ratio tan $\Psi$ and cos $\Delta$.

7. The apparatus of claim 6, wherein said signal processing device calculates the two ellipso-parameters, including the amplitude reflectance ratio tan $\Psi$ and the cos $\Delta$ indicative of the phase difference $\Delta$, of said reflected light from the surface and an intensity $I_0$ of said reflected light from the surface, and evaluates the characteristics of the surface based on a result of a comparison between the specularly reflected light and the scatteringly-reflected light, the amplitude reflectance ratio tan $\Psi$ and the cos $\Delta$, as well as the reflected light intensity $I_0$.

* * * * *

UNITED STATES PATENT AND TRADEMARK OFFICE
CERTIFICATE OF CORRECTION

PATENT NO. : 5,835,220
DATED : November 10, 1998
INVENTOR(S) : Akira KAZAMA et al.

It is certified that error appears in the above-identified patent and that said Letters Patent is hereby corrected as shown below:

Column 8, line 25, change "Surface to --surface--;

Column 17, line 2, change "$\alpha_2=\pi/4$" to --$\alpha_2=-\pi/4$--;

Column 17, line 57, change "thlollgll" to --through--;

Column 27, line 54, change "309" to --302--;

Column 30, line 16, change "$I^{3k}$" to --$I_{3k}$--;

Column 33, line 53, change "$\alpha_2=\pi/4$" to --$\alpha^2=-\pi/4$--;

Column 40, line 49, change "equivalentintensity" to --equivalent intensity--;

Column 40, line 51, change "Of" to --of--;

UNITED STATES PATENT AND TRADEMARK OFFICE
CERTIFICATE OF CORRECTION

PATENT NO. : 5,835,220
DATED : November 10, 1998
INVENTOR(S) : Akira KAZAMA et al.

It is certified that error appears in the above-identified patent and that said Letters Patent is hereby corrected as shown below:

Column 41, line 43, change "equivalentlight" to to --equivalent light--;

Column 43, line 65, change "fi0111" to --from--;

Column 51, line 44, change "$\alpha_2\pi/4$" to --$\alpha_2=\pi/4$--;

Column 54, line 13, change "tantc" to --tan$\Psi$c--;

Column 55, line 49 (claim 5, line 21), change "$\alpha$" to --$\Delta$--.

Signed and Sealed this

Tenth Day of April, 2001

Attest:

NICHOLAS P. GODICI

Attesting Officer     Acting Director of the United States Patent and Trademark Office